(12) United States Patent
Carter et al.

(10) Patent No.: US 8,362,066 B2
(45) Date of Patent: Jan. 29, 2013

(54) COMPOUNDS AND METHODS FOR TREATING PROTEIN FOLDING DISORDERS

(75) Inventors: Michael D. Carter, Toronto (CA); Donald F. Weaver, Halifax (CA); Sheila Marie H. Jacobo, Menands, NY (US); Erhu Lu, Halifax (CA); Fuye Gao, Brantford (CA)

(73) Assignee: Treventis Corporation, Bernville, PA (US)

( * ) Notice: Subject to any disclaimer, the term of this patent is extended or adjusted under 35 U.S.C. 154(b) by 430 days.

(21) Appl. No.: 12/312,543

(22) PCT Filed: Nov. 19, 2007

(86) PCT No.: PCT/CA2007/002096
§ 371 (c)(1),
(2), (4) Date: Feb. 4, 2010

(87) PCT Pub. No.: WO2008/058402
PCT Pub. Date: May 22, 2008

(65) Prior Publication Data
US 2010/0144821 A1    Jun. 10, 2010

Related U.S. Application Data

(60) Provisional application No. 60/859,632, filed on Nov. 17, 2006.

(51) Int. Cl.
*A61K 31/404* (2006.01)
*C07D 209/12* (2006.01)
(52) U.S. Cl. .................................. 514/415; 548/510
(58) Field of Classification Search .................. None
See application file for complete search history.

(56) References Cited

FOREIGN PATENT DOCUMENTS
WO    WO 2006/125324    * 11/2006

OTHER PUBLICATIONS

Dekker et al. J. Agric. Food Chem. vol. 23, No. 4 (1975), pp. 785-791.*
Greig et. al., Ann. N.Y. Acad. Sci., 1035, pp. 290-315.*
Soto, FEBS Letters, 498, pp. 204-207.*

* cited by examiner

*Primary Examiner* — Joseph K. McKane
*Assistant Examiner* — Alicia L Otton

(57) ABSTRACT

The invention is directed to compounds and methods for treating protein folder disorders. In certain embodiments the invention provides compounds and methods for treating neurodegenerative diseases such as Alzheimer's disease, tauopathy, cerebral amyloid angiopathy, Lewy body disease, dementia, Huntington's disease and prion-based spongiform encelopathy. The invention further provides compounds, methods and pharmaceutical compositions for inhibiting tau protein, Aβ protein or α-synuclein protein aggregation.

6 Claims, 16 Drawing Sheets a) Aβ1-40 (20 μM) following ThT aggregation assay (Control)

b) + QR-0112 (20 μM)

c) + QR-0194 (20 μM)

d) + QR-0295 (20 µM)

a) Aβ1-40 (20 μM), no ThT (control)

b) + QR-0263 (20 μM)

c) + QR-0273 (100 μM)

a) Aβ1-42 control b) + QR-0185 (100 μM)

c) + QR-0194 (20 μM)

a) Tau 441 (6 μM)

b) + QR-0281 (20 μM)

c) + QR-0262 (20 μM)

COMPOUNDS AND METHODS FOR TREATING PROTEIN FOLDING DISORDERS

BACKGROUND OF THE INVENTION

Protein folding disorders include neurodegenerative conditions such as, e.g., Alzheimer's disease, dementia, Huntington's disease, Parkinson's disease and prion-based spongiform encephalopathy (e.g., Creutzfeldt-Jakob disease) and non-neural protein folding disorders such as, e.g., type II diabetes and systemic amyloidoses.

Alzheimer's disease (AD) is a progressive neurodegenerative disease which first manifests with mild cognitive, memory and behavioral symptoms that gradually worsen in severity and eventually lead to dementia. It is the most common cause of dementia, accounting for between 42 and 81% of cases, as determined in various studies (Nussbaum, R L; Ellis, C E. *N Engl J Med,* 2003, 348: 1356-64). It affects 2.5% of people 65-74 years of age, 4% of people aged 75-79, 11% of those aged 80-84, and 24% of those aged 85-93 years (Siegel, G J; Agranoff, B W; Albers, R W; Molinoff, P B, *Basic Neurochemistry*. Fifth ed. 1994, New York: Raven Press, 1054 pp). Accounting for 100,000 deaths annually in North America alone. AD is the fourth leading cause of death in industrialized societies, preceded only by heart disease, cancer and stroke (Schenk, D B; Rydel, R E; May, P; Little, S; Panetta, J; Lieberburg, I; Sinha, S. *J Med Chem,* 1995, 38: 4141-54). AD affects individuals in all races and ethnic groups, occurring slightly more commonly in females than males.

There is no remission in the progression of Alzheimer's disease, nor are there any disease-stabilizing drugs currently available (Selkoe, D J; Schenk, D. *Annu Rev Pharmacol Toxicol,* 2003, 43: 545-84). As such, onset of the disease is inevitably followed by increasing mental and physical incapacitation, loss of independent living, institutionalization and death. There is usually an 8-10 year period from symptom onset until death, but patients can survive for 20 years or more after the initial diagnosis of AD is made (Siegel).

A large body of evidence suggests Alzheimer's disease can be viewed as a syndrome of protein misfolding and aggregation (Selkoe D. J. et al. *Arch Neurol* (2005) 62: 192-5, Walsh D. M., et al. *Protein Pept. Lett.* (2004) 11: 213-28). This syndrome accounts for the microscopic features recognized as the hallmarks of the disease: extraneuronal plaques, composed primarily of Aβ peptide, and intraneuronal neurofibrillary tangles (NFT), composed primarily of hyperphosphorylated tau protein (Mirra S. S., et al., *Neurology* (1991) 41: 479-86). In addition to Aβ and tau, aggregates of α-synuclein have also been implicated in AD pathogenesis (Duda J. E., et al,. *J Neurosci. Res*. (2000) 61: 121-7), and may contribute to the widespread cell loss, particularly of cholinergic neurons, in AD brain. Inhibiting the misfolding/aggregation of these proteins, and particularly inhibiting all three at once, is thus of great therapeutic interest.

Accordingly, there exists a need in the art for an agent which can be used for the treatment of Alzheimer's disease and other protein folding disorders.

U.S. application Ser. No. 11/443,396, U.S. Publication No. 2007-0015813, filed May 30, 2006 is hereby incorporated by reference in its entirety for all purposes. All other documents referred to herein are incorporated by reference in their entireties for all purposes.

OBJECTS AND SUMMARY OF THE INVENTION

It is an object of the present invention to provide compounds and methods for treating protein folding disorders.

It is an object of certain embodiments of the present invention to provide compounds and methods for treating neurodegenerative diseases such as, e.g., Alzheimer's disease, tauopathies, cerebral amyloid angiopathy, Lewy body diseases (e.g. Parkinson's disease), dementia, tauopathies, cerebral amyloid angiopathies, Huntington's disease and prion-based spongiform encephalopathy.

It is an object of certain embodiments of the present invention to provide compounds and methods for treating systemic amyloidoses such as, e.g., secondary systemic amyloidosis, particularly those affecting the peripheral nerves, spleen, kidney, heart, intestine, smooth muscle or pancreas, and type II diabetes.

It is an object of the present invention to provide pharmaceutical compositions comprising an effective amount of a compound for treating protein folding disorders.

It is an object of certain embodiments of the present invention to provide pharmaceutical compositions comprising an effective amount of a compound for treating neurodegenerative diseases such as, e.g., Alzheimer's disease, tauopathies, cerebral amyloid angiopathy, Lewy body diseases (e.g. Parkinson's disease), dementia, Huntington's disease, prion-based spongiform encephalopathy and a combination thereof.

It is an object of certain embodiments of the present invention to provide pharmaceutical compositions comprising an effective amount of a compound for treating systemic amyloidoses, particularly those affecting the peripheral nerves, spleen, kidney, heart, intestine, smooth muscle or pancreas.

It is an object of certain embodiments of the present invention to provide compounds, methods and pharmaceutical compositions for inhibiting tau protein aggregation in a subject or patient.

It is an object of certain embodiments of the present invention to provide compounds, methods and pharmaceutical compositions for inhibiting Aβ aggregation in a subject patient.

It is an object of certain embodiments of the present invention to provide compounds, methods and pharmaceutical compositions for inhibiting α-synuclein aggregation.

Other objects and advantages of the present invention will become apparent from the disclosure herein.

In certain embodiments, the present invention is directed to a compound of formula (I):

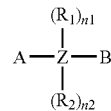

or a pharmaceutically acceptable salt thereof, wherein A and B are each independently a substituted or unsubstituted mono-, bi- or tri-cyclic aromatic or heteroaromatic substituent;

wherein said substituted mono-, bi- or tri-cyclic aromatic or heteroaromatic substituent may each be independently substituted with at least one substituent selected from the group consisting of alkyl, alkenyl, alkynyl, amide, cycloalkyl, heterocycloalkyl, cycloalkenyl, cycloalkynyl, aryl, arylalkyl, alkylaryl, alkylaryl sulfonyl, alkylcarbonyl, alkyl ester, alkoxy, trihalomethoxy, aryloxy, arylcarbonyl, alkoxycarbonyl, aryloxycarbonyl, amino, hydroxy, thio, thioether, cyano, nitro, halogen, carboxylic acid, sulfonic acid, phenyl, benzyl, indolyl, methoxy or ethoxy group;

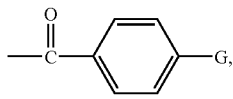

wherein G is alkoxy (e.g., methoxy, ethoxy, propoxy), hydroxy, carboxy, amino, amide, cyano;

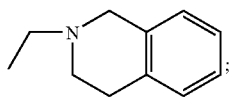

wherein Z is a bond, carbon, or a diamino phenyl

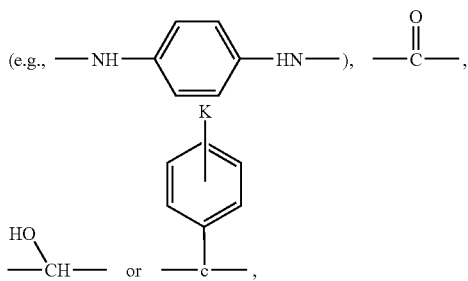

wherein K is selected from the group consisting of H, OH, $OCH_3$, COOH, and $NO_2$;

wherein $n_1$ and $n_2$ are each independently an integer from 0 to 1; and $R^1$ and $R^2$ are each independently selected from the group consisting of hydrogen, alkyl, cycloalkyl, alkoxy, hydroxy, halogen, and aryl, or together represent the group =O or =S.

As used herein, the term "alkyl" means a substituted or unsubstituted linear or branched saturated aliphatic hydrocarbon group having a single radical and 1-10 carbon atoms. Examples of alkyl groups include methyl, propyl, isopropyl, butyl, n-butyl, isobutyl, sec-butyl, tert-butyl, and pentyl. A branched alkyl means that one or more alkyl groups such as, e.g., methyl, ethyl or propyl, replace one or both hydrogens in a —$CH_2$— group of a linear alkyl chain. The term "lower alkyl" means an alkyl of 1-4 carbon atoms.

The term "haloalkyl" means an "alkyl" as defined above connected to a halogen radical (e.g., fluorine, chlorine, iodine, bromine, or astatine).

The term "alkoxy" means an "alkyl" as defined above connected to an oxygen radical.

The term "cycloalkyl" means a substituted or unsubstituted non-aromatic mono- or multicyclic hydrocarbon ring system having a single radical and 3-12 carbon atoms. Exemplary monocyclic cycloalkyl rings include cyclopropyl, cyclopentyl, and cyclohexyl. Exemplary multicyclic cycloalkyl rings include adamantyl and norbornyl.

The term "alkenyl" means a substituted or unsubstituted linear or branched aliphatic hydrocarbon group containing a carbon-carbon double bond having a single radical and 2-10 carbon atoms.

A "branched" alkenyl means that one or more alkyl groups such as, e.g., methyl, ethyl or propyl replace one or both hydrogens in a —$CH_2$— or —CH=linear alkenyl chain. Exemplary alkenyl groups include ethenyl, 1- and 2-propenyl. 1-, 1- and 3-butenyl, 3-methylbut-2-enyl, heptenyl, octenyl and decenyl.

The term "cycloalkenyl" means a substituted or unsubstituted non-aromatic monocyclic or multicyclic hydrocarbon ring system containing a carbon-carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "alkynyl" means a linear or branched aliphatic hydrocarbon group containing a carbon-carbon triple bond having a single radical and 2-10 carbon atoms.

A "branched" alkynyl means that one or more alkyl groups such as, e.g., methyl, ethyl or propyl replace one or both hydrogens in a —$CH_2$— linear alkynyl chain.

The term "cycloalkynyl" means a non-aromatic monocyclic or multicyclic hydrocarbon ring system containing a carbon-carbon triple bond having a single radical and 3 to 12 carbon atoms.

The term "aryl" means a carbocyclic aromatic ring system containing one, two or three rings which may be attached together in a pendent manner or fused, and containing a single radical. Exemplary aryl groups include phenyl, naphthyl and acenaphthyl. "Aryl" includes heteroaryl.

The term "heteroaryl" means unsaturated heterocyclic radicals. Exemplary heteroaryl groups include unsaturated 3 to 6 membered hetero-monocyclic groups containing 1 to 4 nitrogen atoms, such as, e.g., pyrrolyl, pyridyl, pyrimidyl, and pyrazinyl; unsaturated condensed heterocyclic groups containing 1 to 5 nitrogen atoms, such as, e.g., indolyl, quinolyl and isoquinolyl; unsaturated 3 to 6-membered hetero-monocyclic groups containing an oxygen atom, such as, e.g., furyl; unsaturated 3 to 6 membered hetero-monocyclic groups containing a sulfur atom, such as, e.g., thienyl; unsaturated 3 to 6 membered hetero-monocyclic groups containing 1 to 2 oxygen atoms and 1 to 3 nitrogen atoms, such as, e.g., oxazolyl; unsaturated condensed heterocyclic groups containing 1 to 2 oxygen atoms and 1 to 3 nitrogen atoms, such as, e.g., benzoxazolyl; unsaturated 3 to 6 membered hetero-monocyclic groups containing 1 to 2 sulfur atoms and 1 to 3 nitrogen atoms, such as, e.g., thiazolyl; and unsaturated condensed heterocyclic group containing 1 to 2 sulfur atoms and 1 to 3 nitrogen atoms, such as, e.g., benzothiazolyl. The term "heteroaryl" also includes unsaturated heterocyclic radicals, wherein "heterocyclic" is as previously described, in which the heterocyclic group is fused with an aryl group, in which aryl is as previously described. Exemplary fused radicals include benzofuran. benzodioxole and benzothiophene.

The term "carbonyl", whether used alone or with other terms, such as, e.g., "alkoxycarbonyl", is (C=O).

The term "alkylcarbonyl" includes radicals having alkyl radicals, as defined above, attached to a carbonyl radical.

The term "carboxylic acid" is $CO_2H$.

All of the cyclic ring structures disclosed herein can be attached at any point where such connection is possible, as recognized by one skilled in the art.

The terms "bi-indole" and "bis-indole" are used interchangeably.

As used herein, the term "subject" includes a human or an animal such as, e.g., a companion animal or livestock.

The term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Further, as used herein, "an effective amount" or "a therapeutically effective" amount is also intended to refer to the total amount of the active compound of the method that is sufficient to show a meaningful patient benefit. This term is further intended to refer to an amount that returns to normal, either partially or completely, physiological or biochemical parameters associated with induced cellular damage. A non-limiting example of an effective dose range for a pharmaceutical composition of the invention is 0.01-500 mg/kg of body weight per day, more preferably 0.01-50 mg/kg of body weight per day, and still more preferably 0.05-50 mg/kg of body weight per day.

The term "patient" includes a subject in need of therapeutic treatment.

As used herein, the term "halogen" or "halo" is interchangeable with the term "halide" and includes fluoride, bromide, chloride, iodide or astatide.

For purposes of the present invention the abbreviation "Trp" means tryptophan.

For purposes of the present invention the abbreviations "Aβ40" and "Aβ1-40" are synonymous, likewise, "Aβ42" and "Aβ1-42".

The invention disclosed herein is meant to encompass all pharmaceutically acceptable salts thereof of the disclosed compounds. The pharmaceutically acceptable salts include, but are not limited to, metal salts such as, e.g., sodium salt, potassium salt, cesium salt and the like; alkaline earth metals such as, e.g., calcium salt, magnesium salt and the like; organic amine salts such as, e.g., triethylamine salt, pyridine salt, picoline salt, ethanolamine salt, triethanolamine salt, dicyclohexylamine salt, N,N'-dibenzylethylenediamine salt and the like; inorganic acid salts such as, e.g., hydrochloride, hydrobromide, sulfate, phosphate and the like; organic acid salts such as, e.g., formate, acetate, trifluoroacetate, maleate, fumarate, tartrate and the like; sulfonates such as, e.g., methanesulfonate, benzenesulfonate, p-toluenesulfonate, and the like; amino acid salts such as, e.g., arginate, asparginate, glutamate and the like.

The invention disclosed herein is also meant to encompass all prodrugs of the disclosed compounds (see Bundgaard, H. (ed.), "Design of Prodrugs", published by Elsevier, Amsterdam (1985)). Prodrugs are considered to be any covalently bonded carriers which release the active parent drug in vivo. An example of a prodrug would be an ester which is processed in vivo to a carboxylic acid or salt thereof.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as, e.g., a rat, mouse, guinea pig, monkey, or to man, allowing sufficient time for metabolism to occur and isolating its conversion products from the urine, blood or other biological samples. One skilled in the art recognizes that interspecies pharmacokinetic scaling can be used to study the underlining similarities (and differences) in drug disposition among species, to predict drug disposition in an untested species, to define pharmacokinetic equivalence in various species, and to design dosage regimens for experimental animal models, as discussed in Mordenti, *Man versus Beast: Pharmacokinetic Scaling in Mammals*, 1028, Journal of Pharmaceutical Sciences, Vol. 75, No. 11, November 1986.

The invention disclosed herein is also meant to encompass the disclosed compounds being isotopically-labelled by having one or more atoms replaced by an atom having a different atomic mass or mass number. EXAMPLEs of isotopes that can be incorporated into the disclosed compounds include isotopes of hydrogen, carbon, nitrogen, oxygen, phosphorous, fluorine and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Some of the compounds disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

DETAILED DESCRIPTION

Figure 1:
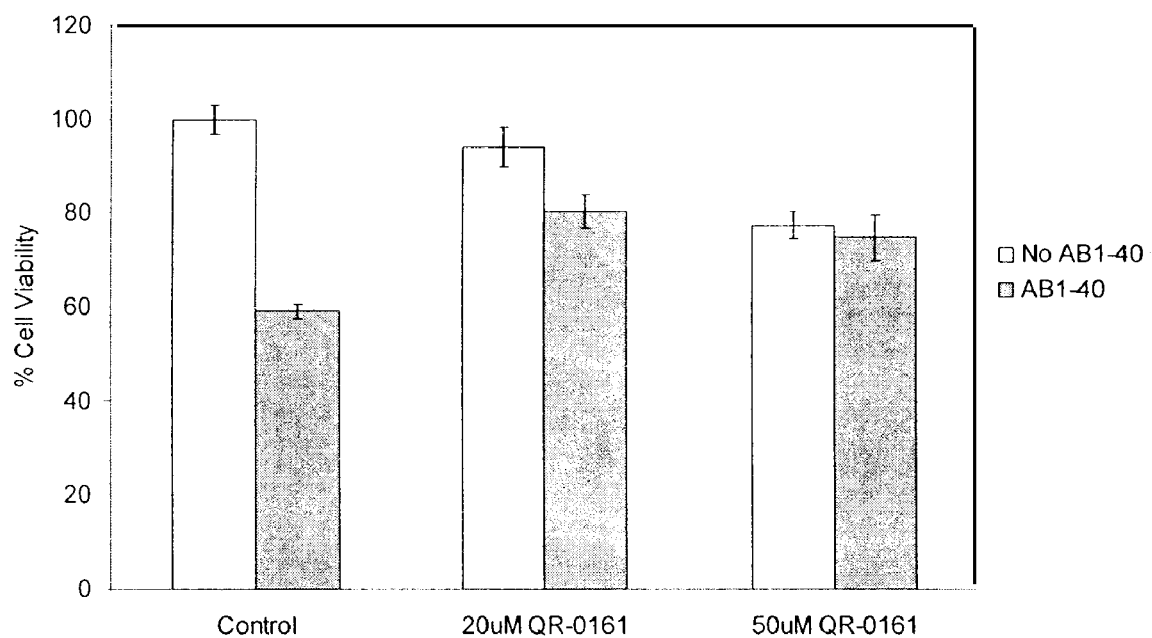
FIG. 1 is % cell viability graph for the cell viability assay performed on QR-0161 in EXAMPLE 50A.

Although the toxic species of protein aggregate are poorly characterized for the proteins involved in AD, there is increasing evidence that "small-n" oligomers, possibly trimers (Townsend M, et al., *J. Physiol.* (2006) 572(Pt 2): 477-92) or dodecamers (Lesné, S., et al., *Nature* (2006) 440: 352-7) in the case of Aβ, are the primary mediators of neurotoxicity. Regardless of the size of Aβ, tau and α-synuclein aggregates, compounds that bind to and/or alter the distribution of toxic aggregates are likely to disrupt the toxic action of these aggregates on neurons and may have potential to reduce toxicity of these aggregates.

This can happen in a number of different ways, for example: 1) compounds can stabilize monomers or aggregates smaller than the one(s) that induce neurotoxicity, thereby reducing the pool of toxic aggregates; 2) compounds may bind to toxic aggregates and block their detrimental interaction at neurons; 3) in binding to toxic aggregates, compounds may promote their breakdown into smaller, non-toxic aggregates; 4) metabolism/clearance of Aβ may be facilitated by compounds which promote a shift to smaller aggregate sizes, etc. Anti-Aβ drug candidates which may function through one or more of these pathways include tramiprosate (Kisilvesky, Szarek & Weaver, 1997-2005; Gervais et al., 2006), currently in Phase III human clinical trials, and isomers of inositol (McLaurin, 2006).

Compounds

The compounds of the present invention are recently-developed small organic molecules (e.g., "bi-aromatics") capable of binding to and modulating or altering, e.g., inhibiting, the aggregation of amyloidogenic proteins implicated in AD, i.e. Aβ, tau and α-synuclein (Carter et al., U.S. patent application Ser. No. 11/443,396, U.S. Publication No. 2007-0015813).

It is believed that the compounds and methods of the present invention will result in a therapeutic outcome by binding the $His_{13}$-$His_{14}$-$Gln_{15}$-$Lys_{16}$ region of Aβ via cation-π interactions, rather than cationic-anionic interactions (See Giulian, D. et al "The HHQK Domain of β-Amyloid Provides a Structural Basis for the Immunopathology of Alzheimer's Disease," The Journal of Biological Chemistry, Vol. 274, No. 45, pp 29719-29726, 1988). Without being bound by theory, it is believed that, in certain embodiments, the compounds of the present invention (e.g., containing two aromatic groups as described herein) would form cation-π interactions at two of the three cationic residues in the $His_{13}$-$His_{14}$-$Gln_{15}$-$Lys_{16}$ region and thereby interfere with Aβ aggregation.

Further, in certain embodiments, unlike tramiprosate (Gervais, F., et al., "Targeting soluble Abeta peptide with Tramiprosate for the treatment of brain amyloidosis." *Neurobiol Aging,* online pre-publication, May 1, 2006) and inositol (McLaurin, J., et al., *Nat. Med.* (2006) 12: 801-8), which have been suggested to work only against Aβ, the compounds of the present invention (e.g., bi-aromatics) in addition to acting on Aβ may also act on tau and/or α-synuclein, thereby providing additive or, in certain embodiments, synergistic effects (i.e. by acting at three different targets in AD, the net effect of the compounds may be greater than the sum of the individual effects). Further, in certain embodiments, because compounds of these embodiments are non-peptidic, small organic molecules, they are expected to overcome deficiencies of peptidic compounds such as poor pharmacokinetics, e.g., degradation by proteases.

In certain embodiments, the present invention is directed to a compound of formula (I):

or a pharmaceutically acceptable salt thereof, wherein A and B are each independently a substituted or unsubstited mono-, bi- or tri-cyclic aromatic or heteroaromatic substituent;

wherein said substituted mono-, bi- or tri-cyclic aromatic or heteroaromatic substituent may each be independently substituted with at least one substituent selected from the group consisting of alkyl, alkenyl, alkynyl, amide, cycloalkyl, heterocycloalkyl, cycloalkenyl, cycloalkynyl, aryl, arylalkyl, alkylaryl, alkylarylsulfonyl, alkylcarbonyl, alkyl ester, alkoxy, trihalomethoxy, aryloxy, arylcarbonyl, alkoxycarbonyl, aryloxycarbonyl, amino, hydroxy, thio, thioether, cyano, nitro, halogen, carboxylic acid, sulfonic acid, phenyl, benzyl, indolyl, methoxy or ethoxy group, wherein any of these substituents are either substituted or unsubstituted;

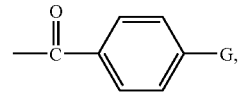

wherein G is alkoxy (e.g., methoxy, ethoxy, propoxy), hydroxy, carboxy, amino, amide, cyano;

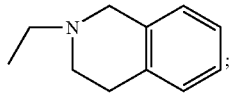

wherein Z is a bond, carbon, or a diamino phenyl

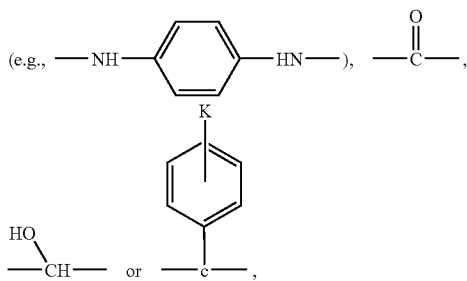

wherein K is selected from the group consisting of H, OH, OCH$_3$, COOH, halogen, and NO$_2$;

wherein $n_1$ and $n_2$ are each independently an integer from 0 to 1; and $R_1$ and $R_2$ are each independently selected from the group consisting of hydrogen, alkyl, cycloalkyl, alkoxy, hydroxy, halogen, and aryl, or together represent the group =O or =S.

In certain embodiments, A and B of formula (I) are each independently selected from the group consisting of substituted or unsubstituted indolyl, benzofuranyl, naphalinyl, naphthyl, benzofuranyl, benzodiaxonyl, phenyl, benzol, phenol, benzothiophenyl, benzopiperidinyl, pyridyl, pyrrolyl, thiophenyl, furanyl, triazolyl, quinolinyl, isoquinolinyl, benzooxazolyl and benzimidazolyl, wherein said substitution, if present, is with at least one substituent selected from the group consisting of alkyl, haloalkyl, alkenyl, alkynyl, cycloalkyl, heterocycloalkyl, cycloalkenyl, cycloalkynyl, aryl, arylalkyl, alkylaryl, alkylarylsulfonyl, alkylcarbonyl, alkyl ester, aryl ester, alkoxy, trihalomethoxy, aryloxy, arylcarbonyl, alkoxycarbonyl, aryloxycarbonyl, amino, hydroxy, thio, thioether, cyano, nitro, halogen, carboxylic acid, sulfonic acid, benzyl, methoxy or ethoxy group.

In certain embodiments, at least one of A and B is selected from the group consisting of indolyl, benzofuranyl, naphthalinyl, benzofuranyl, benzodioxanyl, benzopiperidinyl, phenolyl, methoxybenzyl, and ethoxybenzyl, all unsubstituted or substituted with the substituents as defined above.

In certain embodiments, both A and B of formula (I) are unsubstituted indolyl or an indolyl substituted with the substituents as defined above.

In certain embodiments, the present invention is directed to a compound of formula (II):

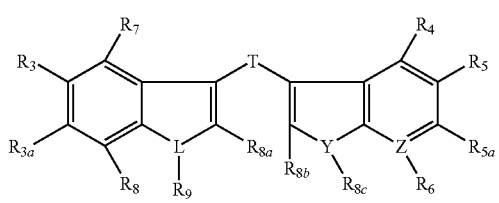

or a pharmaceutically acceptable salt thereof wherein $R_3$, $R_{3a}$, $R_4$, $R_5$, $R_{5a}$, $R_6$, $R_7$, $R_8$, $R_{8b}$, and $R_{8c}$ are each independently selected from the group consisting of hydrogen, halogen, nitro, alkoxy (e.g., methoxy, ethoxy, propoaxy, etc.), alkyl, amide (e.g., —CONH$_2$), haloalkyl, aryl, alkylaryl, hydroxy, carboxy, cyano, carboxyalkyl (e.g., CH$_3$O$_2$C—, etc.), alkylcarbonyl, alkyl ester and carboxylic acid; wherein said halogen is fluorine, chlorine, iodine, bromine, or astatine;

$R_{8a}$ is hydrogen, lower alkyl or carboxylic acid;

$R_9$ is hydrogen, substituted or unsubstitued benzyl, or does not exist;

T is a bond, carbon,

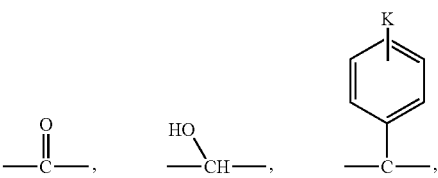

wherein

K is selected from the group consisting of H, OH, OCH$_3$, COOH, and NO$_2$;

L and Y are each independently selected from the group consisting of carbon, nitrogen, oxygen and sulfur; and Z is selected from the group consisting of carbon and nitrogen. It would be understood by a person skilled in the art that in a compound such as, for example, formula (II), when L is oxygen, its valency is complete and so $R_9$ does not exist, and likewise when Z is nitrogen, $R_6$ does not exist.

In certain embodiments, L and Y are both nitrogens, and $R_{3a}$, $R_4$ and $R_8$ are each hydrogen.

In certain embodiments, the compound of formula (II) is 3-(2-methoxynaphthalen-6-yl)-1H-indole-5-carboxylic acid.

In certain embodiments, the compound of formula (II) is 3-(2-hydroxynaphthalen-6-yl)-1H-indole-5-carboxylic acid.

In certain embodiments, the present invention is directed to a compound of formula (III):

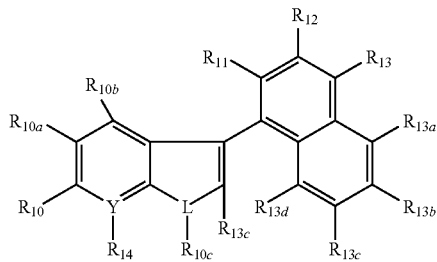

or a pharmaceutically acceptable salt thereof, wherein $R_{10}$, $R_{10a}$, $R_{10b}$, $R_{11}$, $R_{12}$, $R_{13}$, $R_{13a}$, $R_{13b}$, $R_{13c}$, $R_{13d}$, $R_{13e}$ and $R_{14}$ are each independently selected from the group consisting of hydrogen, halogen, nitro, alkoxy (e.g., methoxy, ethoxy, propoxy, etc.), alkyl (e.g., methyl, ethyl, propyl, etc.), amide (e.g., —CONH$_2$); haloalkyl, hydroxy, carboxy, carboxyalkyl (e.g., CH$_3$O$_2$C—, etc.), cyano, alkylcarbonyl, alkyl ester and carboxylic acid; wherein said halogen is fluorine, chlorine, iodine, bromine, or astatine;

$R_{10c}$ is hydrogen or substituted or unsubstitued benzyl,

Y and L are each independently selected from the group consisting of carbon, nitrogen, oxygen and sulfur. In certain embodiments of the present invention, $R_{10a}$ is carboxylic acid and $R_{11}$ and $R_{12}$ are each independently hydroxy.

In certain embodiments, L is oxygen or nitrogen, Y is carbon, and $R_{10}$, $R_{10b}$, $R_{13}$, $R_{13a}$, $R_{13b}$, $R_{13c}$, $R_{13d}$, and $R_{14}$ are each hydrogen.

In certain embodiments, the present invention is directed to a compound of formula (IV):

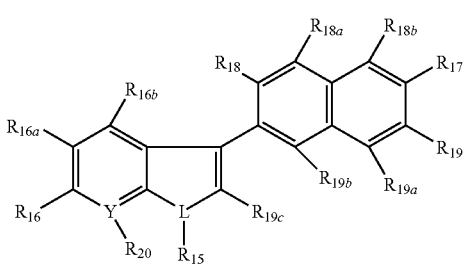

(IV)

or a pharmaceutically acceptable salt thereof,
wherein $R_{16}$, $R_{16a}$, $R_{16b}$, $R_{17}$, $R_{18}$, $R_{18a}$, $R_{18b}$, $R_{19}$, $R_{19a}$, $R_{19b}$, $R_{19c}$ and $R_{20}$ are each independently selected from the group consisting of hydrogen, halogen, nitro, alkoxy (e.g., methoxy, ethoxy, propoxy, etc.), alkyl, amide (e.g., —$CONH_2$), haloalkyl, hydroxy, carboxy, carboxyalkyl (e.g., $CH_3O_2C$—, etc.), cyano, alkylcarbonyl, alkyl ester and carboxylic acid; wherein said halogen is fluorine, chlorine, iodine, bromine, or astatine;

$R_{15}$ is is hydrogen or substituted or unsubstituted benzyl;

Y and L are each independently selected from the group consisting of carbon, nitrogen, oxygen and sulfur.

In certain embodiments $R_1$ is benzyl, and $R_{17}$ is a hydroxy group.

In certain embodiments, the present invention is directed to a compound of formula (V):

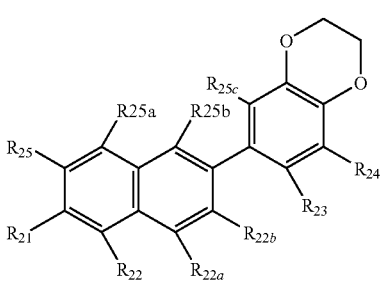

(V)

or a pharmaceutically acceptable salt thereof,
wherein $R_{21}$, $R_{22}$, $R_{22a}$, $R_{22b}$, $R_{23}$, $R_{24}$, $R_{25}$, $R_{25a}$, $R_{25b}$, $R_{25c}$ are each independently selected from the group consisting of hydrogen, halogen, nitro, alkoxy (e.g., methoxy, ethoxy, propoxy, etc.), alkyl, amide (e.g., —$CONH_2$), haloalkyl, hydroxy, carboxy, cyano, alkylcarbonyl, alkyl ester and carboxylic acid; wherein said halogen is fluorine, chlorine, iodine, bromine, or astatine.

In certain embodiments, the present invention is directed to a compound of formula (VI):

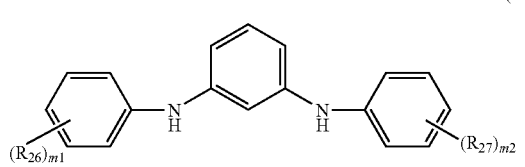

(VI)

or a pharmaceutically acceptable salt thereof,
wherein $R_{26}$ and $R_{27}$ are are each independently selected from the group consisting of hydrogen, halogen, nitro, amino, amide, alkoxy (e.g., methoxy, ethoxy, propoxy, etc.), alkyl, amide (e.g., —$CONH_2$), haloalkyl, hydroxy, carboxy, cyano, alkylcarbonyl, alkyl ester and carboxylic acid; wherein said halogen is fluorine, chlorine, iodine, bromine, or astatine;

and $m_1$ and $m_2$ are each independently an integer from 0 to 5.

In certain embodiments, the present invention is directed to a compound of formula (VII):

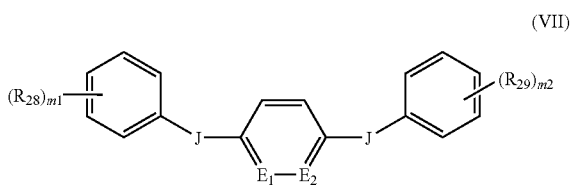

(VII)

or a pharmaceutically acceptable salt thereof,
wherein $R_{28}$ and $R_{29}$ are each independently selected from the group consisting of hydrogen, halogen, nitro, amino, amide (e.g., —$CONH_2$), alkoxy (e.g., methoxy, ethoxy, propoxy, etc.), alkyl, haloalkyl, hydroxy, carboxy, cyano, alkylcarbonyl, alkyl ester and carboxylic acid; wherein said halogen is fluorine, chlorine, iodine, bromine, or astatine;

J is oxygen or NH;

$E_1$ and $E_2$ are each independently carbon or nitrogen, provided that that $E_1$ and $E_2$ are not both nitrogens;

and $m_1$ and $m_2$ are each independently an integer from 0 to 5.

In certain embodiments, both $E_1$ and $E_2$ of formula (VII) are not nitrogen.

In certain embodiments, the present invention is directed to a compound of formula (VIII):

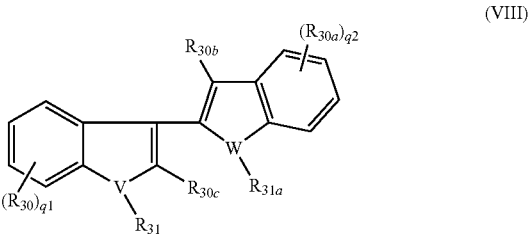

(VIII)

or a pharmaceutically acceptable salt thereof,
wherein V and W are each independently selected from the group consisting of carbon, nitrogen, oxygen and sulfur;

$R_{30}$, $R_{30a}$, $R_{30b}$ and $R_{30c}$ are each independently selected from the group consisting of hydrogen, halogen, nitro, amide (e.g., —CONH$_2$), alkoxy (e.g., methoxy, ethoxy, propoxy, etc.), alkyl, haloalkyl, hydroxy., carboxy, cyano, alkylcarbonyl, alkyl ester and carboxylic acid; wherein said halogen is fluorine, chlorine, iodine, bromine, or astatine;

and $q_1$ and $q_2$ are each independently an integer from 0 to 4;

$R_{31}$ and $R_{31a}$ are each independently selected from the group consisting of hydrogen and unsubstituted or substituted benzyl.

In certain embodiments, the present invention is directed to a compound of formula (IX):

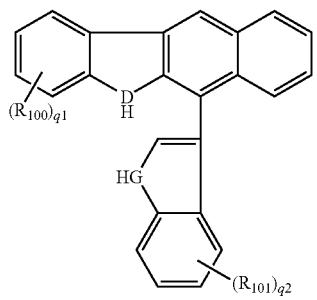

(IX)

or a pharmaceutically acceptable salt thereof, wherein D and G are each independently selected from the group consisting of carbon, nitrogen, oxygen and sulfur;

$R_{100}$ and $R_{101}$ are each independently selected from the group consisting of hydrogen, halogen, nitro, amide (e.g., —CONH$_2$), alkoxy (e.g., methoxy, ethoxy, propoxy, etc.), alkyl, haloalkyl, hydroxy, carboxy, cyano, alkylcarbonyl, alkyl ester and carboxylic acid; wherein said halogen is fluorine, chlorine, iodine, bromine, or astatine; and $q_1$ and $q_2$ are each independently an integer from 1 to 4.

In certain embodiments, the present invention is directed to a compound of formula (X):

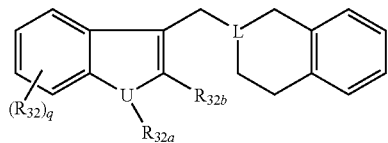

(X)

wherein U is selected from the group consisting of carbon, nitrogen, oxygen and sulfur;

L is selected from the group consisting of carbon and nitrogen;

$R_{32}$, $R_{32a}$ and $R_{32b}$ are each selected independently from the group of hydrogen, halogen, nitro, amide (e.g., —CONH$_2$), alkoxy (e.g., methoxy, ethoxy, propoxy, etc.), alkyl, haloalkyl, hydroxy, carboxy, cyano, alkylcarbonyl, alkyl ester and carboxylic acid; wherein said halogen is fluorine, chlorine, iodine, bromine, or astatine; and and q is an integer from 0 to 4.

In certain embodiments, the present invention is directed to a compound of formula (XI):

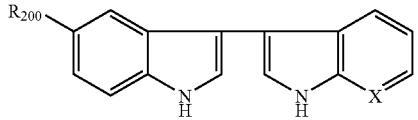

(XI)

or a pharmaceutically acceptable salt thereof, wherein $R_{200}$ is selected from the group consisting of halogen, hydroxy, alkyl, alkoxy and carboxylic acid; and X is selected from the group consisting of nitrogen, oxygen and sulfur. In certain embodiments, $R_{200}$ is carboxylic acid and X is nitrogen.

In certain embodiments, the present invention is directed to a compound of formula (XIIa or XIIb):

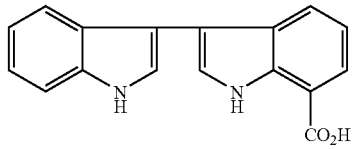

(XIIa)

(XIIb)

or a pharmaceutically acceptable salt thereof.

In certain embodiments, the present invention is directed to a compound of formula (XIII):

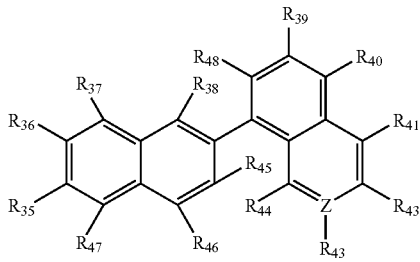

(XIII)

or a pharmaceutically acceptable salt thereof, wherein $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, and $R_{48}$ are each independently selected from the group consisting of hydrogen, halogen, nitro, amide (e.g., —CONH$_2$), alkoxy (e.g., methoxy, ethoxy, propoxy, etc.), alkyl, haloalkyl, hydroxy, carboxy, cyano, alkylcarbonyl, alkyl ester and carboxylic acid; wherein said halogen is fluorine, chlorine, iodine, bromine, or astatine. In certain embodiments, $R_{35}$, $R_{39}$ and $R_{48}$ are hydroxy groups, and $R_{36}$, $R_{37}$, $R_{38}$, $R_{40}$, $R_{41}$, $R_{42}$, $R_{43}$, $R_{44}$, $R_{45}$, $R_{46}$, and $R_{47}$ are each hydrogen.

In certain embodiments, the present invention is directed to a compound of formula (XIV):

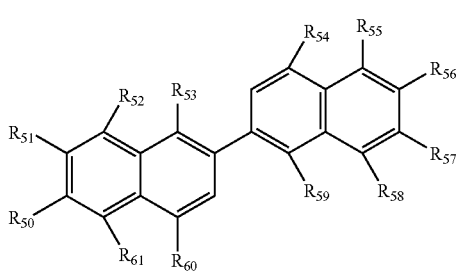

(XIV)

or a pharmaceutically acceptable salt thereof, wherein $R_{50}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, and $R_{63}$ are each independently selected from the group consisting of hydrogen, halogen, nitro, amide (e.g., —$CONH_2$), alkoxy (e.g., methoxy, ethoxy, propoxy, etc.), alkyl, haloalkyl, hydroxy, carboxy, cyano, alkylcarbonyl, alkyl ester and carboxylic acid; wherein said halogen is fluorine, chlorine, iodine, bromine, or astatine.

In certain embodiments, the present invention is directed to a compound of formula (XV):

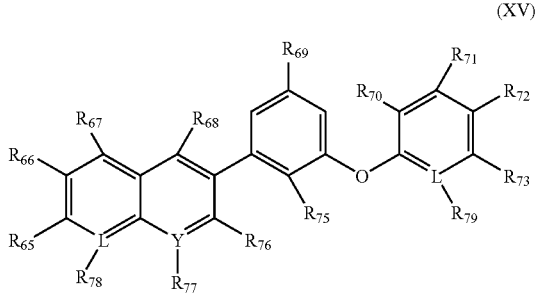

(XV)

or a pharmaceutically acceptable salt thereof, wherein $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$, and $R_{78}$ are each independently selected from the group consisting of hydrogen, halogen, nitro, amide (e.g., —$CONH_2$), alkoxy (e.g., methoxy, ethoxy, propoxy, etc.), alkyl, haloalkyl, hydroxy, carboxy, cyano, alkylcarbonyl, unsubstituted or substituted benzyl, alkyl ester and carboxylic acid; wherein said halogen is fluorine, chlorine, iodine, bromine, or astatine;

L, Y and Z is each independently selected from the group consisting of carbon, nitrogen, oxygen and sulfur;

$R_{79}$ is hydrogen, lower alkyl, or unsubstituted or substituted benzyl.

In certain embodiments, the present invention is directed to a compound of formula (XVI):

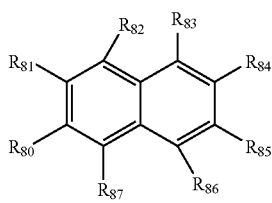

(XVI)

or a pharmaceutically acceptable salt thereof, wherein $R_{80}$, $R_{81}$, $R_{82}$, $R_{83}$, $R_{84}$, $R_{85}$, $R_{86}$, and $R_{87}$ are each individialy selected from the group consisting of hydrogen, halogen, nitro, amide (e.g., —$CONH_2$), alkoxy (e.g., methoxy, ethoxy, propoxy, etc.), alkyl, haloalkyl, hydroxy, carboxy, cyano, alkylcarbonyl, unsubstituted or substituted benzyl, alkyl ester and carboxylic acid; wherein said halogen is fluorine, chlorine, iodine, bromine, or astatine. In certain embodiments, $R_{83}$ is halogen, $R_{84}$ and $R_{85}$ are both hydroxy groups, and $R_{80}$, $R_{81}$, $R_{82}$, $R_{86}$, and $R_{87}$ are all hydrogens. In certain embodiments, $R_{84}$ and $R_{85}$ are both hydroxy groups, and $R_{80}$, $R_{81}$, $R_{82}$, $R_{83}$, $R_{86}$, and $R_{87}$ are all hydrogens.

In certain embodiments, the present invention is directed to a compound of formula (XVII):

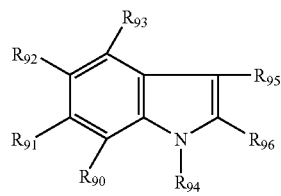

(XVII)

or a pharmaceutically acceptable salt thereof, wherein $R_{90}$, $R_{91}$, $R_{92}$, $R_{93}$ are each independently selected from the group consisting of hydrogen, halogen, nitro, amide (e.g., —$CONH_2$), alkoxy (e.g., methoxy, ethoxy, propoxy, etc.), alkyl, haloalkyl, hydroxy, carboxy, cyano, alkylcarbonyl, unsubstituted or substituted benzyl, alkyl ester and carboxylic acid; wherein said halogen is fluorine, chlorine, iodine, bromine, or astatine;

$R_{94}$ is hydrogen, unsubstituted or substituted benzyl, or

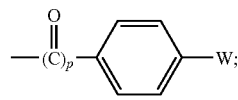

wherein W is alkoxy (e.g., methoxy, ethoxy, propoxy), hydroxy, carboxy, amino, amide, cyano, and p is an integer 0 or 1;

$R_{95}$ and $R_{96}$ is hydrogen,

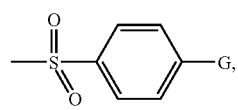

wherein G is alkoxy (e.g., methoxy, ethoxy, propoxy), hydroxy, carboxy, amino, amide, cyano;

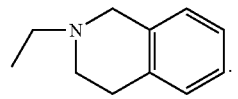

In certain embodiments, the present invention is directed to a compound of formula (XVIII):

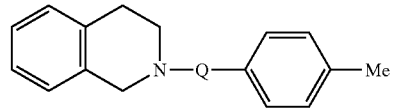

(XVIII)

or a pharmaceutically acceptable salt thereof, wherein Q is a bond, substituted or unsubstituted lower alkyl,

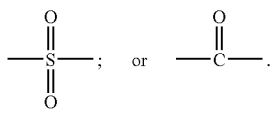

Methods of Preparing

The compounds of the present invention may be synthesized by a number of methods currently used in the chemical art.

For example, the compounds may be prepared by using a Suzuki-coupling reaction. The Suzuki-coupling reaction is the organic reaction of an aryl- or vinyl-boronic acid with an aryl- or vinyl-halide catalyzed by a palladium(0) complex. Potassium trifluoroborates and organoboranes or boronate esters may be used in place of boronic acids. Some pseudohalides (for example triflates) may also be used as coupling partners.

The first step in the reaction is the oxidative addition of palladium to the halide to form an organo-palladium species. Generally, oxidative addition proceeds with retention of stereochemistry with vinyl halides, while giving inversion of stereochemistry with allylic and benzylic halides. The oxidative addition initially forms the cis-palladium complex, which rapidly isomerizes to the trans-complex. The next step in the reaction is a reaction with base, which gives an intermediate, which via transmetallation with the boron-ate complex forms an organopalladium species. Finally, reductive elimination of a desired product restores the original palladium catalyst and leaves a desired compound. Generally, it is believed that the reductive elimination proceeds with retention of stereochemistry.

The compounds of the present invention may also be synthesized by Negishi coupling reaction. The Negishi coupling reaction is a cross coupling reaction involving an organozinc compound, an organic halide (i.e., aryl, vinyl, benzyl, or allyl) and a nickel or palladium catalyst creating a new carbon-carbon covalent bond. Generically, the Negishi coupling reaction can be represented by the following scheme.

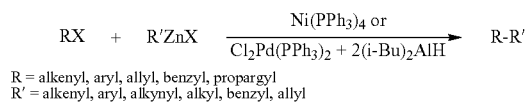

R = alkenyl, aryl, allyl, benzyl, propargyl
R' = alkenyl, aryl, alkynyl, alkyl, benzyl, allyl The active catalyst in this reaction is zerovalent($M^0$) and the reaction in general proceeds through an oxidative addition step of the organic halide followed by transmetalation with the zinc compound and then reductive elimination.

The compounds of the present invention may also be synthesized by Kumada coupling reaction, which is also a Pd or Ni-catalyzed cross coupling reaction. This reaction is the direct coupling of Grignard reagents with alkyl, vinyl or aryl halides, e.g., under Ni-catalysis. The reaction is represented by the following scheme:

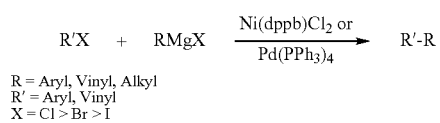

R = Aryl, Vinyl, Alkyl
R' = Aryl, Vinyl
X = Cl > Br > I

In the Kumada coupling reaction, the coupling of Grignard reagents with alkyl, vinyl or aryl halides under Ni-catalysis provides an economic transformation. The Kumada coupling reaction may be the method of choice for the low-cost synthesis of unsymmetrical biaryls of the present invention.

The compounds of the present invention may also be synthesized by Stille reaction. The Stille reaction is a chemical reaction coupling an organotin compound with a $sp^3$-hybridized organic halide catalyzed by palladium. The reaction is represented by the following scheme:

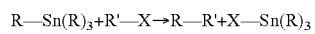

X is typically a halide, or a pseudohalide such as, e.g., a triflate, $CF_3SO_3$. The reaction is usually performed under inert atmosphere using dehydrated and degassed solvent. This is because oxygen causes the oxidation of the palladium catalyst and promotes homo coupling of organic stannyl compounds, and these side reactions lead to a decrease in the yield of the desired cross coupling reaction.

In certain embodiments, prior to conducting a coupling reaction (e.g., Suzuki-coupling reaction), hydroxy substituent(s), if any, e.g., on the alkyl, vinyl or aryl halides; an aryl- or vinyl-boronic acid; an organozinc compound; or Grignard reagent may be protected, e.g., by converting the hydroxy substituent(s) to an alkoxy goup (i.e., methoxy-, -ethoxy, or -propoxy) prior to a coupling reaction, and, then, once the coupling reaction is completed, converting the alkoxy-group back to hydroxy group.

The specific reaction conditions (i.e., temperature, relative amounts of the ingredients, etc.) will be apparent to one skilled in the art, e.g., from the EXAMPLEs given below and general knowledge available in the art.

Methods of Treatment

The compounds of the present invention can be administered to anyone requiring treatment of a protein folding disease or systemic amyloidoses. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, dementia associated with tauopathies, and diffuse Lewy body type Alzheimer's disease. Preferably, the compounds and compositions of the invention are particularly useful for treating or preventing Alzheimer's disease.

In certain embodiments, the invention is directed to a method for treating a protein folding disorder comprising administering a compound or pharmaceutical composition as disclosed herein to a subject wherein the subject is treated for the protein folding disorder.

In certain embodiments, the invention is directed to a method for treating a protein folding disorder comprising administering an effective amount of a compound or pharmaceutical composition as disclosed herein to a patient in need thereof.

Preferred doses of the compounds of the present invention are 0.01-500 mg/kg of body weight per day, more preferably 0.01-50 mg/kg of body weight per day, and still more preferably 0.05-50 mg/kg of body weight per day.

In certain embodiments, the present invention is directed to a method for treating a protein folding disorder comprising administering a compound of any of formulas (I), (II), (III), (IV), (V), (VI), (VII), (VIII), (IX), (X), (XI), (XII), (XIII), (XIV), (XV), (XVI), (XVII) and (XVIII) as described above.

In certain embodiments, the compound of any of formulas (I), (II), (III), (IV), (V), (VI), (VII), (VIII), (IX), (X), (XI), (XII), (XIII), (XIV), (XV), (XVI), (XVII) and (XVIII) is dosed, e.g., at a dose of 0.01-500 mg/kg of body weight per day, more preferably 0.01-50 mg/kg of body weight per day, and still more preferably 0.05-50 mg/kg of body weight per day.

In certain embodiments of the present invention, the protein folding disorder being treated is a neurodegenerative disease.

In certain embodiments of the present invention, the neurodegenerative disease is selected from the group consisting of tauopathies, cerebral amyloid angiopathy, Lewy body diseases, Alzheimer's disease, dementia, Huntington's disease, Parkinson's disease, prion-based spongiform encephalopathy and a combination thereof In certain embodiments, the present invention is directed to a method for inhibiting tau protein aggregation comprising administering to a subject a compound of formula (I), (II), (III), (IV), (V), (VI), (VII), (VIII), (IX), (X), (XI), (XII), (XIII), (XIV), (XV), (XVI), (XVII) and (XVIII) as disclosed herein, or a pharmaceutically acceptable salt thereof.

In certain embodiments, the present invention is directed to a method for inhibiting Aβ protein aggregation comprising administering to a subject a compound of formula (I), (II), (III), (IV), (V), (VI), (VII), (VIII), (IX), (X), (XI), (XII), (XIII), (XIV), (XV), (XVI), (XVII) and (XVIII), as disclosed herein, or a pharmaceutically acceptable salt thereof In certain embodiments, the present invention is directed to a method for inhibiting α-synuclein protein aggregation comprising administering to a subject a compound of formula (I), (II), (III), (IV), (V), (VI), (VII), (VIII), (IX), (X), (XI), (XII), (XIII), (XIV), (XV), (XVI), (XVII) and (XVIII) as disclosed herein, or a pharmaceutically acceptable salt thereof In certain embodiments of the disclosed method, the neurodegenerative disease is selected from the group consisting of tauopathies, cerebral amyloid angiopathy, Lewy body diseases (e.g. Parkinson's disease), Alzheimer's disease, dementia, Huntington's disease, prion-based spongiform encephalopathy and a combination thereof.

In certain embodiments of the disclosed method, the neurodegenerative disease is Alzheimer's disease.

Compositions

In certain embodiments, the present invention is directed to a pharmaceutical composition comprising a pharmaceutically acceptable excipient(s) and an effective amount of a compound of formula (I), (II), (III), (IV), (V), (VI), (VII), (VIII), (IX), (X), (XI), (XII), (XIII), (XIV), (XV), (XVI), (XVII) and (XVIII) to treat a protein folding disorder, e.g., a neurodegenerative disease such as, tauopathies, cerebral amyloid angiopathy, Lewy body diseases (e.g. Parkinson's disease), Alzheimer's disease, dementia, Huntington's disease, prion-based spongiform encephalopathy and a combination thereof.

In certain embodiments, the present invention is directed to a pharmaceutical composition comprising a pharmaceutically acceptable excipient and an effective amount of a compound of formula (I), (II), (III), (IV), (V), (VI), (VII), (VIII), (IX), (X), (XI), (XII), (XIII), (XIV), (XV), (XVI), (XVII) and (XVIII) to treat systemic amyloidoses, particularly those affecting the peripheral nerves, spleen and pancreas.

Various oral dosage forms can be used, including such solid forms as tablets, gelcaps, capsules, caplets, granules, lozenges and bulk powders and liquid forms such as, e.g., emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered.

Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents.

Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by in-corporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986). Techniques and compositions for making solid oral dosage forms are described in *Pharmaceutical Dosage Forms: Tablets* (Lieberman, Lachman and Schwartz, editors) 2nd edition, published by Marcel Dekker, Inc. Techniques and compositions for making tablets (compressed and molded), capsules (hard and soft gelatin) and pills are also described in *Remington's Pharmaceutical Sciences* (Arthur Osol, editor), 1553B1593 (1980). Techniques and composition for making liquid oral dosage forms are described in *Pharmaceutical Dosage Forms: Disperse Systems*, (Lieberman, Rieger and Banker, editors) published by Marcel Dekker, Inc.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as, e.g., stabilizing agents, suspending agents, dispersing agents, and the like. The compounds of the invention may also be in the form of a powder for reconstitution as an injectable formulation. The compounds of the present invention may also be, e.g., in the form of an isotonic sterile solution.

In an aqueous composition, preferred concentrations for the active compound are 10 M-500 mM, more preferably 10 M-100 mM, still more preferably 10 M-50 mM, and still more preferably 100 M-50 mM.

The compounds and compositions of the invention can be enclosed in multiple or single dose containers. The enclosed compounds and compositions can be provided in kits, for example, including component parts that can be assembled for use. The kit can also optionally include instructions for use in any medium. For example, the instructions can be in paper or electronic form. For example, a compound of the present invention in lyophilized form and a suitable diluent may be provided as separated components for combination prior to use. A kit may include a compound of the present invention and a second therapeutic agent for co-administration. The compound of the present invention and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

When treating or preventing these diseases, the compounds of the invention can either be used individually or in combination. For example, administration may be orally, topically, by suppository, inhalation, subcutaneously, intravenously, bucally, sublingually, or parenterally.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The compounds of the invention can be used in combination, with each other or with other therapeutic agents or approaches used to treat or prevent the protein folding conditions described above. Such agents include, for example, cholinesterase inhibitors (such as, e.g., acetylcholinesterase inhibitors and butyrylcholinesterase inhibitors); gamma-secretase inhibitors/modulators; beta-secretase inhibitors; anti-inflammatory agents; anti-oxidants; immunological approaches; NMDA antagonists; cholesterol lowering agents (such as, e.g., statins); and direct or indirect neurotropic agents.

Acetylcholinesterase inhibitors include compounds such as, e.g., tacrine (tetrahydroaminoacridine, marketed as Cognex®), donepezil hydrochloride, (marketed as Aricept®), rivastigmine (marketed as Exelon®) and galantamine (Reminyl®).

Anti-oxidants include compounds such as, e.g., tocopherol, ascorbic acid, beta carotene, lipoic acid, selenium, glutathione, cysteine, coenzyme Q, vitamin E and ginkolides.

NMDA (N-methyl-D-aspartate) antagonists include, for example, memantine (Namenda®).

Immunological approaches include, for example, immunization with beta-amyloid peptides (or fragments thereof) or administration of anti-beta-amyloid antibodies.

Direct or indirect neurotropics agents include, for example, Cerebrolysin® and AIT-082 (Emilieu, 2000, Arch. Neurol. 57:454).

Anti-inflammatory agents include, for example, Cox-II inhibitors such as, e.g., rofecoxib, celecoxib, DUP-697, flosulide, meloxicam, 6-MNA, L-745337, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib and pharmaceutically acceptable salts thereof. Other anti-inflammatory agents include, for example, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam, isoxicam and pharmaceutically acceptable salts thereof.

Statins include, for example, atorvastatin, simvastatin, pravastatin, cerivastatin, mevastatin, velostatin, fluvastatin, lovastatin, dalvastatin, rosuvastatin, fluindostatin, dalvastain and pharmaceutically acceptable salts thereof Other cholesterol reducing compounds include bile sequestration compounds (e.g., colestipol and cholestyramine); fibrin (e.g., gemfibrozil, fenofibrate, psyllium, wheat bran, oat bran, rice bran, corn bran, konjak flour, Jerusalem artichoke flour, fruit fiber and any other functional food products) and other agents such as, e.g., nicotinic acid (niacin).

In addition, the compounds of the invention can also be used with inhibitors of P-glycoprotein (P-gp). The use of P-gp inhibitors is known to those skilled in the art. See for example, Cancer Research, 53, 4595-4602 (1993), Clin. Cancer Res., 2, 7-12 (1996), Cancer Research, 56, 4171-4179 (1996), International Publications WO99/64001 and WO01/10387. P-gp inhibitors are useful by inhibiting P-gp from decreasing brain blood levels of the compounds of the invention. Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as, e.g., GF120918, FK506, VX-710, LY335979, PSC-833, GF-102,918 and other steroids.

All of the additional agents disclosed above may be administered at the same or different time and/or route of administration than the compounds of the present invention.

The following examples illustrate various aspects of the present invention, and are not to be construed to limit the claims in any manner whatsoever.

DETAILED DESCRIPTION OF PREFERRED EMBODIMENTS

EXAMPLE 1

Preparation by Suzuki-Coupling Reaction

Compounds QR-0159, QR-0160, and QR-0162 were prepared by Suzuki-coupling reaction. The synthesis reaction is depicted in Scheme 1 below (Ts is para-toluene sulfonic acid).

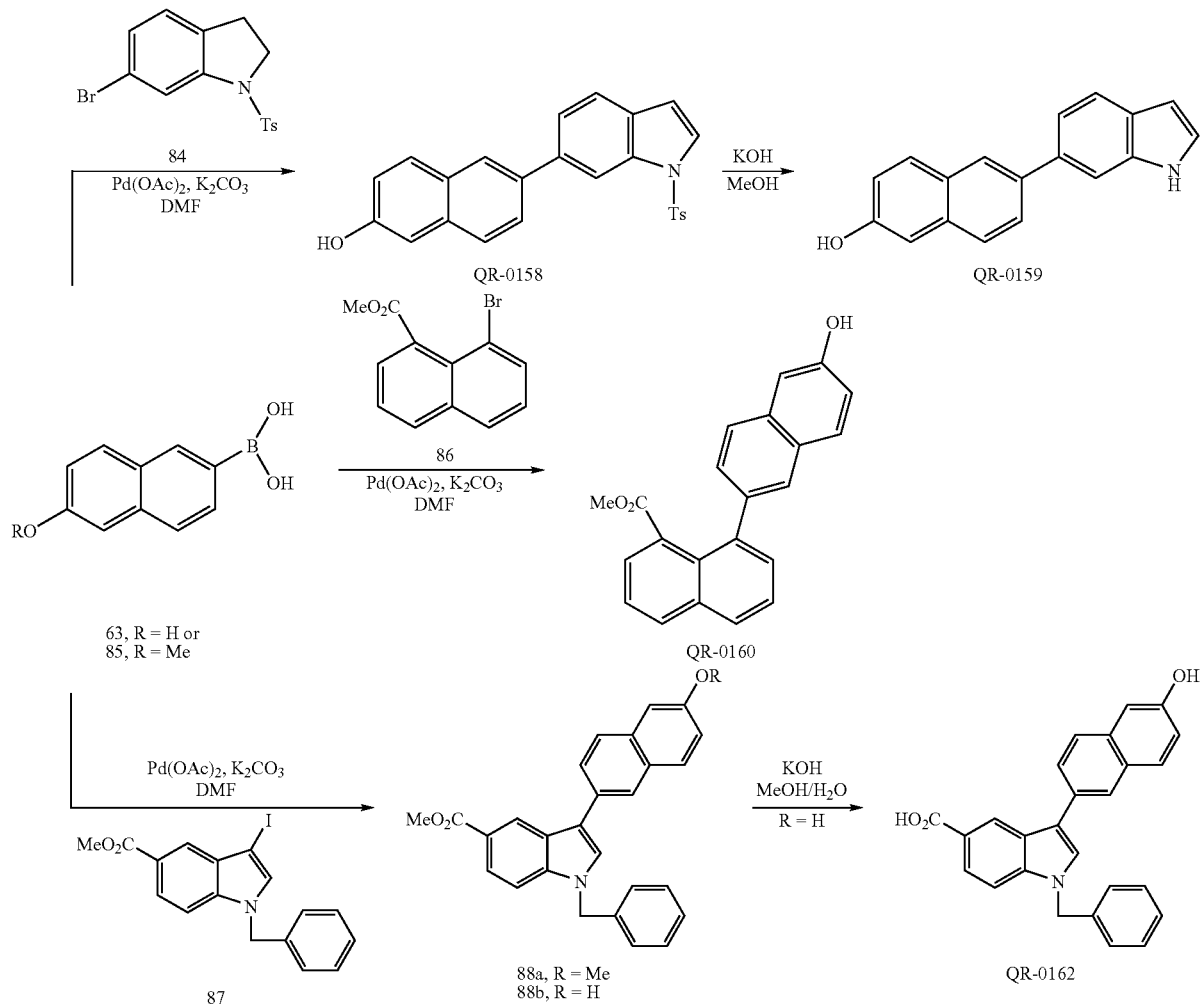

The following general procedure was used.

General Procedure for Suzuki-Coupling Reaction

To a degassed solution of the aryl halide (84, 86, 87 or 90, Schemes 1 and 2) in DMF (4.0-6.0 mL) was added aryl boronic acid (53, 55, 63 or 85, 1.2 equiv.), $Pd(OAc)_2$ (0.05 equiv.) and $K_2CO_3$ (2 equiv.) at room temperature. After degassing and purging with argon (done thrice), the reaction mixture was stirred at 90° C. Reaction times varied from 1.5 hours to 12 hours. The mixture was allowed to cool to room temperature and diluted with $H_2O$ (15 mL). The aqueous solution was extracted with ethyl acetate (5×15 mL) and the combined organic layer was concentrated under reduced pressure.

The residue was purified by flash column chromatography to yield the following compounds.

6-[1-(Toluene-4-sulfonyl)-indol-6-yl)-nathalen-2-ol (QR-0158). Beige solid. 40% Yield. $^1H$ NMR ($CDCl_3$) 6.69 (1H, d, J=3.6), 7.16 (1H, dd, J=2.4, 8.7), 7.19-7.25 (3H, m), 7.55-7.63 (3H, m), 7.72-7.81 (4H, m), 7.84 (1H, d, J=8.8), 8.02 (1H, s), 8.31 (1H, s).

6-(Indol-6-yl)-naphthalen-2-ol (QR-0159). White solid. 83% Yield.

$^1H$ NMR (DMSO) 6.47 (1H, s), 7.12 (1H, dd, J=2.3, 8.7), 7.16 (1H, s), 7.40 (1H, t, J=2.7), 7.43 (1H, dd, J=1.3, 8.2), 7.65 (1H, d, J=8.2), 7.76 (1H, d, J=13.5), 7.79 (1H, s), 7.87 (1H d, J=6.9), 8.07 (1H, s), 9.72 (1H, s), 11.16 (1H, s); $^{13}C$ NMR 101.44, 108.95, 109.80, 118.86, 119.39, 120.91, 125.17, 126.21, 126.51, 127.04, 127.42, 128.68, 130.10, 133.89, 134.02, 136.37, 137.13, 155.67.

6'-Hydroxy-[1,2]'-binaphthalenyl-8-carboxylic acid methyl ester (QR-0160). White solid. 43% Yield. $^1H$ NMR ($CDCl_3$) 2.83 (3H, s), 7.11 (1H, dd, J=2.5, 8.8), 7.18 (1H, d, J=2.4), 7.52 (1H, t, J=7.3), 7.55-7.63 (3H, m), 7.68-7.78 (4H, m), 7.9 (1H, dd, J=1.9, 7.5), 8.30 (1H, d, J=7.3). HRMS: calculated for $C_{22}H_{16}O_3$ m/z $[M]^+$=328.1099, found $[M]^+$=328.1107.

1-Benzyl-3-(6-methoxynaphthalen-2-yl)-indole-5-carboxylic methyl ester (88a). White solid. 22% Yield. $^1$H NMR (acetone-$d_6$) 3.91 (3H, s), 3.96 (3H, s), 5.63 (2H, s), 6.90 (1H, s), 7.03 (2H, d, J=6.8), 7.19-7.31 (4H, m), 7.37 (1H, s), 7.46 (1H, d, J=8.2), 7.51 (1H, dd, J=1.0, 8.2), 7.80 (1H, d, J=8.7), 7.85 (1H, d, J=8.7), 7.89 (1H, d, J=8.2), 7.99 (1H, s), 8.41 (1H, s).

1-Benzyl-3-(6-hydroxynaphthalen-2-yl)-indole-5-carboxylic methyl ester (88b). White solid, 26% Yield. $^1$H NMR (CDCl$_3$) 3.94 (3H, s), 5.40 (2H, s), 6.77 (1H, s), 7.0 (2H, d, J=7.0), 7.13-7.30 (5H, m), 7.44 (1H, dd, J=1.4, 8.4), 7.61-7.67 (2H, m), 7.77 (1H, s), 7.87 (1H, dd, J=1.42, 8.6), 8.03 (1H, s), 8.44 (1H, s); $^{13}$C NMR (CDCl$_3$) 48.02, 51.96, 103.60, 109.40, 110.18, 118.96, 122.10, 123.26, 123.50, 125.99, 126.75, 127.30, 127.43, 128.0, 128.34, 128.45, 128.88, 130.03, 134.45, 137.73, 140.58, 143.62, 155.03, 168.47.

1-Benzyl-3-(6-hydroxynaphthalen-2-yl)-indole-5-carboxylic acid (QR-0162). White solid. 75% Yield. $^1$H NMR (DMSO) 5.58 (2H, s), 6.87 (1H, s), 6.92 (2H, d, J=7.4), 7.11-7.28 (5H, m), 7.49 (1H, d, J=8.7), 7.53 (1H, d, J=8.4), 7.72-7.80 (3H, m), 7.94 (1H, s), 8.31 (I H, s), 9.90 (1H, s), 12.47 (1H,s); $^{13}$C NMR 47.56, 103.90, 109.09, 111.04, 119.87, 122.98, 123.18 (2s), 126.38, 126.98, 127.23, 127.64, 127.88, 127.94, 128.47, 129.09, 130.27, 138.46, 140.49, 143.53, 156.59, 168.66; HRMS: calculated for $C_{26}H_{19}NO_3$ m/z [M]$^+$=393.1365, found [M]$^+$=393.1373.

EXAMPLE 2

Deprotection of O-methyl Groups

O-methyl groups were deprotected to give compounds QR-0164, QR-0165 and QR-0166. Their syntheses are depicted in Scheme 2 below.

The following general procedure was used.

General Procedure for Deprotection of O-Methyl Groups

To a solution of 91, 92, or 93 (Scheme 2) in CH$_2$Cl$_2$ at −78° C. BBr$_3$ (2-4 equiv.) was added dropwise. The reaction mixture was stirred at −78° C. for 15 minutes and warmed up gradually to room temperature. Reaction times varied from 2 hours to 12 hours. The reaction was quenched with water. The organic solvent was evaporated under reduced pressure. HCl (1.0 N, 3-5 ml) was added and the mixture was stirred at room temperature for 24 hours. The product was extracted from the aqueous solution using ethyl acetate (3×5.0 ml). The combined organic layer was dried (MgSO$_4$), filtered and concentrated under vacuum.

The residue was purified by flash chromatography to yield the following compounds.

2-(2,3-Dimethoxynaphthalen-1-yl)-benzofuran (91). White solid. 60% Yield. $^1$H NMR (CDCl$_3$) 3.82 (3H, s), 4.03 (3H, s), 7.01 (1H, s), 7.28-7.37 (4H, m), 7.42 (1H, t, J=7.0), 7.58 (1H, d, J=8.1), 7.69 (1H, d, J=6.9), 7.75 (1H, d, J=8.1), 7.82 (1H, d, J=8.5); $^{13}$C NMR (CDCl$_3$): 55.86, 61.66, 108.22, 109.03, 111.38, 120.93, 121.06, 122.79, 124.09, 124.72, 125.39, 125.61, 126.76, 128.38, 128.90, 131.15, 149.04, 151.04, 151.98, 155.12, 2-(2,3-Dihydroxynaphthalen-1-yl)-benzofuran (QR-0164). White solid. 72% Yield. $^1$H NMR (DMSO): 7.09 (1H, s), 7.21-7.37 (5H, m), 7.64 (2H, d, J=7.96), 7.69 (1H, d, J=7.9), 7.73 (1H, d, J=7.3), 9.35 (1H, s), 10.4 (1H, s); $^{13}$C NMR (DMSO): 108.28, 111.22, 111.49, 121.34, 123.22, 123.87, 124.23, 124.31, 124.38, 126.66, 128.14, 128.87, 129.15, 146.43, 147.0, 152.07, 152.07, 154.71; HRMS: calculated for $C_{18}H_{12}O_3$ m/z [M]$^+$=276.0786, found [M]$^+$=276.0789.

Scheme 2

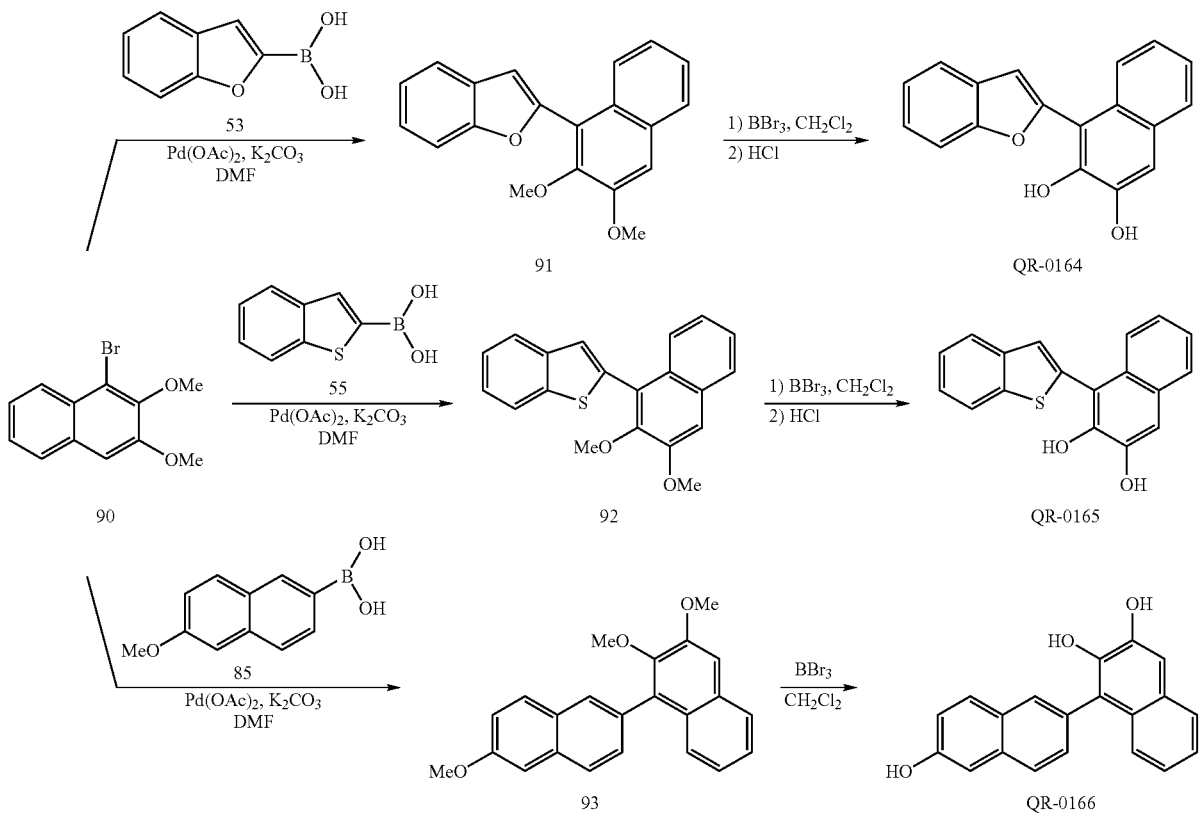

2-(2,3-Dimethoxynaphthalen-1-yl)-benzothiophene (92). White solid. 58% Yield. $^1$H NMR (acetone-$d_6$): 3.80 (s, 3H), 4.01 (3H, s), 7.34 (1H, t, J=7.6), 7.40-7.50 (4H, m), 7.55 (1H, s), 7.68 (1H, d, J=8.5), 7.88 (1H, d, J=8.2), 7.96 (1H, d, J=7.4), 8.15 (1H, d, J=7.7); $^{13}$C NMR (acetone-$d_6$): 55.26, 60.60, 108.68, 121.99, 123.62, 123.84, 124.29, 124.33, 124.38, 125.05, 125.38, 126.82, 128.80, 131.37, 137.05, 140.16, 140.80, 148.20, 152.25.

2-(2,3-Dihydroxynaphthalen-1-yl)-benzothiophene (QR-0165). White solid. 57% Yield. $^1$H NMR (DMSO): 7.16-7.30 (3H, m), 7.36-7.45 (3H, m), 7.52 (1H, d, J=8.3), 7.69 (1H, d, J=7.9), 7.92 (1H, d, J=7.3), 8.01 (1H, d, J=7.8); $^{13}$C NMR (DMSO): 110.48, 114.25, 122.60, 123.78, 123.97, 124.06, 124.14, 124.54, 124.68, 125.69, 126.52, 128.75, 128.88, 138.05, 140.38, 140.66, 145.99, 146.44. HRMS: calculated for $C_{18}H_{12}O_2S$ m/z $[M]^+$=292.0558, found $[M]^+$=292.0551.

2,3,6'-Trimethoxy-[1,2]'-binaphthalene (93), 51% Yield. $^1$H NMR (CDCl$_3$) 3.60 (3H, s), 3.97 (3H, s), 4.04 (3H, s), 7.16-7.26 (4H, m), 7.38 (1H, t, J=7.5), 7.45-7.50 (2H, m), 7.75-7.79 (2H, m), 7.80 (1H, s), 7.86 (1H, d, J=8.3).

2,3,6'Trihydroxy-[1,2]'-binaphthalene (QR-0166). Purple oil. 63% Yield. $^1$H NMR (acetone-$d_6$) 7.16 (1H, t, J=7.0), 7.20 (2H, m), 7.33 (2H, s), 7.38 (1H, d, J=8.3), 7.43 (1H, dd, J=1.5, 8.4), 7.82 (1H, d, J=8.1), 7.80-7.87 (3H, m); $^{13}$C NMR (acetone-$d_6$) 108.90, 118.52, 123.25, 123.29, 124.52, 126.20, 126.23, 128.67, 128.95, 129.49, 129.62, 129.81, 130.45, 134.37, 143.26, 145.81, 155.58, HRMS: calculated for $C_{20}H_{14}O_3$ m/z $[M]^+$=302.0943, found $[M]^+$=302.0947.

EXAMPLE 3

Preparation by Negishi Coupling Reaction

Compounds QR-0183, QR-0195, QR-0203, QR-0264, QR-0226, and QR-0262 were prepared by Negishi coupling reaction. Their syntheses are depicted in Scheme 3 and 5 below.

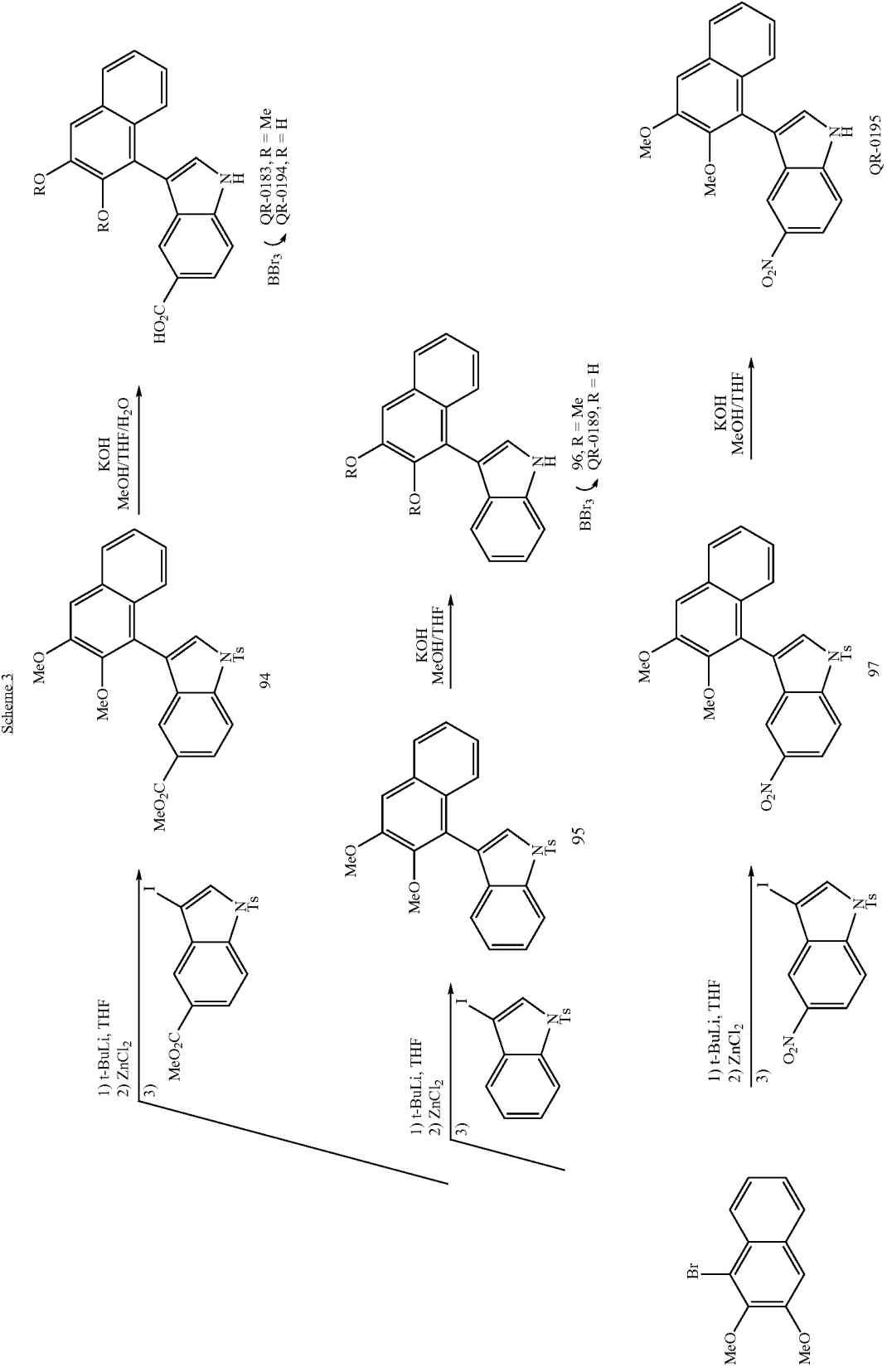

-continued
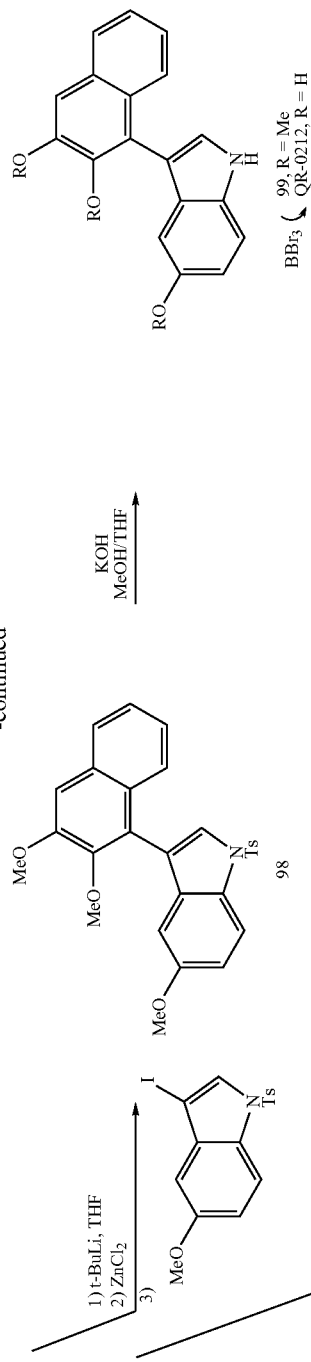
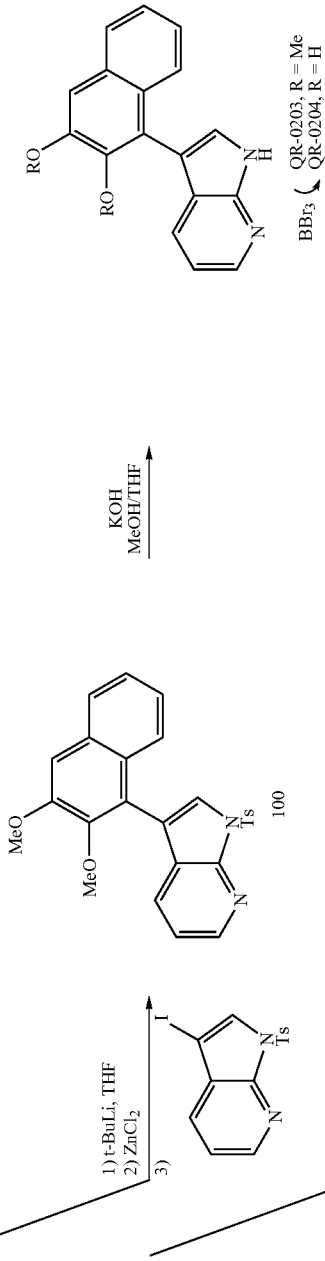
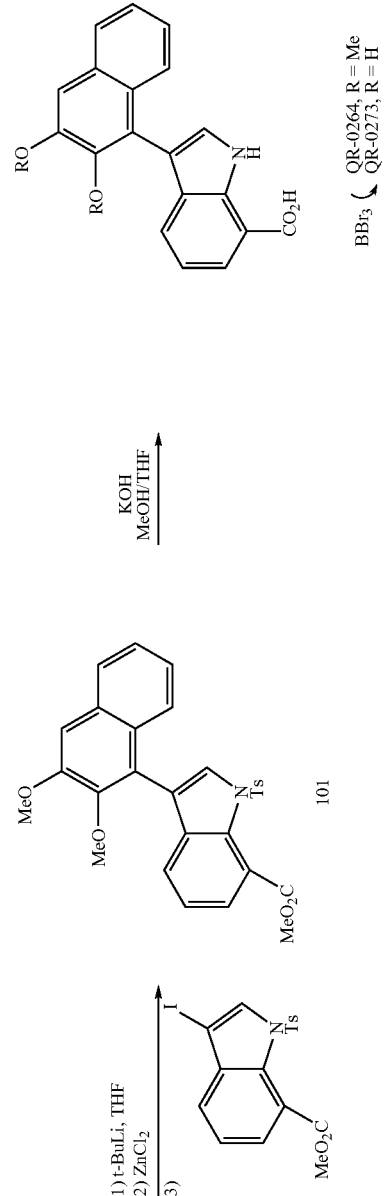

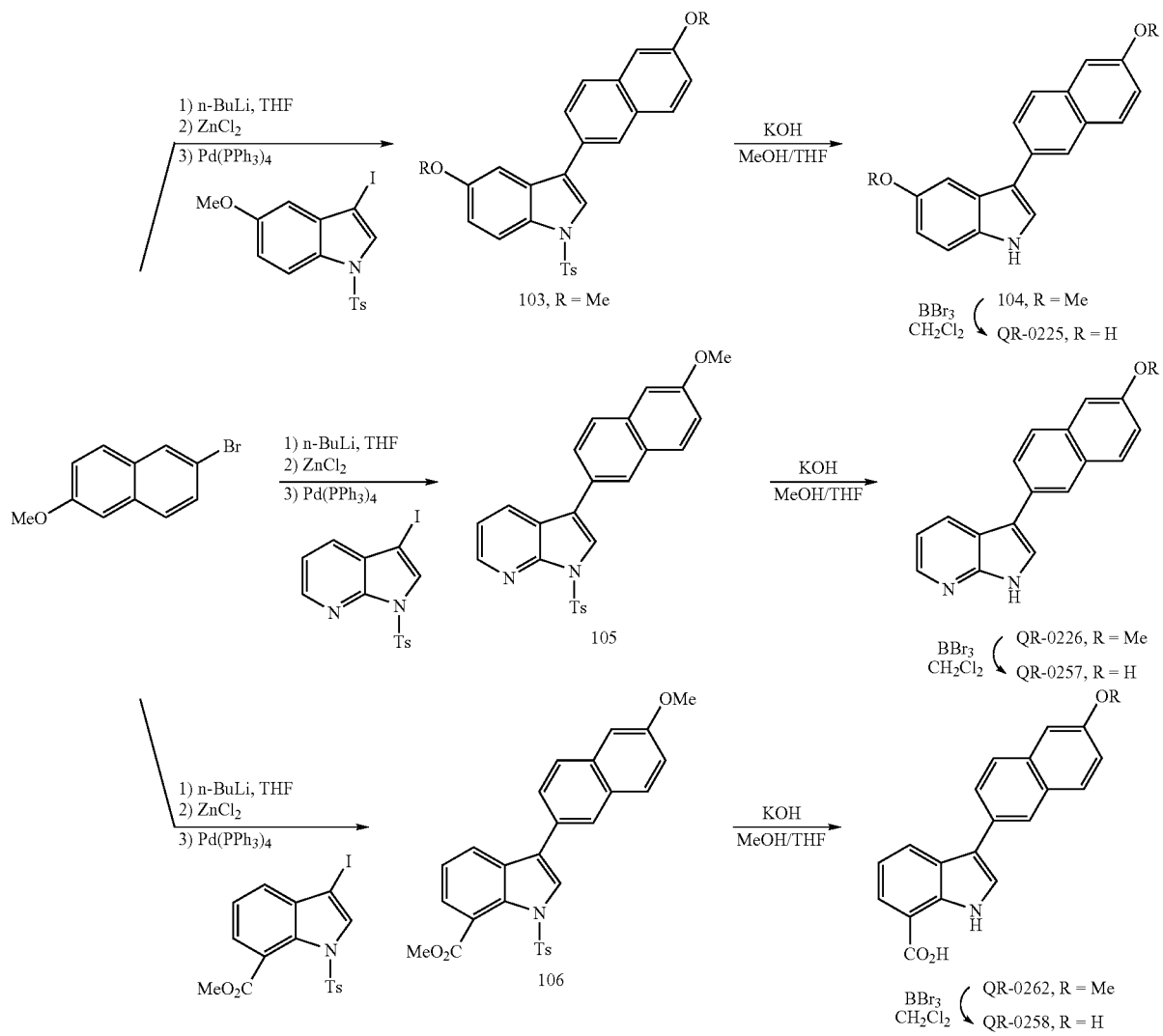

Scheme 5

The following general procedure was used:

General Procedure for Negishi Coupling Reaction

At −78° C., t-BuLi (1.5 equiv) or n-BuLi (1.5 equiv) was added to the solution of aryl halide (1 equiv) in THF. After stirring at −78° C. for 25 minutes, ZnCl$_2$ solution (1.0 M, 1.5 equiv) was added dropwise. The resulting solution was stirred for 25 minutes and at room temperature for 30 minutes (Solution A).

Solution A (3 equiv) was then added to the degassed solution of substituted 3-iodoindole (1 equiv) and Pd(PPh$_3$)$_4$ (0.05 equiv). The mixture was stirred at 65° C.-80° C. for 4-12 hours. After cooling to room temperature, the reaction was quenched with brine. The aqueous layer was extracted with ethyl acetate and the combined organic layer was dried (MgSO$_4$), filtered and concentrated under reduced pressure. The crude product was purified by flash chromatography to yield the following compounds.

Methyl 3-(2,3-dimethoxynathalen-1-yl)-1-tosyl-1H-indole-5-carboxylate, 94 (Scheme 3). White solid. 70% yield. $^1$H NMR (CDCl$_3$): 2.38 (3H, s), 3.46 (3H, s), 3.79 (3H, s), 4.04 (3H, s), 7.18 (1H, t, J=8.1), 7.24-7.32 (4H, m), 7.39 (1H, t, =7.0), 7.72 (1H, s), 7.77 (1H, d, J=8.1), 7.81-7.87 (3H, m), 8.04 (1H, dd, J=1.5, 8.8), 8.14 (1H, d, J=8.8); $^{13}$C NMR (CDCl$_3$): 29.63, 52.00, 55.79, 61.09, 107.95, 113.66, 118.14, 121.54, 123.22, 124.34, 125.22, 125.58, 125.82, 126.15, 126.82, 126.90, 127.19, 128.68, 130.02, 131.33, 131.56, 135.14, 137.71, 145.39, 152.14, 167.10.

3-(2,3-dimethoxynathalen-1-yl)-1-tosyl-1H-indole-5-carboxylic acid, QR-0183 (Scheme 3). White solid. 96% yield. $^1$H NMR (DMSO) 3.49 (3H, s), 4.00 (3H, s), 7.21 (1H, t, J=7.39), 7.38-7.43 (2H, m), 7.51 (1H, s), 7.57 (1H, d, J=8.53), 7.60 (1H, d, J=2.26), 7.69 (1H, s), 7.77 (1H, dd, J=8.57, 1.41), 7.88 (1H, d, J=7.93), 11.73 (1H, s,), 12.30 (1H, s); $^{13}$C NMR (DMSO) 56.10, 60.93, 107.67, 110.43, 111.95, 122.01, 122.33, 122.82, 124.20, 124.34, 125.57, 125.90, 127.24, 127.29, 127.91, 129.33, 131.51, 138.98, 148.07, 152.51, 168.72.

3-(2,3-dihydroxynathalen-1-yl)-1-tosyl-1H-indole-5-carboxylic acid, QR-0194 (Scheme 3). Beige solid. 77% yield. $^1$H NMR (DMSO) 7.09 (1H, t, J=6.9), 7.18-7.25 (2H, m), 7.37 (1H, d, J=8.41), 7.51 (1H, d, J=2.11), 7.55 (1H, d, J=8.50), 7.67 (1H, d, J=8.06), 7.72-7.78 (2H, m), 8.49 (1H, s, br), 10.05 (1H, s, br), 11.64 (1H, s); $^{13}$C NMR (DMSO) 109.07, 110.98, 111.76, 114.80, 121.61, 122.62, 122.90, 123.22, 123.33, 124.94, 126.42, 127.56, 127.85, 129.20, 129.36, 139.15, 145.35, 146.70, 168.84; HRMS: measured=319.0835, theoretical=319.0844.

3-(2,3-dimethoxynathalen-1-yl)-1-tosyl-1H-indole, 95 (Scheme 3). Yellow solid, 72% yield, $^1$H NMR (CDCl$_3$): 2.37 (3H, s), 3.44 (3H, s), 4.03 (3H, s), 7.10-7.20 (3H, m), 7.21-7.28 (3H, m, overlapped with CDCl$_3$), 7.32-7.41 (3H, m), 7.67 (1H, s), 7.75 (1H, d, J=8.12), 7.82 (2H, d, J=8.4), 8.11 (1H, d, J=8.4); $^{13}$C NMR (CDCl$_3$): 21.60, 55.76, 61.03, 107.61, 113.90, 117.64, 121.11, 123.51, 124.11, 124.79, 125.47, 125.56, 126.14, 126.74, 126.88, 128.67, 129.85, 131.30, 131.68, 135.19, 135.39, 144.92, 152.19.

3-(2,3-dihydroxynathalen-1-yl)-1-tosyl-1H-indole, QR-0189 (Scheme 3). Yellow solid, 40% yield, $^1$H NMR (DMSO): 6.93 (1H, t, J=7.6), 7.01-7.09 (2H, m), 7.12 (1H, t, J=7.6), 7.16-7.22 (2H, m), 7.37-7.42 (2H, m), 7.48 (1H, d, J=8.2), 7.63 (1H, d, J=8.1), 8.37 (1H, s), 9.98 (1H, s), 11.30 (1H, s); $^{13}$C NMR (DMSO): 108.78, 109.37, 111.99, 115.68, 119.01, 120.18, 121.25, 122.96, 123.21, 125.27, 126.06, 126.35, 128.20, 129.21, 129.39, 136.65, 145.15, 146.73.

3-(2,3-dimethoxynathalen-1-yl)-5-nitro-1-tosyl-1H-indole, 97 (Scheme 3), White solid. 67% yield. $^1$H NMR (CDCl$_3$): 2.40 (3H, s), 3.50 (3H, s), 4.05 (3H, s), 7.20 (1H, t, J=7.2), 7.27-7.34 (4H, m), 7.41 (1H, t, J=6.9), 7.79 (1H, d, J=7.9), 7.83 (1H, s), 7.85 (2H, d, J=8.6), 8.04 (1H, d, J=1.8), 8.18-8.28 (2H, m); $^{13}$C NMR (CDCl$_3$): 21.69, 55.82, 61.13, 108.38, 114.08, 117.50, 118.29, 120.06, 120.49, 124.56, 124.83, 125.73, 126.96, 127.03, 128.34, 128.70, 130.24, 130.54, 131.42, 131.65, 134.82, 137.96, 114.57, 145.94, 148.21.

3-(2,3-dimethoxynathalen-1-yl)-5-nitro-1H-indole, QR-0195 (Scheme 3). Yellow solid. 68% yield. $^1$H NMR (DMSO) 3.51 (3H, s), 4.02 (3H, s), 7.24 (1H, t, J=7.5), 7.39-7.47 (2H, m), 7.54 (1H, s), 7.71 (1H, d, J=9.0), 7.80 (1H, s), 7.90 (1H, d, J=8.1), 7.94 (1H, s), 8.06 (1H, d, J=8.95), 12.16 (1H, s); $^{13}$C NMR (DMSO) 56.15, 60.97, 108.09, 111.77, 112.85, 116.47, 117.06, 123.24, 124.46, 125.61, 125.70, 127.36, 127.54, 129.04, 129.82, 131.60.

5-methoxy-3-(2,3-dimethoxynathalen-1-yl)-1-tosyl-1H-indole, 98 (Scheme 3). Yellow solid. 99% yield. $^1$H NMR (CDCl$_3$): 2.41 (3H, s), 3.48 (3H, s), 3.66(3H, s), 4.08 (3H, s), 6.56 (1H, d, J=2.5), 7.0 (1H, dd, J=2.5, 9.1), 7.21 (1H, t, J=8.0), 7.25-7.33 (3H, m), 7.36 (1H, d, J=8.4), 7.43 (1H, t, J=8.0), 7.65 (1H, s), 7.80 (1H, d, J=8.1), 7.83 (2H, d, J=8.3), 8.04 (1H, d, J=9.0); $^{13}$C NMR (CDCl$_3$): 21.59, 55.60, 55.77, 61.04, 103.03, 107.59, 114.22, 114.89, 117.88, 122.25, 124.12, 125.51, 125.57, 126.71, 126.83, 126.96, 128.64, 129.79, 131.28, 132.77, 135.31, 144.81, 152.19, 156.74.

5-hydroxy-3-(2,3-dihydroxyynathalen-1-yl)-1H-indole, QR-0212 (Scheme 3). Gray solid. 89% yield. $^1$H NMR (DMSO) 6.38 (1H, d, J=), 6.64 (1H, dd, J=2.3, 8.6), 7.08 (1H, t, J=7.1), 7.16-7.23 (2H, m) 7.25-7.30 (2H, m), 7.41 (1H, d, J=8.43), 7.64 (1H, d, J=8.0), 8.28 (1H, s), 8.47 (1H, s), 9.91 (1H, s), 10.98 (1H, s); $^{13}$C NMR (DMSO) 104.06, 108.42, 108.64, 112.25, 116.04, 122.92, 123.18, 125.46, 126.31, 126.45, 128.99, 129.20, 129.31, 131.17, 145.0, 146.74, 150.91; HRMS: measured=291.0894, theoretical=291.0895.

3-(2,3-dimethoxynaphthalen-1-yl)-1-tosyl-1H-pyrrolo[2,3-b]pyridine, 100 (Scheme 3). White solid. 87% yield. $^1$H NMR (DMSO) 2.41 (3H, s), 3.58 (3H, s), 4.03 (3H, s), 7.26-7.36 (3H, m), 7.46 (1H, t, J=6.77), 7.48-7.55 (3H, m), 7.60 (1H, s), 7.93 (1H, d, J=8.15), 8.06-8.13 (3H, m), 8.46 (1H, dd, J=1.21, 4.65); $^{13}$C NMR (DMSO) 21.63, 56.24, 61.22, 108.86, 114.22, 120.09, 121.28, 123.78, 124.88, 125.09, 125.91, 126.39, 127.49, 128.07, 128.41, 129.72, 130.60, 131.57, 135.15, 145.46, 146.19, 147.16, 148.23, 152.32.

3-(2,3-dimethoxynaphthalen-1-yl)-1H-pyrrolo[2,3-b]pyridine , QR-0203 (Scheme 3). Yellow solid. 85% yield. $^1$H NMR (DMSO) 3.51 (3H, s), 3.99 (3H, s), 7.03 (1H, dd, J=4.6, 7.9), 7.24 (1H, t, J=7.24), 7.40 (1H, t, J=7.7), 7.44-7.51 (3H, m), 7.62 (1H, d, J=2.4), 7.86 (1H, d, J=8.1), 8.28 (1H, dd, J=1.2, 4.6), 11.98 (1H, s); $^{13}$C NMR (DMSO) 56.08, 60.87, 107.62, 107.81, 116.05, 120.46, 124.22, 124.26, 125.55, 125.84, 126.39, 127.26, 127.85, 129.21, 131.55, 143.10, 148.00, 148.93, 152.51.

3-(2,3-dihydroxynaphthalen-1-yl)-1H-pyrrolo[2,3-b]pyridine, QR-0204 (Scheme 3). Beige solid. 65% yield. $^1$H NMR (MeOD): 7.04-7.10 (2H, m), 7.17-7.23 (2H, m), 7.43 (1H, d, J=8.4), 7.48 (1H, s), 7.59-7.64 (2H, m), 8.22 (1H, dd, J=1.3, 4.8); $^{13}$C NMR (DMSO): 108.98, 114.81, 115.74, 120.45, 123.26, 123.33, 124.90, 126.47, 126.65, 128.22, 129.18, 129.23, 142.80, 145.28, 146.64, 146.72, 149.11.

Methyl 3-(2,3-dimethoxynathalen-1-yl)-1-tosyl-1H-indole-7-carboxylate, 101 (Scheme 3). White solid. 65% yield. $^1$H NMR (CDCl$_3$): 2.36 (3H, s), 3.36 (3H, s), 4.00 (3H, s), 4.05 (3H, s), 6.91 (1H, d, J=8.4), 7.06 (1H, t, J=7.4), 7.13-7.26 (5H,), 7.36 (1H, t, J=7.4), 7.52 (1H, s), 7.57-7.63 (3H, m), 7.73 (1H, d, J=8.1); $^{13}$C NMR (CDCl$_3$): 21.61, 52.70, 55.74, 61.02, 107.84, 120.63, 121.28, 123.20, 123.83, 124.07, 124.24, 125.13, 125.50, 126.11, 126.75, 127.10, 128.36, 129.36, 129.62, 131.28, 132.53, 134.11, 134.79, 144.86, 148.50, 152.09, 169.15.

3-(2,3-dimethoxynathalen-1-yl)-1-tosyl-1H-indole-7-carboxylic acid, QR-0264 (Scheme 3). Light brown solid. 92% yield. $^1$H NMR (DMSO): 3.50 (3H, s), 4.0 (3H, s), 7.06 (1H, T, J=7.6), 7.20 (1H, t, J=8.1), 7.28 (1H, d, J=7.8), 7.37-7.43 (2H, m), 7.45-7.51 (2H, m), 7.81 (1H, d, J=7.4), 7.86 (1H, d, J=8.5), 11.35 (1H, s), 13.05 (1H, s); $^{13}$C NMR (DMSO): 56.07, 60.91, 107.65, 109.49, 114.31, 119.08, 124.15, 124.37, 124.50, 124.57, 125.21, 125.52, 125.92, 127.23, 129.36, 129.85, 131.52, 135.19, 148.09, 152.52, 168.36.

3-(2,3-dihydroxynathalen-1-yl)-1-tosyl-1H-indole-7-carboxylic acid, QR-0273 (Scheme 3). Yellow solid. 20% yield. $^1$H NMR (DMSO): 7.03-7.11 (2H, m), 7.18-7.23 (2H, m), 7.30 (1H, d, J=7.8), 7.36 (1H, d, J=8.4), 7.40 (1H, d, J=2.3), 7.65 (1H, d, J=8.0), 7.79 (1H, d, J=7.4), 8.48 (1H, s), 10.03 (1H, s), 11.25 (1H, s), 13.00 (1H, s); $^{13}$C NMR (DMSO): 109.04, 109.94, 114.17, 114.86, 118.69, 123.17, 123.30, 124.26, 124.96, 125.67, 126.43, 127.54, 129.23, 129.32, 129.78, 135.40, 145.33, 146.73, 168.50.

5-Methoxy-3-(2-methoxynaphthalen-6-yl)-1-tosyl-1H-indole, 103 (Scheme 5). Light yellow solid. 70% yield. $^1$H NMR (acetone-d$_6$): 2.37 (3H, s), 3.86 (3H, s), 3.97 (3H, s), 7.07 (1H, dd, J=2.5, 9.0), 7.22 (1H, dd, J=2.5, 8.9), 7.36-7.43 (4H, m), 7.81 (1H, dd, J=1.7, 8.5), 7.91-7.98 (5H, m) 8.03 (1H, d, J=9.0), 8.18 (1H, s), $^{13}$C NMR (acetone-d$_6$): 20.53, 54.81, 55.06, 103.06, 105.75, 113.82, 114.13, 114.75, 119.14, 124.22, 126.14, 126.48, 126.98, 127.49, 128.20, 129.27, 129.56, 130.04, 130.24, 130.43, 134.17, 135.07, 145.47, 157.12, 158.12.

5-Methoxy-3-(2-methoxynaphthalen-6-yl)-1H-indole 104 (Scheme 5). Light yellow solid. 95% yield. $^1$H NMR (DMSO): 3.83 (3H, s), 3.90 (3H, s), 6.85 (1H, dd, J=2.3, 8.8), 7.17 (1H, dd, J=2.5, 8.9), 7.32 (1H, d, J=2.3), 7.38 (1H, d, J=8.8), 7.44 (1H, d, J=2.2), 7.73 (1H, d, J=2.4), 7.80-7.94 (3H, m), 8.11 (1H, s); $^{13}$C NMR (DMSO) 55.65, 55.96, 101.75, 106.36, 111.90, 113.07, 115.94, 119.03, 123.93, 124.74, 125.86, 126.84, 127.56, 129.63, 129.68, 131.80, 132.63, 132.82.

5-Hydroxy-3-(2-hydroxynaphthalen-6-yl)-1H-indole QR-0225 (Scheme 5). Yellow solid. 66% yield. $^1$H NMR (DMSO) 6.70 (1H, dd, J=2.1, 8.6), 7.06-7.14 (2H, m), 7.26 (1H, d, J=8.6), 7.32(1H, d, J=1.99), 7.64 (1H, d, J=2.5), 7.72

(2H, s), 7.78 (1H, d, J=8.8), 7.98 (1H, s), 9.61 (1H, s), 11.05 (1H, s); $^{13}$C NMR 103.62, 109.15, 112.19, 112.74, 115.45, 119.20, 123.69, 124.22, 126.27, 126.62, 126.80, 129.44, 131.19, 131.94, 133.09, 151.75, 155.08.

3-(2-Methoxynaphthalen-6-yl)-1-tosyl-1H-pyrrolo[2,3-b]pyridine, 105 (Scheme 5). Yellow solid. 40% yield. $^1$H NMR (DMSO) 2.36 (3H, s), 3.91 (3H, s), 7.23 (1H, dd, J=2.4, 8.9), 7.31-7.48 (4H, m), 7.88-7.99 (3H, m), 8.08 (2H, d, J=8.3), 8.27-8.33 (2H, m), 8.44-8.51 (2H, m); $^{13}$C NMR (DMSO) 21.6, 55.7, 106.4, 119.5, 120.0, 120.2, 121.2, 123.7, 126.0, 126.4, 127.7, 128.0, 128.2, 129.2, 130.1, 130.2, 130.5, 134.1, 135.1, 145.5, 146.1, 158.0.

3-(2-Methoxynaphthalen-6-yl)-1H-pyrrolo[2,3-b]pyridine, QR-0226 (Scheme 5). Yellow solid. 76% yield. $^1$H NMR (DMSO) 3.90 (3H, s), 7.16-7.22 (2H, m), 7.34 (1H, d, J=2.3), 7.88 (2H, s), 7.92 (1H, d, J=8.9), 7.98 (1H, d, J=2.5), 8.19 (1H, s), 8.31 (1H, d, J=4.5), 8.47 (1H, d, J=7.9), 11.92 (1H, s); $^{13}$C NMR (DMSO): 55.66, 106.40, 114.76, 116.49, 117.86, 119.16, 124.02, 124.29, 126.37, 127.68, 128.27, 129.56, 129.74, 130.82, 133.08, 143.41, 149.65, 157.34.

3-(2-Hydroxynaphthalen-6-yl)-1H-pyrrolo[2,3-b]pyridine, QR-0257 (Scheme 5). Light yellow solid. $^1$H NMR (DMSO): 7.09 (1H, dd, J=2.36, 8.75), 7.13 (1H, d, J=2.19), 7.19 (1H, dd, J=4.6, 7.9), 7.74 (1H, d, J=8.6), 7.79 (1H, dd, J=1.7, 8.5), 7.85 (1H, d, J=8.8), 7.93 (1H, d, J=2.5), 8.12 (1H, s), 8.30 (1H, dd, J=1.4, 4.6), 8.43 (1H, d, J=7.9), 9.66 (1H, s), 11.88 (1H, s); $^{13}$C NMR (DMSO): 109.12, 114.94, 116.43, 117.89, 119.27, 124.05, 124.13, 126.20, 127.02, 128.22, 128.76, 129.75, 129.91, 133.43, 143.36, 149.64, 115.37.

Methyl 3-(2-methoxynaphthalen-6-yl)-1-tosyl-1H-indole-7-carboxylate, 106 (Scheme 5). White solid. 45% yield. $^1$H NMR (CDCl$_3$): 2.32 (3H, s), 3.95 (3H, s), 3.98 (3H, s), 7.14-7.21 (4H, m), 7.36 (1H, t, J=7.7), 7.54 (1H, dd, J=1.7, 8.4), 7.58 (1H, dd, J=1.0, 7.5), 7.61-7.65 (3H, m), 7.76 (1H, d, J=8.9), 7.80 (1H, d, J=8.5), 7.85-7.88 (2H, m); $^{13}$C NMR (CDCl$_3$): 21.60, 52.66, 55.40, 105.78, 119.50, 123.14, 124.18, 126.01, 126.50, 126.57, 126.60, 126.67, 126.96, 127.42, 127.49, 129.01, 129.49, 129.55, 132.08, 132.88, 134.12, 134.72, 144.88, 158.09, 169.00.

3-(2-Methoxynaphthalen-6-yl)-1H-indole-7-carboxylic acid, QR-0262 (Scheme 5). Yellow solid. 88% yield. $^1$H NMR (DMSO): 7.18 (1H, dd, J=2.5, 8.9), 7.26 (1H, t, J=7.69), 7.34 (1H, d, J=2.3), 7.76 (1H, d, J=2.4), 7.81-7.95 (4H, m), 8.17 (1H, s), 8.28 (1H, d, J=7.9), 11.32 (1H, s), 13.11 (1H, s); $^{13}$C NMR (DMSO): 55.67, 106.37, 114.41, 116.62, 119.16, 119.69, 124,71, 124.85, 125.31, 125.42, 127.02, 127.26, 127.68, 129.57, 129.77, 130.78, 122.14, 136.14, 136.08, 157.37, 168.34.

3-(2-Hydroxynaphthalen-6-yl)-1H-indole-7-carboxylic acid, QR-0258 (Scheme 5). Yellow-orange solid. 83% yield. $^1$H NMR (DMSO): 7.11 (1H, dd, J=2.4, 8.8), 7.14 (1H, d, J=2.3), 7.25 (1H, t, J=7.7), 7.73 (1H, d, J=2.5), 7.75 (2s, 2H), 7.85 (2H, d, J=8.5), 8.10 (1H, s), 8.25 (1H, d, J=7.9), 9.68 (1H, br), 11.29 (1H, s), 13.07 (1H, br); $^{13}$C NMR (DMSO): 109.08, 114.36, 116.78, 119.28, 119.62, 124.79, 124.82, 125.16, 125.20, 126.84, 127.02, 127.27, 128.77, 129.77, 129.88, 133.48, 136.09, 155.40, 168.45.

EXAMPLE 4

Preparation by Suzuki Coupling Reaction

Compounds 102, 107, 108, 109, 111, 112, 113, 114, 115, 116, 118, 119, 121, QR-0220, QR-0221, QR-0223, QR-0242, QR-0234 were synthesized by Suzuki coupling reaction. The reactions are depicted in Schemes 4, 6, 7, 8, 9, 10, and 11 below.

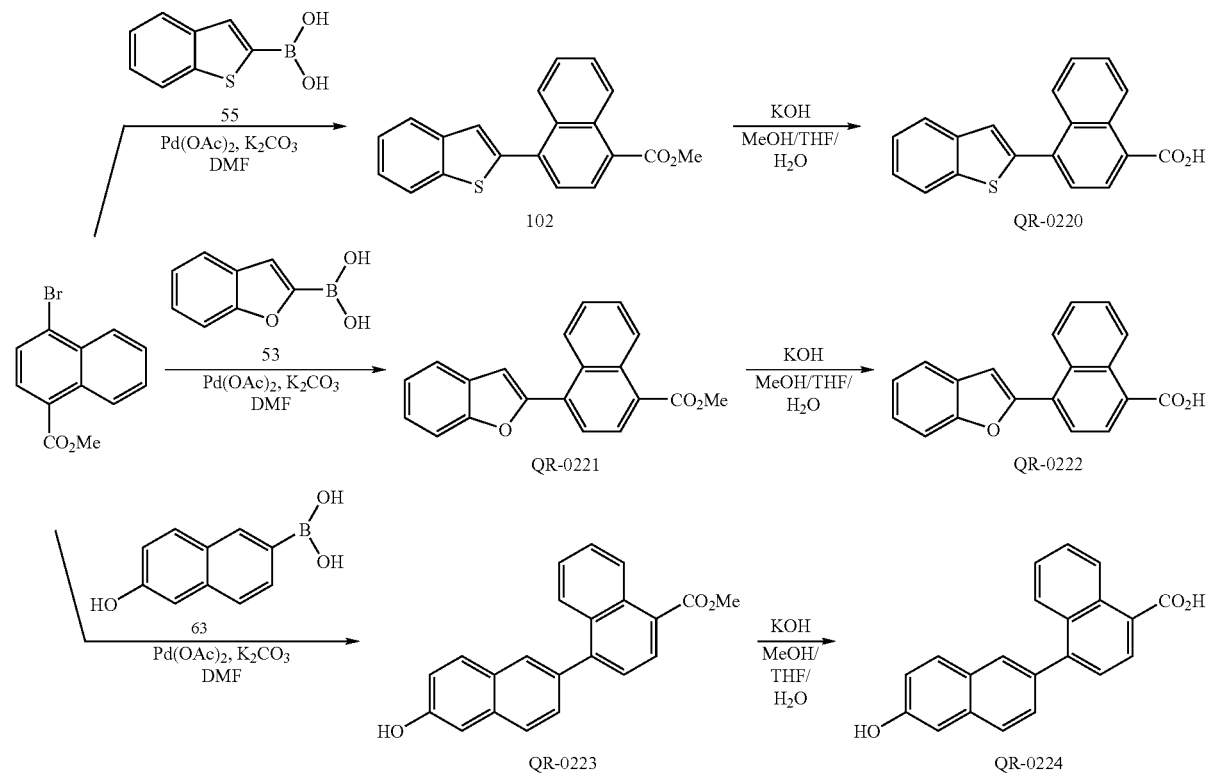

Scheme 4

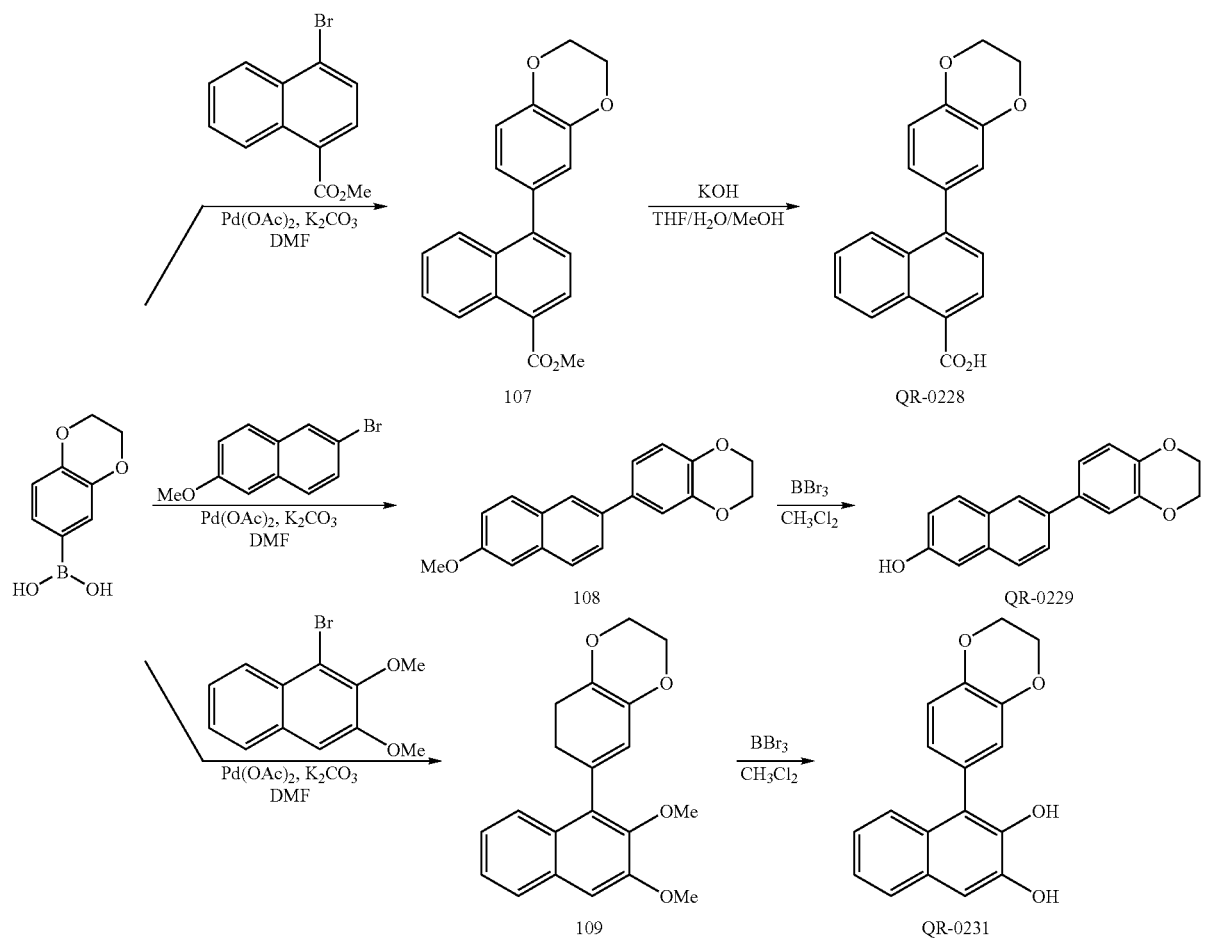

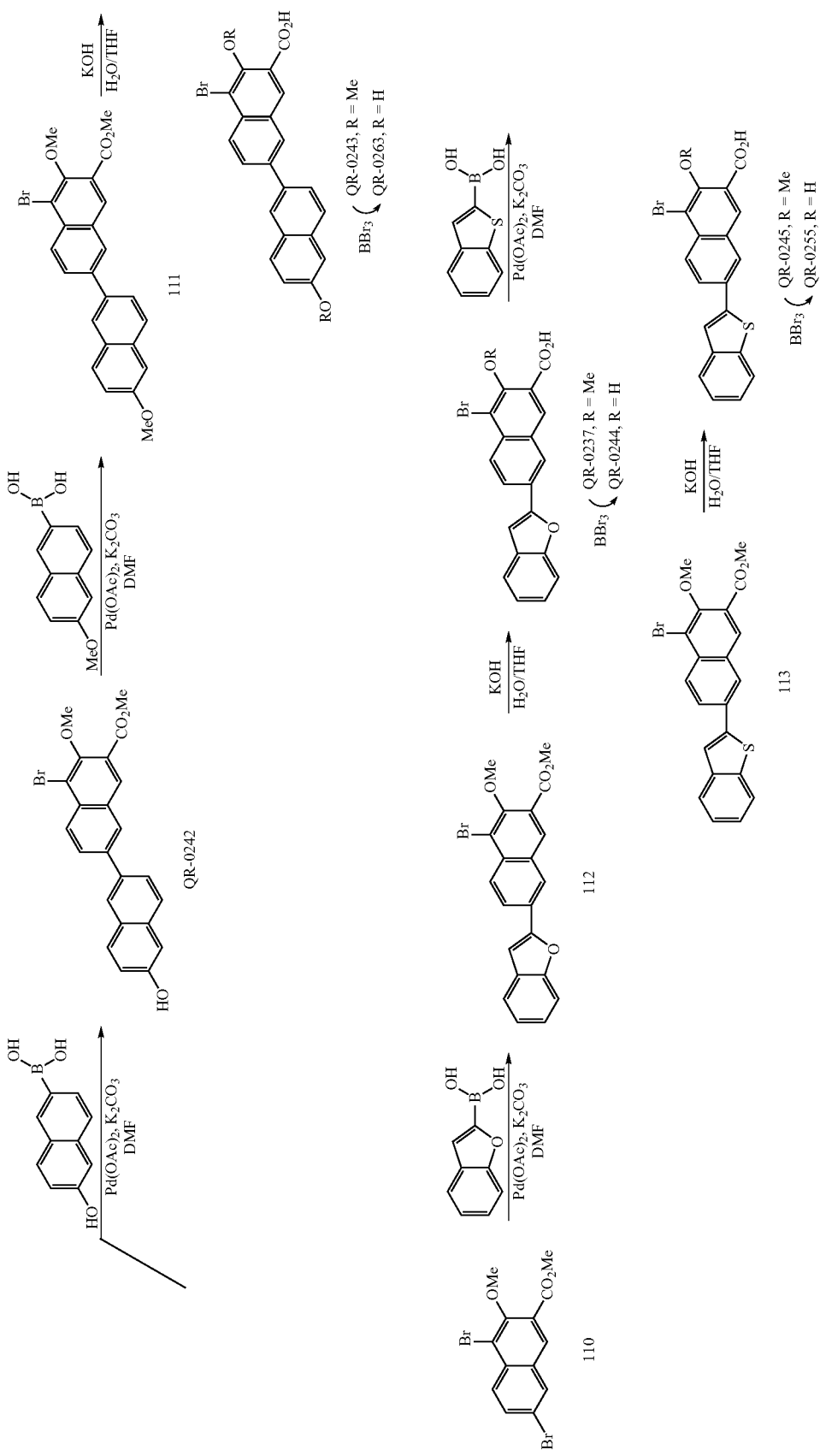

-continued
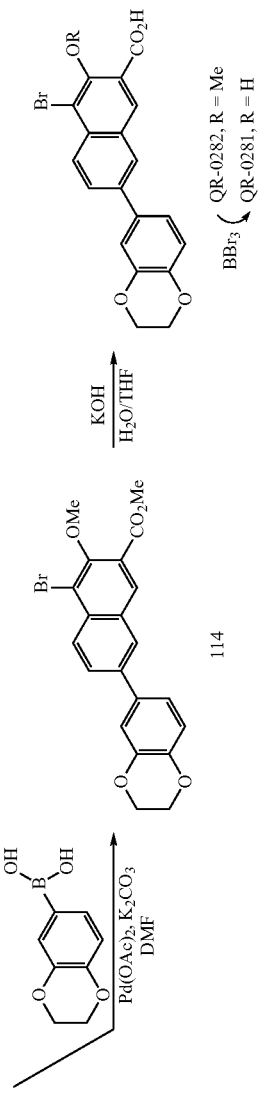

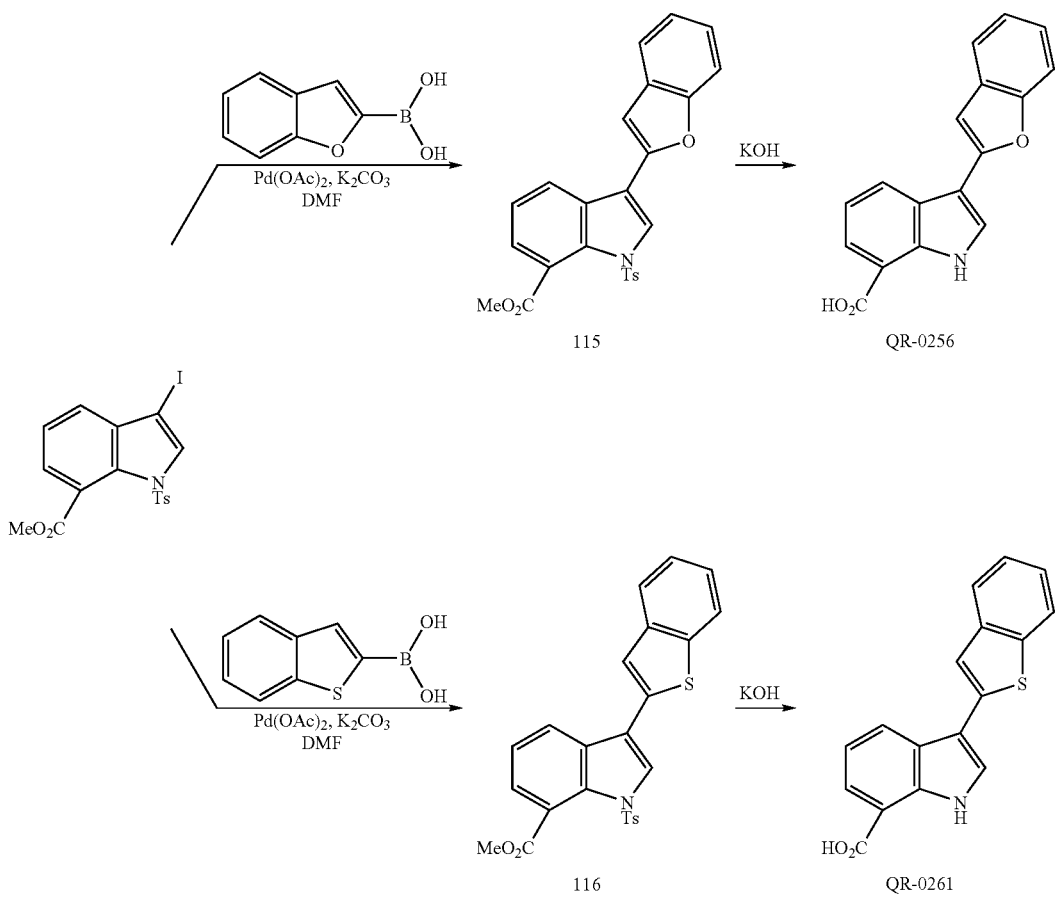
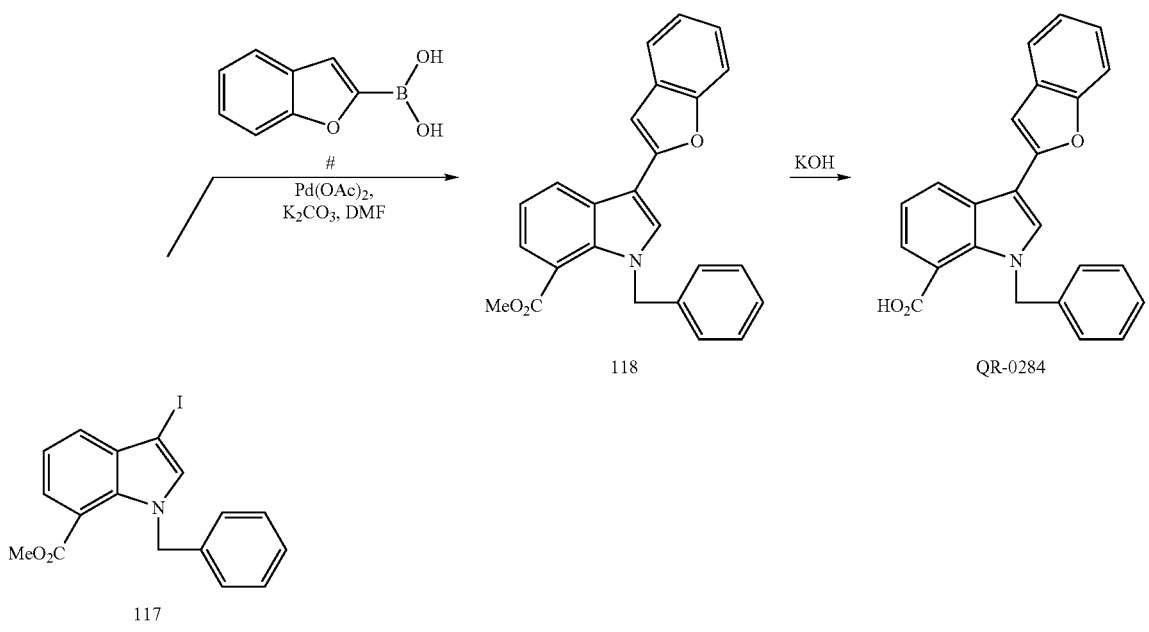

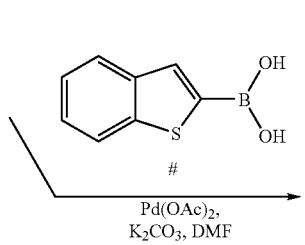
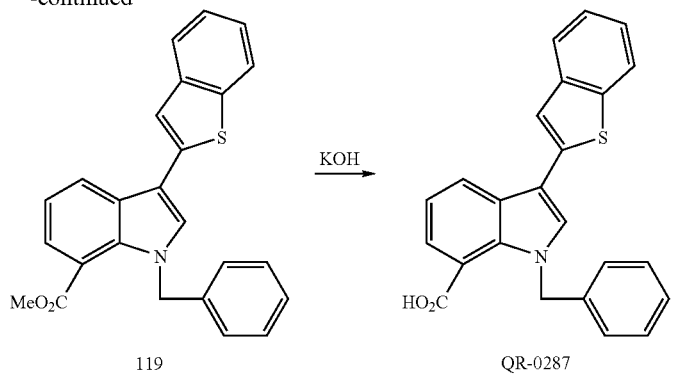

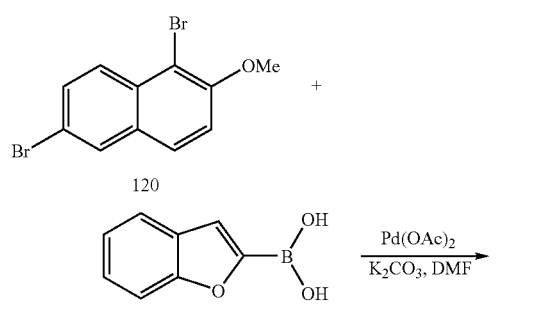
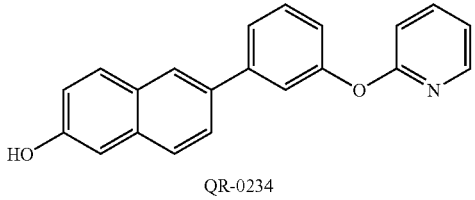

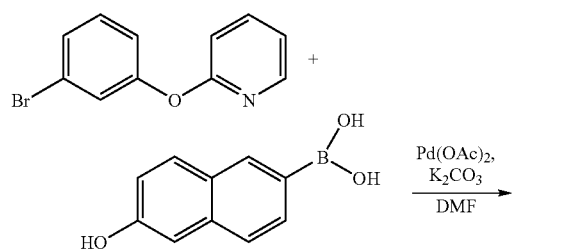

The following general procedure was followed. To a degassed solution of the aryl halide (1 equiv) in DMF was added aryl boronic acid (1.2 equiv.), $K_2CO_3$ (2 equiv.) and boronic acid (1.2 equiv.) at room temperature. After degassing and purging with argon (done thrice), the reaction mixture was stirred at 90° C. Reaction times varied from 2 hours to 12 hours. The reaction mixture was allowed to cool to room temperature and diluted with water. The aqueous layer was extracted with ethyl acetate several times, and the combined organic layer was dried ($MgSO_4$) and concentrated under reduced pressure.

The residue was purified by flash chromatography to yield the following compounds.

Methyl 4-benzo[b]thiophen-2-yl)naphthalene-1-carboxylate, 102 (Scheme 4). White solid. 95% yield. $^1$H NMR ($CDCl_3$): 4.04 (3H, s), 7.36-7.46 (2H, m), 7.48 (1H, s), 7.55 (1H, t, J=7.3), 7.62-7.69 (2H, m), 7.86 (1H, d, J=7.6), 7.90 (1H, d, J=7.9), 8.19 (1H, d, J=7.6), 8.33 (1H, d, J=8.4), 8.98 (1H, d, J=8.7); $^{13}$C NMR ($CDCl_3$): 52.33, 122.16, 123.84, 124.66, 124.70, 124.90, 126.15, 126.38, 126.83, 127.17, 127.63, 127.86, 129.21, 131.77, 132.29, 137.53, 140.05, 140.48, 141.21, 167.86.

4-benzo[b]thiophen-2-yl)naphthalene-1-carboxylic acid, QR-0220 (Scheme 4). White solid, 96% yield, $^1$H NMR (DMSO): 7.43-7.52 (2H, m), 7.67 (1H, t, J=7.6), 7.71-7.81 (3H, m), 7.98 (1H, d, J=7.3), 8.08 (1H, d, J=7.8), 8.20 (1H, d, J=7.5), 8.32 (1H, d, J=8.4), 8.96 (1, d, J=8.5); $^{13}$C NMR (DMSO): 122.81, 124.60, 125.39, 125.73, 126.26, 126.51, 127.64, 127.88, 128.28, 129.08, 129.39, 131.57, 131.82, 136.54, 140.08, 140.32, 140.67, 168.91.

Methyl 4-(benzofuran-2-yl)naphthalene-1-carboxylate, QR-0221 (Scheme 4). Light yellow solid, 97% yield, $^1$H NMR ($CDCl_3$): 4.04 (3H, s), 7.17 (1H, s), 7.31 (1H, t, J=7.9), 7.38 (1H, t, J=7.8), 7.58-7.72 (4H, m), 7.91 (1H, d, J=7.6), 8.23 (1H, d, J=7.6), 8.55 (1H, d, J=8.2), 8.99 (1H, d, J=8.2); $^{13}$C NMR ($CDCl_3$): 52.34, 107.55, 111.44, 111.71, 121.29, 123.21, 124.95, 125.78, 125.99, 126.31, 127.07, 127.81, 127.96, 128.83, 129.30, 131.07, 131.91, 132.92, 167.83.

4-(benzofuran-2-yl)naphthalene-1-carboxylic acid, QR-0222 (Scheme 4). Yellow solid. 82% yield, $^1$H NMR (DMSO) 7.36 (1H, t, J=7.2), 7.43 (1H, t, J=8.3), 7.52 (1H, s), 7.70-7.83 (4H, m), 8.03 (1H, d, J=7.6), 8.23 (1H, d, J=7.6), 8.55 (1H, d, J=7.72), 8.96 (1H, d, J=7.9), 13.34 (1H, s); $^{13}$C NMR (DMSO) 108.27, 111.84, 122.08, 123.89, 125.68, 126.12, 126.61, 127.87, 128.23, 128.95, 129.41, 129.50, 130.66, 131.64, 131.89, 154.29, 155.04, 168.89.

Methyl 4-(2-hydroxynaphthalene-6-yl)naphthalene-1-carboxylate, QR-0223 (Scheme 4). Light yellow solid, 85% yield, $^1$H NMR (CDCl$_3$) 4.04 (3H, s), 5.04 (1H, s), 7.18 (1H, dd, J=2.5), 7.23-7.28 (1H, overlapped with CDCl$_3$) 7.47 (1H, t, J=8.2), 7.52 (1H, d, J=7.5), 7.55 (1H, dd, J=1.7, 8.4), 7.63 (1H, t, J=7.0) 7.78-7.84 (2H, m), 7.87 (1H, s), 8.24 (1H, d, J=7.5), 9.00 (1H, d, J=8.6); $^{13}$C NMR (CDCl$_3$): 52.23, 109.48, 118.42, 125.97, 126.08, 126.28, 126.32, 126.51, 126.84, 127.54, 128.71, 128.75, 129.66, 130.17, 131.85, 132.33, 134.01, 135.50, 145.45, 153.89, 162.46.

4-(2-hydroxynaphthalene-6-yl)naphthalene-1-carboxylic acid, QR-0224 (Scheme 4). Yellow solid, 56% yield, $^1$H NMR (DMSO) 7.17 (1H, dd, J=2.2, 8.7), 7.24 (1H, d, J=1.98), 7.50-7.64 (3H, m), 7.69 (1H, t, J=7.0), 7.82-8.0 (4H, m), 8.23 (1H, d, J=7.5), 8.99 (1H, d, J=8.5), 9.87 (1H, s), 13.15 (1H, s); $^{13}$C NMR (DMSO) 109.07, 119.74, 126.40, 126.61, 126.78, 126.93, 127.52, 127.82, 128.06, 128.46, 128.85, 129.84, 130.25, 131.73, 132.04, 134.19, 134.50, 144.94, 156.37, 169.12.

Methyl 4-(2,3-dihydrobenzo[b][1,4]dioxin-7-yl)naphthalene-1-carboxylate, 107 (Scheme 6). White solid, 65% yield, $^1$H NMR (CDCl$_3$) 4.02 (3H, s), 4.34 (4H, s), 6.91-7.01 (3H, m), 7.41 (1H, d, J=7.5), 7.47 (1H, t, J=7.6), 7.61 (1H, t, J=7.7), 8.00 (1H, d, J=8.4), 8.17 (1H, d, J=7.5), 8.96 (1H, d, J=8.6); $^{13}$C NMR (CDCl$_3$) 52.17, 64.52, 117.20, 118.82, 123.14, 125.63, 125.98, 126.17, 126.29, 126.79, 127.47, 129.61, 131.81, 132.19, 133.50, 143.39, 144.88, 168.08.

2,3-Dihydro-6-(2-methoxynaphthalen-6-yl)benzo[b][1,4]dioxine, 108 (Scheme 6). White solid, 99% yield, $^1$H NMR (CDCl$_3$) 3.93 (3H, s), 4.31 (4H, s). 6.96 (1H, d=8.3), 7.12-7.23(4H, m), 7.64(1H, dd, J=7.78, 8.53), 7.72-7.79 (2H, m), 7.90 (1H, s); $^{13}$C NMR (CDCl$_3$) 55.36, 64.51, 105.63, 115.92, 117.63, 119.10, 120.25, 125.04, 125.85, 127.18, 129.23, 129.63, 133.57, 134.86, 135.83, 143.08, 143.80, 157.66.

2,3-Dihydro-6-(2,3-dimethoxynaphthalen-4-yl)benzo[b][1,4]dioxine, 109 (Scheme 6). Yellow solid, 80% yield, $^1$H NMR (CDCl$_3$) 3.66 (3H, s), 4.01 (3H, s), 4.38-4.45 (4H, m), 6.83 (1H, dd, J=1.9, 8.2), 6.90 (1H, d, J=1.9), 6.98 (1H, d, J=8.2), 7.19 (1H, s), 7.22 (1H, t, J=8.3), 7.37 (1H, t, J=7.9), 7.49 (1H, d, J=8.2), 7.72 (1H, d, J=8.0); $^{13}$C NMR (CDCl$_3$) 55.71, 61.60, 64.44, 64.48, 106.73, 116.95, 119.41, 123.81, 123.85, 125.18, 125.91, 126.52, 128.88, 129.15, 131.21, 131.60, 142.91, 143.23, 146.67, 152.22.

Methyl 4,7-dibromo-3-methoxynaphthalene-2-carboxylate, 110 (Scheme 7). Light yellow solid, $^1$H NMR (CDCl$_3$) 3.99 (3H, s), 4.00 (3H, s), 7.72 (1H, dd, J=1.92, 9.0), 8.04 (1H, s), 8.13 (1H, d, J=9.06), 8.24 (1H, s); $^{13}$C NMR (CDCl$_3$) 52.72, 62.26, 117.84, 120.58, 126.47, 128.77, 130.90, 131.20, 132.78, 133.36, 153.78, 165.47.

4-Bromo-7-(2-hydroxynaphthalen-6-yl)-3-methoxynaphthalene-2-carboxylic acid methyl ester, QR-0242 (Scheme 7). Yellow solid, $^1$H NMR (DMSO) 3.94 (3H, s), 3.96 (3H, s), 7.14-7.21 (2H, m), 7.83-7.95 (3H, m), 8.25-8.32 (3H, m), 8.58 (2H, s), 9.89 (1H, s).

4-Bromo-3-methoxy-7-(2-hydroxynaphthalen-6-yl)-3-methoxynaphthalene-2-carboxylic acid methyl ester, 111 (Scheme 7). White solid. 47% yield, $^1$H NMR (CDCl$_3$): 3.96 (3H, s), 4.01(3H, s), 4.04 (3H, s), 7.17-7.23 (2H, m), 7.8-7.89 (3H, m), 8.05 (1H, dd, J=1.8, 8.8), 8.09 (1H, s), 8.17 (1H, d, J=1.7), 8.35 (1H, d, J=8.8), 8.45 (1H, s).

4-Bromo-3-methoxy-7-(2-methoxynaphthalen-6-yl) naphthalene-2-carboxylic acid, QR-0243 (Scheme 7). White solid, 87% yield, $^1$H NMR (DMSO) 3.92(3H, s), 3.94 (3H, s), 7.24 (1H, dd, J=2.5, 8.9), 7.40 (1H, d, J=2.2), 7.93-8.03 (3H, m), 8.27 (2H, 2s), 8.36 (1H, s), 8.56 (2H, m), 13.38 (1H, s); $^{13}$C NMR (DMSO) 55.76, 62.35, 106.31, 116.54, 119.69, 125.91, 126.16, 126.96, 127.23, 127.59, 128.10, 129.25, 129.38, 130.35, 131.01, 132.44, 133.08, 134.21, 134.39, 138.41, 153.32, 158.20, 166.81.

4-bromo-3-hydroxy-7-(2-hydroxynaphthalen-6-yl)naphthalene-2-carboxylic acid, QR-0263 (Scheme 7). Bright yellow solid, 71% yield, $^1$H NMR (DMSO): 4.70 (3H, s, br), 7.16 (1H, dd, J=2.3, 8.7), 7.19, (1, d, J=2.1), 7.84 (1H, d, J=8.7), 7.90 (1H, d, J=8.9), 7.94 (1H, dd, J=1.6, 8.6), 8.15-8.21 (2H, m), 8.29 (1H, s), 8.55 (1H, s), 8.71 (1H, s); $^{13}$C NMR (DMSO): 107.11, 109.02, 118.44, 119.63, 125.68, 125.82, 126.20, 127.35, 127.46, 128.53, 128.69, 129.57, 130.37, 131.76, 133/69, 134.49, 134.68, 136.33, 152.24, 156.15, 163.10.

Methyl 7-(benzofuran-2-y)-4-bromo-3-methoxynaphthalene-2-carboxylate, 112 (Scheme 7). Light yellow solid, 58% yield, $^1$H NMR (CDCl$_3$) 4.01 (3H, s), 4.07 (3H, s), 7.18 (1H, s), 7.28 (1H, t, J=7.8), 7.33 (1H, td, J=1.8, 7.8), 7.57 (1H, d, J=7.7), 7.63 (1H, d, J=7.3), 8.08 (1H, dd, J=1.7, 8.9), 8.30 (1H, d, J=8.9), 8.38 (1H, d, J=1.45), 8.43 (1H, s); $^{13}$C NMR (CDCl$_3$) 52.65, 62.29, 102.85, 111.29, 117.83, 121.19, 123.24, 124.64, 124.91, 126.03, 126.36, 127.57, 128.45, 129.07, 130.44, 132.72, 134.51, 153.93, 154.73, 155.18, 165.70.

7-(Benzofuran-2-y)-4-bromo-3-methoxynaphthalene-2-carboxylic acid, QR-0237 (Scheme 7). Light yellow solid, 93% yield, $^1$H NMR (DMSO): 3.94 (3H, s), 7.32 (1H, t, J=7.3), 7.39 (1H, t, J=7.3), 7.64 (1H, s), 7.69 (1H, d, J=8.2), 7.73 (1H d, J=7.5), 8.23-8.33 (2H, m), 8.51 (1H, s), 8.65 (1H s), 13.36 (1H, s); $^{13}$C NMR (DMSO): 62.40, 104.16, 111.69, 116.74, 121.96, 123.94, 125.03, 125.64, 126.86, 127.44, 128.18, 128.30, 129.22, 130.69, 132.32, 133.72, 153.82, 154.72, 154.99, 166.77.

7-(Benzofuran-2-y)-4-bromo-3-hydroxynaphthalene-2-carboxylic acid QR-0244 (Scheme 7). Bright yellow solid, 92% yield, $^1$H NMR 7.31 (1H, t, J=7.3), 7.37 (1H, t, J=7.4), 7.57 (1H, s), 7.67 (1H, d, J=8.2), 7.71 (1H, d, J=7.6), 8.15 (1H, d, J=9.0), 8.25 (1H, d, J=8.7), 8.63 (1H, s), 8.75 (1H, s); $^{13}$C NMR (DMSO): 103.30, 106.11, 111.61, 121.78, 123.86, 125.35, 125.93, 126.16, 127.62, 127.67, 129.32, 133.08, 135.33, 154.89, 155.02, 171.65. HRMS: measured=382.9736, theoretical=380.9768.

Methyl 7-(benzo[b]thiophen-2-yl-4-bromo-3-methoxynaphthalene-2-carboxylate, 113 (Scheme 7). White solid, 84% yield, $^1$H NMR (CDCl$_3$) 4.00 (3H, s), 4.03 (3H, s), 7.32-7.41 (2H, m), 7.68 (1H, s), 7.81 (1H, d, J=7.75), 7.86 (1H, d, J=7.75), 8.10 (1H, d, J=8.1), 8.28 (1H, d, J=8.9), 8.39 (1H, s); $^{13}$C NMR (CDCl$_3$) 52.65, 62.29, 117.75, 120.66, 122.37, 123.86, 124.80, 124.86, 126.05, 126.13, 127.67, 127.88, 130.49, 132.41, 132.51, 134.36, 139.69, 140.63, 142.79, 153.84, 165.65.

7-(Benzo[b]thiophen-2-yl-4-bromo-3-methoxynaphthalene-2-carboxylic acid, QR-0245 (Scheme 7). Light yellow solid, 71% yield, $^1$H NMR (DMSO) 7.38-7.47 (2H, m), 7.91 (1H, d, J=7.2), 8.04 (1H, d, J=7.5), 8.08 (1H, s), 8.24 (2H, 2s), 8.53 (2H, 2d overlapping), 13.41 (1H, s); $^{13}$C NMR (DMSO) 62.39, 116.67, 121.92, 123.06, 124.49, 125.48, 125.57, 126.48, 127.51, 128.08, 128.21, 130.80, 132.09, 132.34, 133.60, 139.39, 140.86, 142.52, 153.72, 166.72.

7-(Benzo[b]thiophen-2-yl-4-bromo-3-hydroxynaphthalene-2-carboxylic acid, QR-0255 (Scheme 7). Bright yellow solid, 77% yield, $^1$H NMR (DMSO): 7.36-7.45 (2H, m), 7.89 (1H, d, J=7.6), 8.0-8.06 (2H, m), 8.13 (1H, d, J=8.9), 8.19 (1H, dd, J=1.8, 8.9), 8.48 (1H, d, J=1.7), 8.76 (1H, s); $^{13}$C NMR (DMSO): 105.97, 117.43, 121.19, 123.01, 124.33, 125.41 (2s), 126.23, 127.30, 127.78, 129.01, 130.04, 133, 135.17, 139.21, 140.93, 142.85, 154.70, 171.64.

Methyl 4-bromo-7-(2,3-dihydrobenzo[b][1,4]dioxin-7-yl)-3-methoxynaphthalene-2-carboxylate, 114 (Scheme 7). White solid, 57% yield, $^1$H NMR (CDCl$_3$): 3.98 (3H, s), 4.0 (3H, s), 4.33 (4H, s), 6.98 (1H, d, J=8.35, 7.18-7.25 (2H, m), 7.86 (1H, dd, J=1.05, 8.86), 7.99 (1H, s), 8.28 (1H, d, J=8.8), 8.38 (1H, s); $^{13}$C NMR (CDCl$_3$): 52.59, 62.24, 64.49, 64.55, 116.10, 117.89, 120.37, 126.09, 127.43, 129.00, 130.63, 132.53, 138.59, 143.77, 143.98, 153.31, 165.85.

4-Bromo-7-(2,3-dihydrobenzo[b][1,4]dioxin-7-yl)-3-methoxynaphthalene-2-carboxylic acid, QR-0282 (Scheme 7). White, solid, 92% yield, $^1$H NMR (DMSO): 3.92 (3H, s), 4.32 (4H, s), 7.01 (1H, d, J=8.36), 7.30-7.40 (2H, m), 8.07 (1H, dd, J=1.8, 8.9), 8.18 (1H, d, J=8.9), 8.37 (1H, d, J=1.55), 8.49 (1H, s), 13.32 (1H, s); $^{13}$C NMR (DMSO): 62.32, 64.63, 64.72, 115.94, 116.45, 118.17, 120.34, 126.29, 127.07, 127.51, 129.08, 130.92, 132.36, 132.45, 132.87, 137.88, 144.14, 144.35, 153.17, 166.85.

4-Bromo-7-(2,3-dihydrobenzo[b][1,4]dioxin-7-yl)-3-hydroxyynaphthalene-2-carboxylic acid, QR-0281 (Scheme 7). Bright yellow solid, 70% yield, $^1$H NMR (DMSO): 4.31 (4H, s), 7.00 (1H, d, J=8.3), 7.29-7.35 (2H, m), 8.02 (1H, dd, J=1.8, 8.9), 8.07 (1H, d, J=8.8), 8.34 (1H, d, J=1.4), 8.69 (1H, s); $^{13}$C NMR (DMSO): 64.63, 64.69, 105.67, 115.73, 118.12 120.12, 122.59, 125.85, 127.04, 128.03, 130.00, 132.66, 132.98, 134.47, 135.89, 143.89, 144.31, 144.71, 153.92, 171.85.

3-Benzofuran-2-yl)-1H-indole-7-carboxylic acid, QR-0256 (Scheme 8). Light yellow solid, 50% yield $^1$H NMR (DMSO): 7.21-7.29 (3H, m), 7.33 (1H, t, J=7.7), 7.58-7.65 (2H, m), 7.89 (1H, d, J=7.3), 7.95 (1H, d, J=2.2), 8.38 (1H, d, J=7.9), 11.54 (1H, s), 13.23 (1H, s), $^{13}$C NMR (DMSO): 99.77, 107.14, 111.07, 114.82, 120.45, 120.67, 123.41, 123.78, 125.40, 125.75, 125.92, 126.40, 129.85, 135.65, 152.95, 153.78, 168.07.

Methyl 3-benzo[b]thiophen-2-yl)-1-tosyl-1H-indole-7-carboxylate, 116 (Scheme 8). Light yellow solid, 44% yield $^1$H NMR (CDCl$_3$): 2.32 (3H, s), 3.97 (3H, s), 7.17 (2H, d, J=8.1), 7.34-7.38 (2H, m), 7.41 (1H, t, J=7.7), 7.51 (1H, s), 7.60 (1H, dd, J=1.0, 7.5), 7.62 (2H, d, J=8.40), 7.76 (1H, s), 7.79 (1H, d, J=8.2), 7.84 (1H, d, J=7.8), 8.02 (1H, dd, J=1.1, 8.0).

3-Benzo[b]thiophen-2-yl)-1H-indole-7-carboxylic acid, QR-0261 (Scheme 8). Yellow solid, 67% yield $^1$H NMR (DMSO): 7.32 (2H, t, J=7.6), 7.39 (1H, t, J=7.9), 7.76 (1H s), 7.79(1H, d, J=2.4), 7.83 (1H, d, J=7.8), 7.8 (1H, d, J=7.1), 7.94 (1H, d, J=7.9), 8.33 (1H, d, J=7.9), 11.48 (1H, s), 13.21 (1H, s); $^{13}$C NMR (DMSO) 1110.52, 114.77, 118.64, 120.34, 122.55, 123.40, 124.19, 125.05, 125.28, 125.38, 126.48, 126.70, 135.83, 137.83, 137.85, 141.18, 168.09.

Methyl 1-benzyl-3-iodo-1H-indole-7-carboxylate, 117 (Scheme 9). Yellow solid, 58% yield $^1$H NMR (CDCl$_3$): 3.72 (3H, s), 5.59 (2H, s), 6.90 (2H, d, J=6.35), 7.16-7.26 (5H, m) 7.61 (1H, d, J=7.4), 7.65 (1H, d, J=7.9); $^{13}$C NMR (CDCl$_3$): 52.22, 53.27, 117.31, 119.67, 125.85, 125.95, 126.69, 127.52, 128.58, 132.94, 133.05, 135.67, 137.35, 167.50.

Methyl 3-benzofuran-2-yl-1-benzyl-1H-indole-7-carboxylate, 118 (Scheme 9). Light yellow solid, 51% yield $^1$H NMR (CDCl$_3$) 3.74 (3H, s), 6.57 (2H, s), 6.93 (1H, d), 6.95 (2H, d, J=6.5), 7.20-7.29 (6H, m), 7.49 (1H, d, J=7.5), 7.57-7.60 (1H, m), 7.62 (1H, dd, J=0.93, 7.4), 7.75 (1H, s), 8.27 (1H, dd, J=1.03, 8.0); $^{13}$C NMR (CDCl$_3$): 52.30, 53.39, 100.07, 107.96, 110.71, 117.74, 119.99, 120.27, 122.81, 123.44, 124.67, 125.54, 126.73, 127.57, 127.95, 128.64, 129.59, 130.48, 133.30, 137.26, 152.05, 154.01, 167.85.

3-Benzofuran-2-yl)-1-benzyl-1H-indole-7-carboxylic acid, QR-0284 (Scheme 9). Beige solid, 76% yield $^1$H NMR (DMSO): 5.80 (2H, s), 6.98 (2H, d, J=7.2), 7.18-7.31 (7H, m), 7.59-7.65 (3H, m), 8.31 (1H, s), 8.32 (1H, d, J=8.0), 13.13 (1H, s, br); $^{13}$C NMR (DMSO): 52.5, 100.36, 107.07, 111.05, 119.41, 120.57, 120.84, 123.48, 124.02, 124.45, 125.62, 127.17, 127.61, 127.81, 129.03, 129.77, 131.94, 133.11, 138.24, 152.17, 153.75, 168.90.

Methyl 3-(benzo[b]thiophen-2-yl)-1-benzyl-1H-indole-7-carboxylate, 119 (Scheme 9). Light yellow solid, 53% yield $^1$H NMR (CDCl$_3$): 3.73 (3H, s), 5.64 (2H, s), 6.95 (2H, d, J=6.3), 7.20-7.25 (4H, m), 7.29 (1H, t, J=8.1), 7.36 (1H, t, J=8.0), 7.50 (2H, d, J=7.4), 7.61 (1H, dd, J=1.0, 7.4), 7.77 (1H, d, J=7.8), 7.82 (1H, d, J=7.8), 8.26 (1H, dd, J=1.0, 8.0); $^{13}$C NMR (CDCl$_3$): 52.25, 53.24, 111.35, 117.64, 119.08, 119.84, 122.03, 122.97 123.74, 124.43, 125.58, 126.72, 127.55, 128.63, 128.93, 130.50, 133.41, 137.02, 137.34, 138.61, 140.80, 167.87.

3-(Benzo[b]thiophen-2-yl)-1-benzyl-1H-indole-7-carboxylic acid, QR-0287 (Scheme 9). Beige solid, 87% yield $^1$H NMR (DMSO): 5.78 (2H, s), 6.98 (2H, d, J=7.3), 7.18-7.42 (6H, m), 7.59 (1H, d, J=6.6), 7.77 (1H, s), 7.85 (1H, d, J=7.8), 7.96 (1H, d, J=7.9), 8.16 (1H, s), 8.28 (1H, d, J=8.0); $^{13}$C NMR (DMSO): 52.36, 110.49, 119.14, 119.44, 120.42, 122.58, 123.52, 123.99, 124.33, 125.09, 125.55, 127.13, 127.77, 128.48, 129.01, 132.14, 133.22, 137.10, 137.92, 138.33, 141.11, 168.93.

6-(3-(Pyridine-2-yloxy)phenyl)naphthalene-2-ol, QR-0234 (Scheme 11). White solid, 65% yield $^1$H NMR (DMSO) 7.07-7.18 (5H, m), 7.5-7.56 (2H, m). 7.64 (1H, d, J=8.0), 7.72-7.80 (2H, m), 7.82-7.91 (2H, m), 8.13 (1H, s), 8.18 (1H, dd, J=1.8, 4.8), 9.82 (1H, s); $^{13}$C NMR (DMSO) 108.92, 112.01, 119.52, 119.59, 119.77, 120.36, 123.24, 125.57, 125.78, 127.23, 128.41, 130.40, 130.66, 133.88, 134.52, 140.69, 142.49, 147.95, 154.95, 156.18, 163.60.

EXAMPLE 4

General Procedure for Deprotection of O-methyl Groups

O-methyl groups were deprotected to give compounds QR-0229, QR-0297, QR-0231, QR-0246, and QR-0247. Their synthesis reactions are depicted in Scheme 6 and Scheme 10 of EXAMPLE 3 above, and Scheme 12 below.

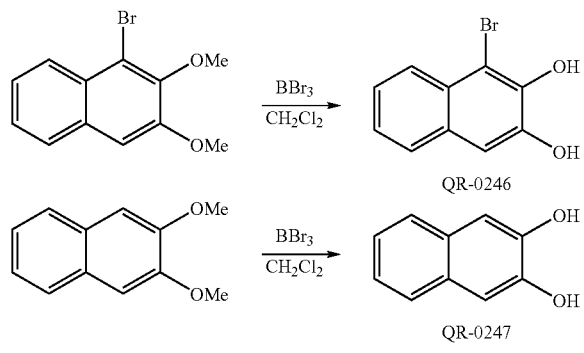

The following procedure was used to deprotect O-methyl groups. To the solution of a methoxy-containing compound in CH$_2$Cl$_2$, BBr$_3$ (2-4 equiv) was added dropwise at −78° C. The reaction mixture was stirred at −78° C. for 20 minutes and warmed up gradually to room temperature. Reaction time varied from 3 hours to 12 hours. The reaction was quenched with saturated NaHCO$_3$ (aq). To make sure that no boron complex remained, in some cases HCl (1.0 M, 2-3 ml) was added to the mixture and stirred for 15-20 minutes. Layers were separated and the aqueous layer was extracted thrice with CH$_2$Cl$_2$. The combined organic layer was dried (MgSO$_4$), filtered and concentrated under vacuum.

The residue was purified by flash chromatography to yield the following compounds.

4-(2,3-Dihydrobenzo[b][1,4]dioxin-7-yl)naphthalene-1-carboxylic acid, QR-0228 (Scheme 6). White solid, 69% yield, $^1$H NMR (CDCl$_3$) 4.35 (4H, s), 6.95-7.03 (3H, m), 7.46 (1H, d, J=7.5), 7.51 (1H, t, J=8.2), 7.66 (1H, t, J=8.2), 8.03 (1H, d, J=8.4), 8.40 (1H, d, J=7.5), 9.15 (1H, d, J=8.7); $^{13}$C NMR (CDCl$_3$) 64.54, 117.26, 118.82, 123.13, 124.51, 125.69, 126.07, 126.28, 126.98, 127.82, 131.17, 132.17, 132.30, 133.38, 143.43, 143.56, 146.13, 171.67.

6-(2,3-Dihydrobenzo[b][1,4]dioxin-7-yl)naphthalene-2-ol, QR-0229 (Scheme 6). Beige solid, 97% yield, $^1$H NMR (CDCl$_3$) 4.30 (4H, s), 5.07 (1H, s), 6.96 (1H, d, J=8.3), 7.08-7.23 (4H, m), 7.62 (1H, dd, J=1.7, 8.5), 7.70 (1H, d, J=8.6), 7.76 (1H, d, J=8.8), 7.89 (1H, s).

1-(2,3-Dihydrobenzo[b][1,4]dioxin-7-yl)-2,3-dihydroxynaphthalene, QR-0231 (Scheme 6). Brown solid, $^1$H NMR (DMSO) 4.31 (4H, s, hr), 6.71-6.77 (2H, m), 6.96 (1H, d, J=8.1), 7.12 (1H, t, J=7.3), 7.16 s), 7.20 (1H, t, J=7.6), 7.28 (1H, d, J=8.2), 7.62 (1H, d, J=7.6), 8.53 (1H, s), 10.20 (1H, s); $^{13}$C NMR (DMSO) 64.58, 108.87, 117.14, 119.85, 121.98, 123.33, 123.37, 124.18, 124.46, 126.40, 128.58, 129.00, 129.67, 142.81, 143.47, 144.12, 146.54.

1,6-dibromo-2-methoxynaphthalene, 120 (Scheme 10). Light brown solid, 94.43% yield $^1$H NMR (CDCl$_3$): 4.03 (3H, s), 7.28 (1H, d, J=9.0), 7.61 (1H, dd, J=2.0, 9.1), 7.73 (1H, d, J=9.0), 7.94 (1H, d, J=1.94), 8.10 (1H, d, J=9.1); $^{13}$C NMR (CDCl$_3$): 57.10, 108.74, 114.55, 118.22, 128.04, 128.11, 129.88, 130.68, 131.01, 131.81, 154.07.

2-(1-Bromo-2-methoxynaphthalen-6-yl)benzofuran, 121 (Scheme 10). White solid, 64% yield $^1$H NMR (CDCl$_3$): 4.10 (3H, s), 7.18 (1H, s), 7.27-7.38 (3H, m, overlapped with CDCl$_3$), 7.59 (1H, d, J=8.2), 7.65 (1H, d, J=7.1), 7.95 (1H, d, J=8.9), 8.02(1H, dd, J=1.7, 8.9), 8.31 (1H, d, J=8.9) 8.36 (1H, d, J=1.5); $^{13}$C NMR (CDCl$_3$): 57.08, 101.91, 104.61, 111.16, 114.25, 120.99, 123.08, 123.89, 124.48, 124.73, 126.40, 126.86, 129.30, 129.50, 129.80, 133.40, 154.33, 155.06, 155.57.

6-(Benzofuran-2-yl)-1-bromonaphthalen-2-ol, QR-0297 (Scheme 10). Light orange solid, 67% yield $^1$H NMR (DMSO): 7.28 (1H, t, J=7.6), 7.32-7.38 m), 7.54 (1H, s), 7.66 (1H, d, J=8.3), 7.69 (1H, d J=7.2), 7.98 (1H, d, J=8.9), 8.12 (2H, s), 8.43 (1H, s); $^{13}$C NMR (DMSO): 102.69, 104.97, 111.53, 119.59, 121.64, 123.78, 124.33, 124.99, 125.12, 125.29, 126.18, 129.06, 129.43, 130.05, 133.17, 153.71, 154.81, 155.54.

1-Bromo-2,3-dihydroxy-naphthalene (QR-0246) (Scheme 12). Beige solid, 79% yield $^1$H NMR (DMSO): 7.19 (1H, s), 7.31 (1H, t, J=7.94), 7.38 (1H, t, J=7.79), 7.67 (1H, d, J=8.39), 7.89 (1H, d, J=8.24), 9.69 (1H, s), 10.49 (1H, s); $^{13}$C NMR (DMSO): 105.46, 109.24, 124.33, 124.88, 125.08, 126.69, 127.52, 129.36, 145.41, 146.91.

2,3-Dihydroxy-naphthalene (QR-0247) (Scheme 12). Beige solid, 62% yield $^1$NMR (DMSO): 7.10 (2H, s), 7.15-7.20 (2H, s), 7.54-7.59 (2H, s), 9.48 (2H, s); $^{13}$C NMR (DMSO) 109.98, 123.32, 125.99, 129.25, 147.30.

EXAMPLE 5

Preparation of 5-methoxy-3-(tributylstannyl)-1-(toluene-4-sulfonyl)-indole (217)

5-methoxy-3-(tributylstannyl)-1-(toluene-4-sulfonyl)-indole (217) was prepared by the reactions depicted in Scheme 13 below.

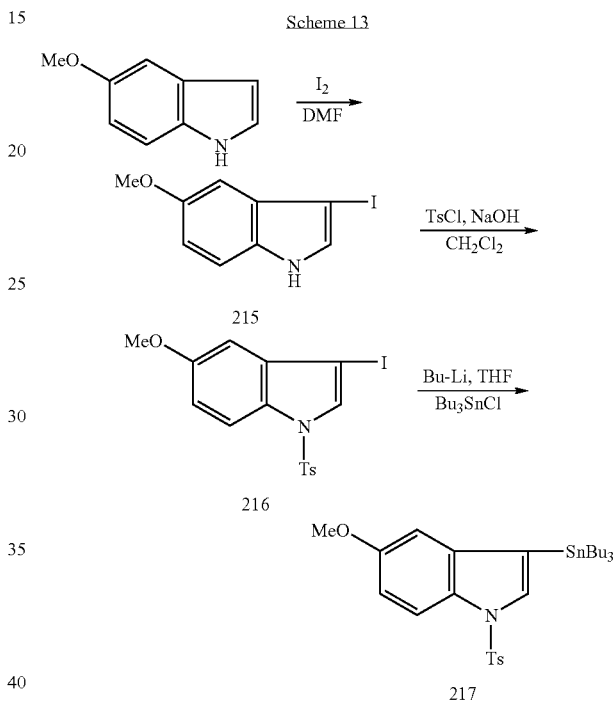

Scheme 13

Procedure 206 of EXAMPLE 7 of U.S. patent application Ser. No. 11/443,396, Publication No. US2007/0015813, was used.

EXAMPLE 6

Preparation of 3-(5-methoxy-1-(toluene-4-sulfonyl)-indol-3-yl)-1-(toluene-4-sulfonyl)-indole-2-carboxylic acid methyl ester (218)

3-(5-methoxy-1-(toluene-4-sulfonyl)-indol-3-yl)-1-(toluene-4-sulfonyl)-indole-2-carboxylic acid methyl ester (218) (Scheme 4) was prepared using the same procedure as 207 in EXAMPLE 7 of U.S. patent application Ser. No. 11/443,396, Publication No. US2007/0015813, with a yield of 80%.

The final product was obtained following flash chromatography, 3-(5-methoxy-1-(toluene-4-sulfonyl)-indol-3-yl)-1-(toluene-4-sulfonyl)-indole-2-carboxylic acid methyl ester (218), $^1$H NMR (CDCl$_3$): 2.32 (s, 3H), 2.34 (s, 3H), 3.70 (s, 3H), 3.81 (s, 3H), 6.73 (d, 1H, J=2.4), 6.94-6.96 (m, 1H), 7.21-7.28 (m, 5H), 7.36 (d, 1H, J=7.8), 7.43 (t, 1H, J=7.6), 7.72 (s, 1H), 7.80 (d, 2H, J=8.3), 7.88-7.92 (m, 3H), 8.10 (d, 1H, J=8.4).

EXAMPLE 7

Preparation of 3-(5-methoxy-indol-3-yl)-1-(toluene-4-sulfonyl)-indole-2-carboxylic acid (QR-0169)

3-(5-methoxy-indol-3-yl)-1-(toluene-4-sulfonyl)-indole-2-carboxylic acid (QR-0169) (Scheme 14) was prepared using the same procedure as for 208 of EXAMPLE 7 of U.S. patent application Ser. No. 11/443,396, Publication No. US2007/0015813, with a yield of 76%.

The final product was obtained following flash chromatography, 3-(5-methoxy-indol-3-yl)-1-(toluene-4-sulfonyl)-indole-2-carboxylic acid (QR-0169) $^1$H NMR (DMSO): 2.33 (s, 3H), 3.63 (s, 3H), 6.68 (d, 1H, J=2.4), 6.96-6.98 (m, 1H), 7.06-7.09 (m, 2H), 7.31 (d, 2H, J=7.9), 7.40 (d, 2H, J=8.2), 7.52 (d, 1H, J=8.4), 7.83 (s, 1H), 7.86-7.89 (m, 2H), 11.98 (s, 1H), 12.88 (s, 1H); $^{13}$C NMR (DMSO): 21.52, 55.75, 104.02, 111.75, 113.21, 113.92, 114.63, 116.30, 120.69, 121.22, 125.34, 125.67, 127.04, 127.24, 127.59, 129.31, 130.66, 132.20, 134.60, 136.64, 145.77, 156.42, 163.14.

EXAMPLE 8

Preparation of 3-(5-methoxy-indole-3-yl)-indole-2-carboxylic acid (QR-0168)

3-(5-methoxy-indole-3-yl)-indole-2-carboxylic acid (QR-0168) was prepared by the reactions depicted in Scheme 14 below and using procedure 209 of EXAMPLE 7 of US2007/0015813, with a yield of 82%.

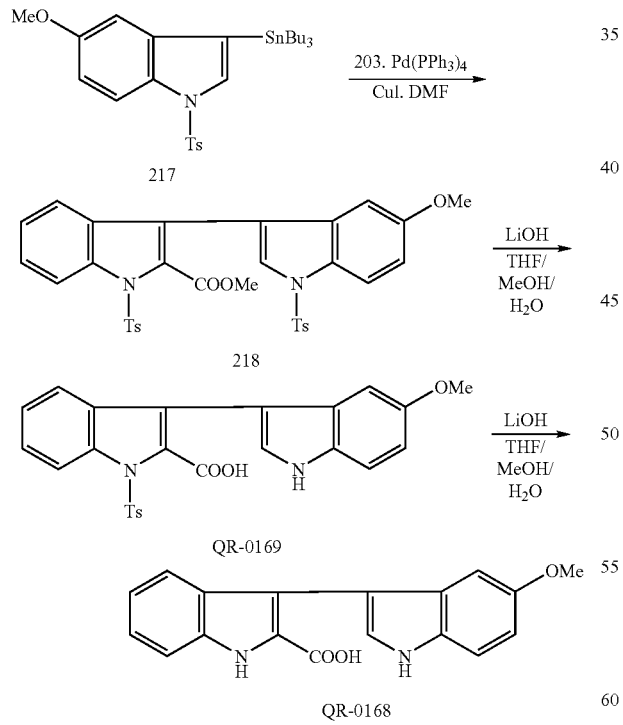

Scheme 14

The final product was obtained following flash chromatography, 3-(5-methoxy-indole-3-yl)-indole-2-carboxylic acid (QR-0168), $^1$H NMR (DMSO): 3.64 (s, 3H), 6.75-6.78 (m, 2H), 7.04 (t, 1H, J=7.5), 7.27 (t, 1H, J=7.6), 7.34 (d, 1H, J=8.6), 7.46-7.50 (m, 3H), 11.10 (s, 1H), 11.65 (s, 1H), 12.68 (s, 1H); $^{13}$C NMR (DMSO): 55.86, 102.49, 107.98, 111.65, 112.80, 113.09, 116.28, 120.08, 122.23, 124.37, 125.23, 126.75, 128.09, 128.31, 131.87, 136.91, 153.76, 163.76.

EXAMPLE 9

Preparation of 3-iodo-1-(toluene-4-sulfonyl)-indole-2-carboxylic Acid Methyl Ester (203)

3-iodo-1-(toluene-4-sulfonyl)-indole-2-carboxylic acid methyl ester (203) was prepared as follows.

To a mixture of 3-iodoindol-2-carboxylic acid methyl ester (202) (0.604 g, 2 mmol) and NaH (60%, 0.192 g, 2.4 mmol) in DMF (20 mL) was added p-toluenesulfonylchloride (0.381 g, 2 mmol) at room temperature. After stirring for 1 hour, ethyl acetate (50 mL) was added to the reaction mixture. The mixture was washed with brine (3×30 mL). The organic layer was dried with MgSO$_4$, filtered and concentrated under vacuum. The residue was purified by flash chromatography (10% ethyl acetate/hexane V:V) to afford 203 (0.68 g, 76%). $^1$H NMR (CDCl$_3$): 2.35 (s, 3H), 4.05 (s, 3H), 7.23 (d, 2H, J=8.4), 7.33 (t, 1H, J=7.2), 7.41, (m, 2H), 7.83 (d, 2H, J=8.4), 7.98 (d, 1H, J=8.4).

EXAMPLE 10

Preparation of 5-nitro-3-iodo-1-(toluene-4-sulfonyl)-indole (222)

5-nitro-3-iodo-1-(toluene-4-sulfonyl)-indole (222) was prepared by the reaction depicted in Scheme 15 below, following procedure 212 of EXAMPLE 7 of US2007/0015813.

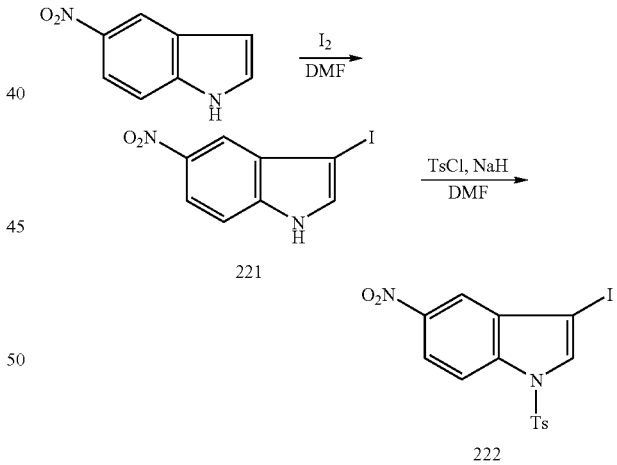

Scheme 15

EXAMPLE 11

Preparation of 3-(1-(toluene-4-sulfonyl)-indole-3-yl)-5-nitro-1-(toluene-4-sulfonyl)-indole (223)

3-(1-(toluene-4-sulfonyl)-indole-3-yl)-5-nitro-1-(toluene-4-sulfonyl)-indole (223) was prepared as follows.

A solution of 222 (0.331 g, 0.748 mmol), crude 206 (0.42 g, 0.748 mmol), catalytic amount of CuI and tetrakis(triphenylphosphine)palladium in DMF (10 mL) was degassed with argon for 10 min (Scheme 16). The mixture was brought to 50° C. and stirred for 5 h. The solvent was removed in vacuo and the residue was purified by flash chromatography (20% ethyl acetate/hexane V:V) to yield 223 (0.22 g, 50%). $^1$H NMR (CDCl$_3$): 2.36 (s, 3H), 2.38 (s, 3H), 7.26-7.33 (m, 5H), 7.43 (t, 1H. J=7.8), 7.56 (d, 1H, J=7.8), 7.80 (s, 1H), 7.84-7.87 (m, 4H), 7.92 (s, 1H), 8.11 (d, 1H, J=8.4), 8.17 (d, 1H, J=9.1), 8.28 (d, 1 H, J=9.0), 8.48 (s, 1H).

EXAMPLE 12

Preparation of 3-(1-(toluene-4-sulfonyl)-indole-3-yl)-5-nitroindole (QR-0170)

3-(1-(toluene-4-sulfonyl)-indole-3-yl)-5-nitroindole (QR-0170) was prepared by the reactions depicted in Scheme 16 below.

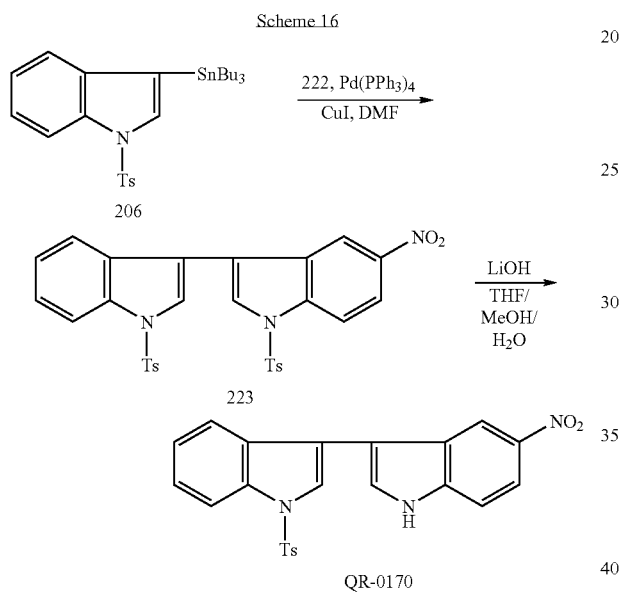

The following procedure was used.

To a solution of 223 (0.2 g, 0.34 mmol) in THF/MeOH/H$_2$O (5:5:1) was added LiOH (0.052 g, 2.2 mmol) (Scheme 16). The reaction mixture was stirred at 50° C. for 0.5 h. The solution was cooled to room temperature and concentrated. Water (10 mL) was added and pH was adjusted to 7 with 1N HCl. The aqueous phase was extracted with ethyl acetate (3×10mL). The combined organic phase was dried with MgSO$_4$, and the solvent was removed in vacuo. The residue was purified by flash chromatography (ethyl acetate/hexane, 1:1, V:V) to yield QR-0170 (0.13 g, 89%), $^1$H NMR (DMSO): 2.30 (s, 3H), 7.33-7.39 (m, 3H), 7.45 (t, 1H, J=7.6), 7.66 (d, 1H, J=9.0), 7.80 (d, 1H, J=7.8), 7.96 (d, 2H, J=8.3), 8.06-8.10 (m, 3H), 8.13 (s, 1H), 8.60 (d, 1H, J=1.7), 12.18 (s, 1H); $^{13}$C NMR (DMSO): 21.49, 109.45, 112.89, 114.04, 116.56, 116.89, 117.64, 121.21, 123.24, 124.33, 125.48, 125.78, 127.29, 128.41, 129.84, 130.71, 134.52, 135.20, 139.97, 141.60, 146.03.

EXAMPLE 13

Preparation of Bis(3-indolyl)methanone (229)

First, compound 226 (Scheme 17) was prepared using the same procedure as for 205 of EXAMPLE 7 of U.S. patent application Ser. No. 11/443,396. Publication No. US2007/0015813 by the reaction depicted in Scheme 17 below.

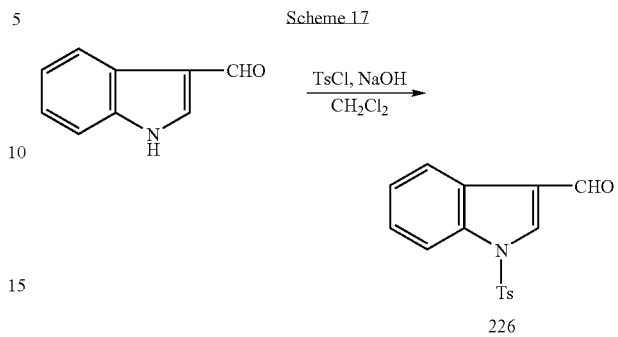

Then, Bis(3-indolyl)methanone (229) was prepared by the reactions depicted in Scheme 18 below.

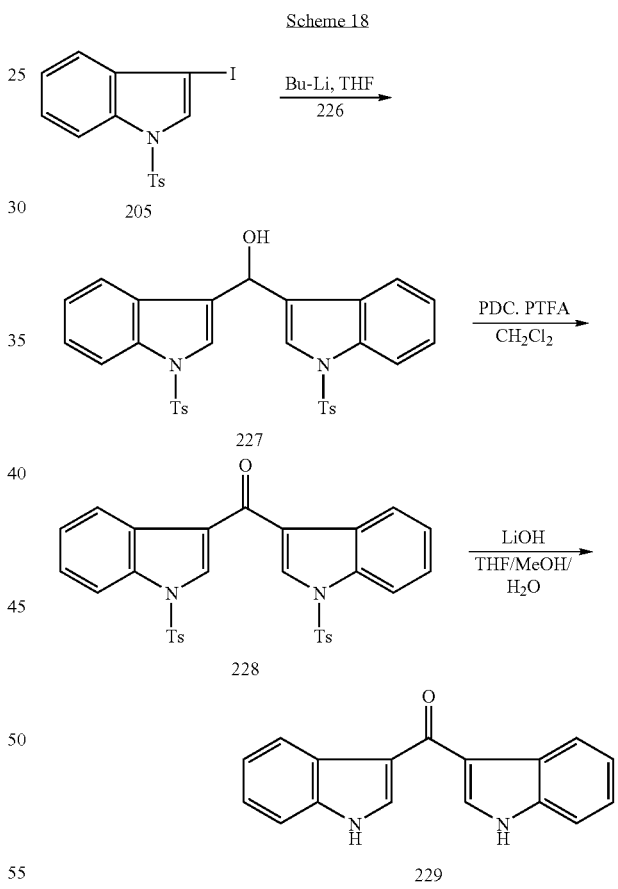

The following procedure was used.

To a solution of 205 (397 mg, 1 mmol) in dry THF (10 mL) was added n-BuLi (0.8 mL, 2.5 M) at −78° C. over a period of 10 min (Scheme 18). After stirring for 15 min, 226 (400 mg, 1.5 mmol), dissolved in dry THF (10 mL), was added over a period of 5 min and the resulting mixture stirred for 5 h. Aqueous HCl (1%, 40 mL) was added, and the mixture was extracted with ethyl acetate (3×20mL). The combined organic layers were washed with saturated NaHCO$_3$ solution and brine and dried over MgSO$_4$. The solvent was evaporated and the residue purified by column chromatography (ethyl acetate/hexane, 3:7, V: V) to yield 227 (383 mg, 67%), $^1$H NMR (CDCl$_3$): 2.35 (s, 6H), 6.23 (s, 1H), 7.12 (t, 2H, J=7.6), 7.20 (d, 4H, J=8.1), 7.30 (t, 2H, J=7.8), 7.38 (d, 2H, J=7.9), 7.49 (s, 2H), 7.70 (d, 4H, J=8.3), 7.99 (d, 2H, J=8.4).

To a solution of 227 (285 mg, 0.5 mmol) in dry CH$_2$Cl$_2$ (10 mL) was added PDC (pyridinium dichromate) (940 mg, 2.5 mmol) and PTEA (pyridinium trifluoroacetate) (190 mg, 1 mmol) (Scheme 18). The mixture was stirred for 2 h at room temperature. The solid chromium waste was removed by filtration, the solvent was evaporated, and the residue was purified by column chromatography on silica gel with CH$_2$Cl$_2$/hexane, 2:1, V:V) to yield 228 (263 mg, 93%), $^1$H NMR (CDCl$_3$): 2.38 (s, 6H), 7.30 (d, 4H, J=8.2), 7.39 (t, 2H, J=4.0), 7.42 (t, 2H, J=4.2), 7.85 (d, 4H, J=8.4), 8.04 (d, 2H, J=8.3), 8.10 (s, 2H), 8.22 (d, 2H, J=7.8).

LiOH (12 mg, 0.5 mmol) and 228 (100 mg, 0.176 mmol) in MeOH/THF/H$_2$O (1:1:1, 15 mL) were heated under reflux for 2 h (Scheme 18). The resulting mixture was concentrated and the residue dissolved with ethyl acetate. The solution was washed with brine and the organic layer dried over MgSO$_4$. The solvent was evaporated and the residue purified by column chromatography (ethyl acetate/CH$_2$Cl$_2$, 1:1, V:V) to yield 229 (38 mg, 83%), $^1$H NMR (DMSO): 7.16-7.24 (m, 4H), 7.50 (d, 2H, J=7.9), 8.16 (d, 2H, J=2.9), 8.26 (2H, J=7.7), 11.80 (s, 2H); $^{13}$C NMR (DMSO): 112.36, 117.30, 121.45, 121.96, 122.99, 127.02, 132.40, 136.97, 185.04.

EXAMPLE 14

Preparation of QR-0174

QR-0173 (Scheme 19) was prepared using the procedure to prepare 229 in the example above, by the reactions depicted in Scheme 19 below.

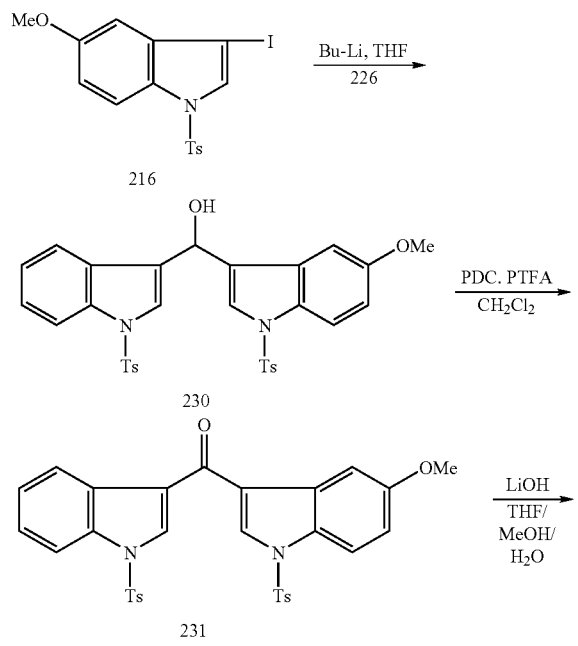

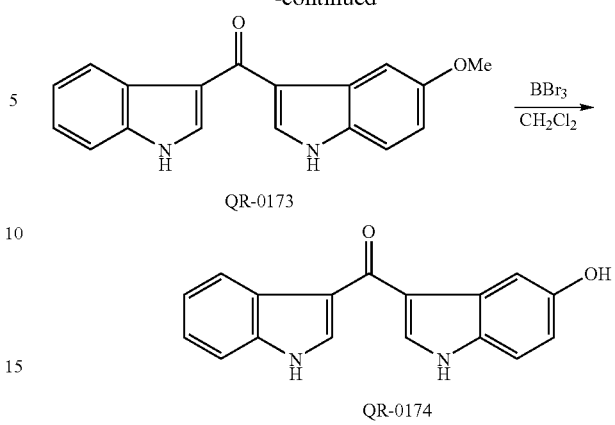

The procedures yielded the following compounds:

231 (58% yield), $^1$H NMR (DMSO): 2.33 (s, 6H), 3.79 (s, 3H), 7.07 (dd, 1H, J$_1$=9.1, J$_2$=2.4), 7.39-7.42 (m, 5H), 7.47 (t, 1H, J=7.7), 7.61 (d, 1H, J=2.3), 7.91 (d, 1H, J=9.1), 7.99-8.04 (m, 5H), 8.13 (d, 1H, J=7.8), 8.62 (s, 1H), 8.64 (s, 1H).

QR-0173 (84% yield), $^1$H NMR (DMSO): 3.81 (s, 3H), 6.86 (dd, 1H, J$_1$=8.8, J$_2$=2.5), 7.18 (t, 1H, J=7.4), 7.22 (t, 1H, J=8.0), 7.39 (d, 1H, J=8.8), 7.50 (d, 1H, J=7.9), 7.81 (d, 1H, J=2.4), 8.12 (d, 1H, J=3.0), 8.15 (d, 1H, J=2.9), 8.27 (d, 1H, J=7.7), 11.69 (s, 1H), 11.78 (s, 1H); $^{13}$C NMR (DMSO): 55.74, 103.53, 112.35, 113.05, 113.13, 117.09, 117.28, 121.39, 121.95, 122.94, 127.05, 127.71 131.89, 132.14, 132.74, 136.95, 155.38, 185.05.

QR-0174 was then synthesized by deprotecting o-methyl group of QR-0173 by using General Procedure A.

General Procedure A

To a solution of compound containing methoxy group in dry CH$_2$Cl$_2$ was added BBr$_3$ (2-10 equivalent) at −78° C. The mixture was stirred overnight and allowed to warm to room temperature. Water was added, and the mixture was extracted with ethyl acetate. The organic layer was washed with brine and dried over MgSO$_4$. The solvent was evaporated and the residue purified by column chromatography to yield the following compounds.

QR-0174 (87% yield), $^1$H NMR (DMSO): 6.72 (dd, 1H, J$_1$=8.6, J$_2$=2.3), 7.18 (t, 1H, J=7.2), 7.21 (t, 1H, J=7.0), 7.29 (d, 1H, J=8.6), 7.49 (d, 1H, J=7.9), 7.69 (d, 1H, J=2.1), 8.04 (d, 1H, J=2.9), 8.11 (d, 1H, J=2.8), 8.24 (d, 1H, J=7.7), 8.91 (s, 1H), 11.58 (s, 1H), 11.78 (s, 1H): $^{13}$C NMR (DMSO): 106.28, 112.32, 112.67, 113.07, 116.76, 117.39, 121.31, 121.96, 122.90, 127.06, 128.03, 131.24, 131.90, 132.63, 136.92, 152.94, 185.01.

EXAMPLE 15

Preparation of QR-0171

QR-0171 (Scheme 20) was synthesized using the same procedure as for 214 of EXAMPLE 7 of U.S. patent application Ser. No. 11/443,396, Publication No. US2007/0015813. The reactions used are depicted in Scheme 20 below.

Scheme 20

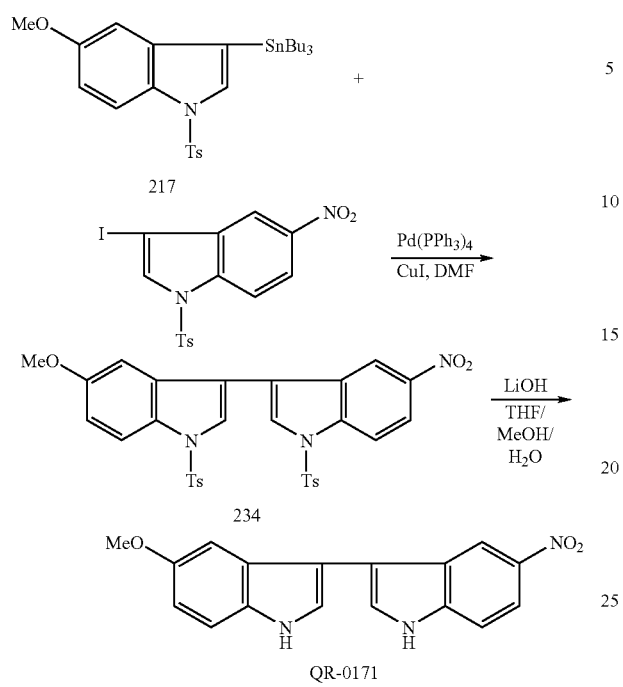

After column chromatography, the following compounds were recovered:

234 (64% yield), $^1$H NMR (CDCl$_3$): 2.36 (s, 6H), 2.39 (s, 3H), 3.78 (s, 3H), 6.95 (d, 1H, J=2.4), 7.03 (dd, 1H, J$_1$=9.1, J$_2$=2.4), 7.24-7.32 (m, 4H), 7.73 (s, 1H), 7.82-7.86 (m, 4H), 7.89 (s, 1H), 8.00 (d, 1H, J=9.1), 8.18 (d, 1H, J=9.1) 8.28 (dd, 1H, J$_1$=9.2, J$_2$=2.2), 8.46 (d, 1H, J=2.1).

QR-0171 (48% yield), $^1$H NMR (DMSO): 3.17 (s, 3H), 6.82 (dd, 1H, J$_1$=8.8, J$_2$=2.3), 7.20 (d, 1H, J=2.2), 7.38 (d, 1H, J=8.8), 7.62 (d, 1H, J=9.0), 7.68 (d. 1H, J=2.4), 7.89 (d, 1H, J=2.6), 8.05 (dd, 1H, J$_1$=9.0, J$_2$=1.8), 8.60 (d, 1H, J=2.0). 11.16 (s, 1H), 11.93 (s, 1H); $^{13}$C NMR (DMSO): 55.84, 101.44, 108.32, 112.21, 112.54, 112.95, 113.20, 117.12, 117.19, 123.88, 125.91, 126.60, 132.08, 139.93, 141.05, 154.15.

EXAMPLE 16

Preparation of 4-methoxyl-3-(tributylstannyl)-1-(toluene-4-sulfonyl)-indole (238)

4-methoxyl-3-(tributylstannyl)-1-(toluene-4-sulfonyl)-indole (238) (Scheme 21) was prepared using the same procedure as for 206 of EXAMPLE 7 of U.S. patent application Ser. No. 11/443,396, Publication No. US2007/0015813. Reactions used are depicted in Scheme 21 below.

Scheme 21

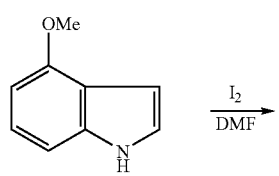

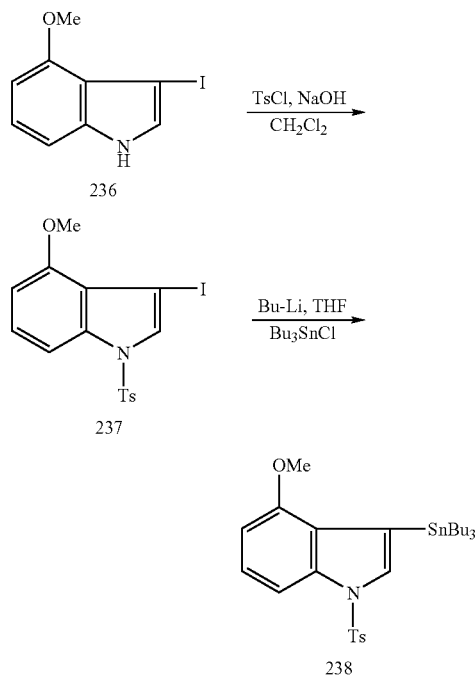

EXAMPLE 17

Preparation of QR-0179

QR-0179 (Scheme 22) was prepared using procedure 214 of EXAMPLE 7 of US2007/0015813. Reactions used are depicted in Scheme 22 below.

Scheme 22

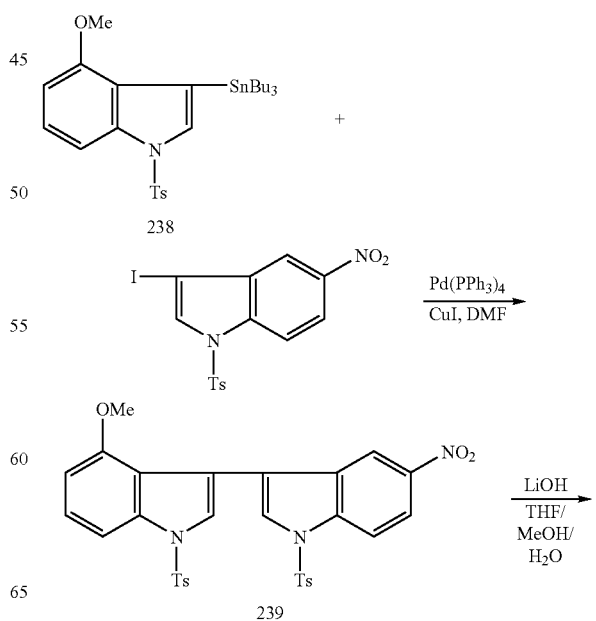

-continued

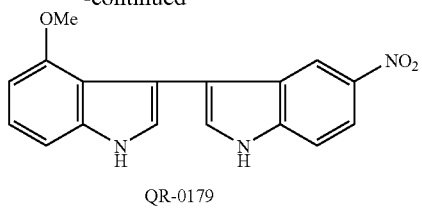
QR-0179

After column chromatography the following compounds were recovered:

239 (73% yield), $^1$H NMR (CDCl$_3$): 2.36 (s, 3H), 2.39 (s, 3H), 3.63 (s, 3H), 6.70 (d, 1H, J=8.0), 7.28-7.34 (m, 5H), 7.61 (s, 1H), 7.72 (d, 1H, J=8.4), 7.83-7.87 (m, 5H), 8.12 (d, 1H, J=9.2), 8.22 (dd, 1H, J$_1$=9.2, J$_2$=2.2), 8.39 (d, 1H, J=2.1).

QR-0179 (32% yield), $^1$H NMR (DMSO): 3.68 (s, 3H), 6.55 (t, 1H, J=4.2), 7.08 (d, 2H, J=3.5), 7.43 (d, 1H, J=2.2), 7.65 (d, 1H, J=9.0), 7.64 (d, 1H, J=2.0), 8.00 (dd, 1H, J$_1$=9.0, J$_2$=2.1), 8.52 (d, 1H, J=1.8), 11.29 (s, 1H), 11.75 (s, 1H); $^{13}$C NMR (DMSO): 55.19, 100.15, 105.63, 107.69, 112.19, 113.91, 116.33, 116.59, 117.82, 122.73, 123.15, 127.26, 127.71, 138.70, 139.58, 140.85, 154.37.

EXAMPLE 18

Preparation of QR-0178

QR-0178 was prepared by the reaction depicted in Scheme 23 below.

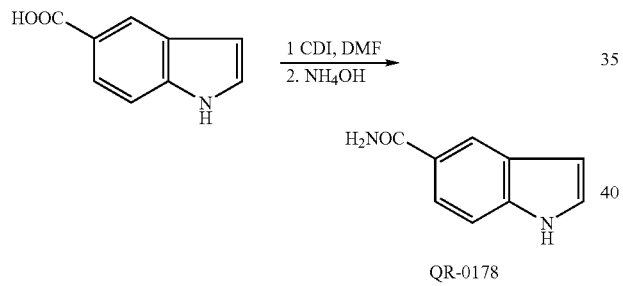

1,1'-Carbonyldiimidazole ("CDI") (324 mg, 2 mmol) was added to the solution of indole-5-carboxyic acid (161 mg, 1 mmol) in dry DMF (5 mL) at 0° C. (Scheme 23). After the mixture was stirred for 1 h, concentrated aqueous ammonia (0.4 mL) was added and the solution stirred overnight at room temperature. Water (25 mL) was added to the mixture and the aqueous solution extracted with ethyl acetate (3×25 mL). The combined organic phase was dried with MgSO$_4$, filtered and concentrated under vacuum. The residue was purified by flash chromatography to yield the following compound.

QR-0178 (60% yield), $^1$H NMR (DMSO): 6.51 (t, 1H, J=2.0), 7.06 (s, 1H), 7.39-7.41 (m, 2H), 7.65 (dd, 1H, J$_1$=8.5, J$_2$=1.7), 7.81 (s, 1H), 8.15 (s, 1H), 11.28 (s, 1H); $^{13}$C NMR (DMSO): 102.66, 111.25, 120.76, 121.43, 125.73, 126.92, 127.46, 137.92, 169.55.

EXAMPLE 19

Preparation of QR-0177

QR-0177 (Scheme 24) was prepared using the procedure of EXAMPLE 18 by the reaction depicted in Scheme 24 below.

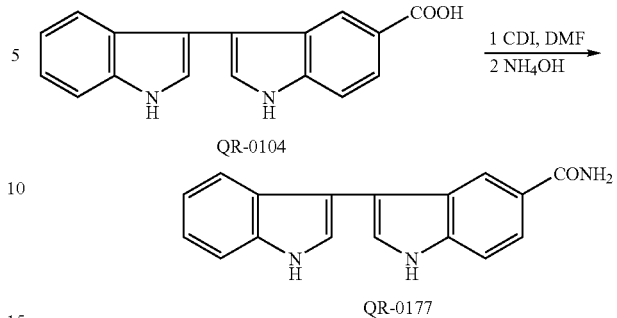

The following compound was afforded.

QR-0177 (56% yield), $^1$H NMR (DMSO): 7.07 (t, 2H, J=7.4), 7.15 (t, 1H, J=7.5), 7.46 (t, 2H, J=7.8), 7.71-7.73 (m, 2H), 7.80-7.81 (m, 2H), 7.95 (s, 1H). 8.37 (s, 1H), 11.20 (s, 1H), 11.37 (s, 1H); $^{13}$C NMR (DMSO): 109.63, 111.40, 111.44, 112.04, 119.42, 119.99, 120.24, 121.74, 122.83, 123.37, 125.76, 125.85, 126.45, 136.89, 138.40, 169.70.

EXAMPLE 20

Preparation of Methane Linked Bis-Indoles

Compounds 243, QR-0192, QR-0193, QR-0182, QR-0181, QR-0191, and QR-0190 were prepared by the reaction depicted in Scheme 25 below.

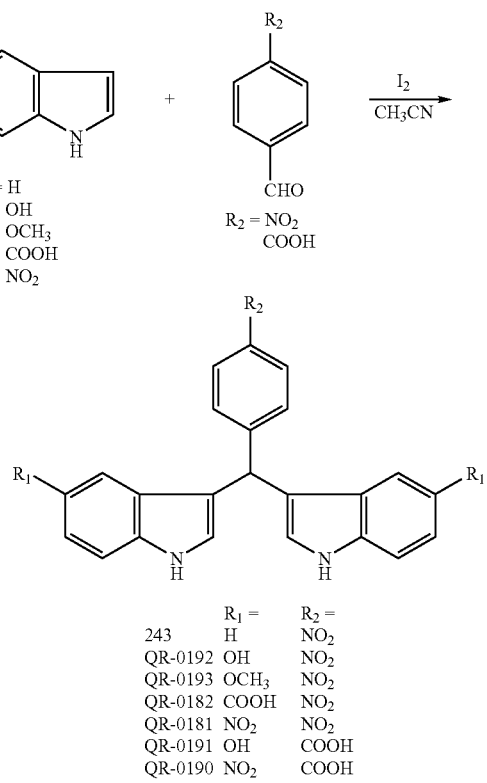

| | R$_1$ = | R$_2$ = |
|---|---|---|
| 243 | H | NO$_2$ |
| QR-0192 | OH | NO$_2$ |
| QR-0193 | OCH$_3$ | NO$_2$ |
| QR-0182 | COOH | NO$_2$ |
| QR-0181 | NO$_2$ | NO$_2$ |
| QR-0191 | OH | COOH |
| QR-0190 | NO$_2$ | COOH |

The following General Procedure B was used to prepare methane linked bis-indoles.

General Procedure B

A mixture of 4-substituted benzaldehyde (1 mmol), 5-substituted indole (2 mmol) and $I_2$ (0.2 mmol) in acetonitrile (10 mL) was stirred at room temperature for 5-30 min. After completion of the reaction, the mixture was treated with aqueous $Na_2SO_3$ (5%, 10 mL), and the mixture was adjusted to pH 7 or 2 with HCl (1 N) when required. The mixture was extracted with ethyl acetate and the organic layer washed with brine and dried over $MgSO_4$. The solvent was evaporated and the residue purified by column chromatography to yield the following:

243 (92% yield), $^1$H NMR (DMSO): 6.03 (s, 1H), 6.89 (t, 2H, J=7.4), 6.90 (s, 2H), 7.06 (t, 2H, J=7.5), 7.30 (d, 2H, J=7.9), 7.37 (d, 2H, J=8.1), 7.61 (d, 2H, J=8.7), 8.15 (d, 2H, J=8.7), 10.92 (s, 2H); $^{13}$C NMR (DMSO): 40.20, 112.07, 117.17, 118.90, 119.39, 121.58, 123.89, 124.34, 126.86, 129.93, 137.09, 146.26, 153.62.

QR-0192 (88% yield), $^1$H NMR (DMSO): 5.77 (s, 1H), 6.57 (d, 2H, J=2.2), 6.58 (s, 2H), 6.73 (d, 2H, J=2.1), 7.15 (d, 2H, J=9.3), 7.56 (d, 2H, J=8.7), 8.17 (d, 2H, J=8.7), 8.52, (s, 2H), 10.59 (s, 2H); $^{13}$C NMR (DMSO): 40.26, 103.45, 111.90, 112.35, 116.17, 123.85, 124.76, 127.54, 129.95, 131.64, 146.21, 150.60, 153.65.

QR-0193 (75% yield), $^1$H NMR (DMSO): $^1$H NMR (DMSO): 3.61 (s, 6H), 5.96 (s, 1H), 6.73 (dd, 2H, $J_1$=8.7, $J_2$=2.4), 6.77 (d, 2H, J=2.2), 6.90 (d, 2H, J=2.1), 7.27 (d, 2H, J=8.7), 7.62 (d, 2H, J=8.7), 8.16 (d, 2H, J=8.7), 10.77 (s, 2H); $^{13}$C NMR (DMSO): 39.86, 55.78, 101.70, 111.30, 112.66, 116.81, 123.87, 125.05, 127.25, 129.90, 132.26, 146.20, 153.36, 153.74.

QR-0182 (89% yield), $^1$H NMR (DMSO): 6.25 (s, 1H), 6.95 (d, 2H, J=1.9), 7.45 (d, 2H, J=8.6), 7.64 (d, 2H, J=8.7), 7.72 (dd, 2H, $J_1$=8.5, $J_2$=1.3), 8.04 (s, 2H), 8.20 (d, 2H, J=8.7), 11.31 (s, 2H), 12.33 (s, 2H); $^{13}$C NMR (DMSO): 38.77, 111.37, 118.09, 121.11, 121.64, 122.53, 123.58, 125.59, 125.89, 129.44, 129.13, 145.98, 152.44, 168.24.

QR-0181 (90% yield), $^1$H NMR (DMSO): 6.48 (s, 1H), 7.22 (s, 2H), 7.56 (d, 2H, J=9.0), 7.67 (d, 2H, J=8.7), 7.99 (dd, 2H, $J_1$=9.0, $J_2$=2.1), 8.20 (d, 2H, J=8.7), 8.39 (d, 2H, J=2.0), 11.76 (s, 2H); $^{13}$C NMR (DMSO): 38.47, 112.71, 116.53, 117.28, 119.77, 124.27, 126.10, 128.43, 129.89, 140.24, 140.88, 146.64, 152.30.

QR-0191 (65% yield), $^1$H NMR (DMSO): 5.66 (s, 1H), 6.56-6.59 (m, 4H), 6.69 (s, 2H), 7.14 (d, 2H, J=8.4), 7.42 (d, 2H, J=7.8), 7.87 (d, 2H, J=7.8), 8.47 (s, 2H), 10.51 (s, 2H), 12.53 (s, 1H); $^{13}$C NMR (DMSO): 40.43, 103.56, 111.78, 112.25, 116.82, 124.62, 127.68, 128.83, 128.94, 129.69, 131.65, 150.50, 150.69, 167.83.

QR-0190 (84% yield), $^1$H NMR (DMSO): 6.31 (s, 1H), 7.16 (s, 2H), 7.49 (d, 2H, J=8.0), 7.56 (d, 2H, J=9.0), 7.90 (d, 2H, J=7.9), 7.98 (d, 2H, J=8.8), 8.34 (s, 2H), 11.78 (s, 2H); $^{13}$C NMR (DMSO): 38.79, 112.65, 116.61, 117.13, 120.43, 126.21, 128.25, 128.68, 130.04, 130.76, 140.28, 140.75, 148.76, 168.01.

EXAMPLE 21

Preparation of QR-0198, QR-0197 and QR-0206

Compounds QR-0198, QR-0197 and QR-0206 were prepared by the reactions depicted in Scheme 26 below.

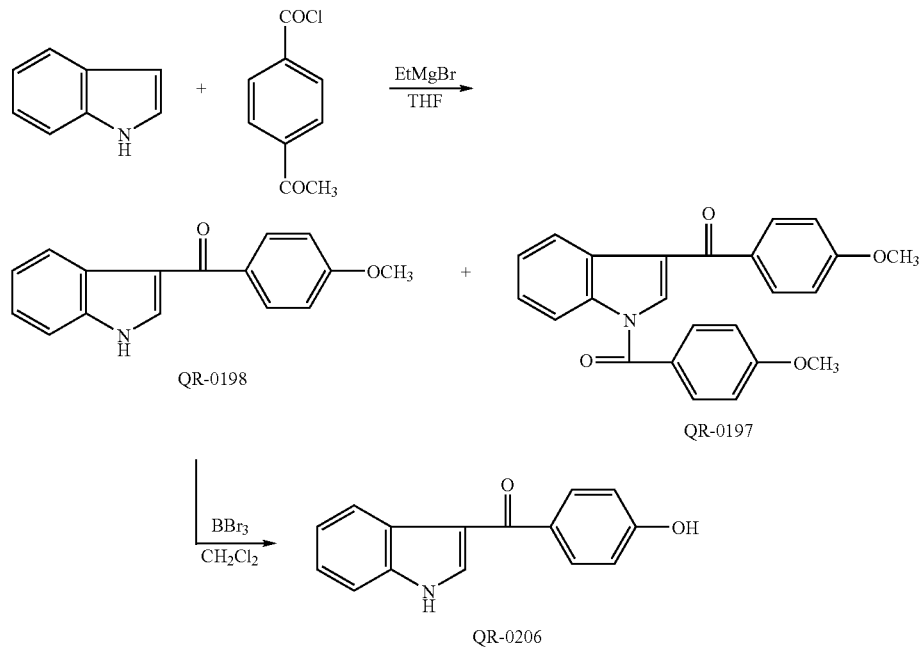

Scheme 26

The following procedure was used. A suspension of indole (1.17 g, 10 mmol) in THF (50 mL) was cooled to −20° C. and ethylmagnesium bromide (3.7 mL, 3.0 M in THF) was added dropwise. The mixture was warmed to room temperature for 3 h, and 4-anisolecarboxylic acid chloride (1.70 g, 10 mmol) in dry THF (30 mL) was added dropwise. After stirring overnight, ethyl acetate (150 mL) was added and the mixture was washed with brine. After drying the organic layer over MgSO$_4$, the solvent was evaporated and the residue purified by column chromatography to yield the following:

QR-0198 (42% yield), $^1$H NMR (DMSO): 3.86 (s, 3H), 7.08 (d, 2H, J=8.6), 7.20-7.26 (m, 2H), 7.52 (d, 1H, J=7.6), 7.81 (d, 2H, J=8.6), 7.94 (d, 1H, J=2.9), 8.22 (d, 1H, J=7.6), 11.99 (s, 1H); $^{13}$C NMR (DMSO): 55.88, 112.62, 114.14, 115.54, 121.92, 122.13, 123.43, 126.93, 131.07, 133.44, 135.30, 137.10, 162.26, 189.22.

QR-0197 (38% yield), $^1$H NMR (CDCl$_3$): 3.88 (s, 3H), 3.90 (s, 3H), 6.69 (d, 2H, J=8.8), 7.02 (d, 2H, J=8.8), 7.40-7.45 (m, 2H), 7.77 (d, 2H, J=8.8), 7.83 (s, 1H), 7.87 (d, 2H, J=8.8), 8.20-8.25 (m, 2H); $^{13}$C NMR (CDCl$_3$): 55.51, 55.64, 113.80, 114.26, 115.69, 120.14, 122.37, 124.90, 125.35, 125.79, 128.62, 131.33, 132.05, 132.13, 133.98, 136.61, 163.10, 163.50, 168.07, 189.85.

QR-0206 was prepared by deprotecting o-methyl group of QR-0198 using General Procedure A of EXAMPLE 14. The following compound was afforded, QR-0206 (76% yield), $^1$H NMR (DMSO): 6.89 (d, 2H, J=8.2), 7.18-7.25 (m, 2H), 7.51 (d, 1H, J=7.8), 7.72 (d, 2H, J=8.0), 7.93, (d, 1H, J=2.2), 8.21 (d, 1H, J=7.5), 10.07 (s, 1H), 11.94 (s, 1H); $^{13}$C NMR (DMSO): 112.57, 115.46, 115.56, 121.94, 122.00, 123.32, 126.99, 131.32, 131.94, 134.94, 137.05, 160.95, 189.24.

EXAMPLE 22

Preparation of QR-0205

Compound 253 was prepared by the reactions depicted in Scheme 27 below, using procedure as that for QR-0198 in the EXAMPLE 21.

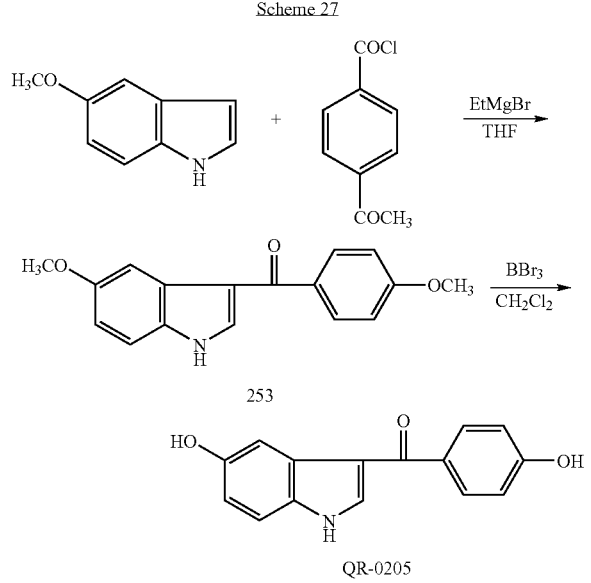

The following compound was recovered, 253 (72% yield), $^1$H NMR (CDCl$_3$): 3.87 (s, 3H), 3.88 (s, 3H), 6.94 (dd, 1H, J$_1$=8.8, J$_2$=2.5), 6.97 (d, 2H, J=8.7), 7.30 (d, 1H, J=8.8), 7.62 (d, 1H, J=3.1), 7.84 (d, 2H, J=8.7), 7.92 (d, 1H, J=2.4), 9.02 (s, 1H); $^{13}$C NMR (CDCl$_3$): 55.47, 55.79, 103.55, 112.20, 113.62, 114.51, 116.92, 127.40, 130.96, 131.25, 133.28, 133.44, 156.38, 162.35, 190.55.

Compound QR-0205 was then prepared following General Procedure A of EXAMPLE 14, to afford QR-0205 (70%), $^1$H NMR (DMSO): 6.74 (dd, 1H, J$_1$=8.6, J$_2$=2.0), 6.91 (d, 2H, J=8.4), 7.29 (d, 1H, J=8.6), 7.62, (d, 1H, J=1.6), 7.67, (d. 2H, J=8.4), 7.76 (d, 1H, J=2.9), 8.99 (s, 1H), 10.17 (s, 1H), 11.86 (s, 1H); $^{13}$C NMR (DMSO): 106.31, 112.86, 113.27, 115.03, 115.40, 128.02, 131.05, 131.24, 132.12, 134.84, 153.41, 160.85, 189.17.

EXAMPLE 23

Preparation of QR-0196

Compound QR-0196 was prepared by the reaction depicted in Scheme 28 below.

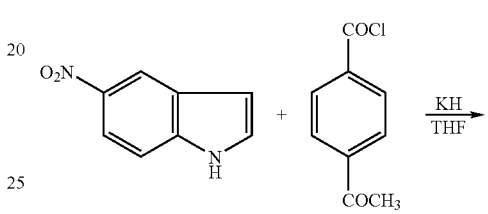

The following procedure was used.

5-Nitroindole (162 mg, 1 mmol) was dissolved in dry THF (5 mL) and added dropwise to a suspension of KH (137 mg, 35%, 1.2 mmol) in THF (10 mL) cooled to −15° C. After 30 min., 4-anisolecarboxylic acid chloride (170 mg, 1 mmol) was added and the reaction stirred at room temperature for 4 h. Water (10 mL) was added and the aqueous layer was extracted with EtOAc (30 mL). The organic layer was dried with MgSO$_4$ and the product was purified by column chromatography to yield the following compound.

QR-0196 (51% yield), $^1$H NMR (CDCl$_3$): 3.93 (s, 3H), 6.77 (d, 1H, J=3.7), 7.05 (d, 2H, J=8.8), 7.56 (d, 1H, J=3.7), 7.78 (d, 2H, J=8.8), 8.25 (dd, 1H. J$_1$=9.1, J$_2$=2.2), 8.40 (d, 1H, J=9.1), 8.54 (d, 1H, J=2.2); $^{13}$C NMR (CDCl$_3$): 55.66, 108.32, 114.22, 116.25, 117.21, 119.90, 125.25, 130.47, 130.58, 132.08, 139.18, 144.25, 163.45, 167.94.

EXAMPLE 24

Preparation of methylene-linked indole-tetrahydroisoquinoline Compounds

Compounds QR-0266, QR-0267, QR-0268, QR-0269, QR-0271, and QR-0276 were prepared by the reaction depicted in Scheme 29 below.

Scheme 29

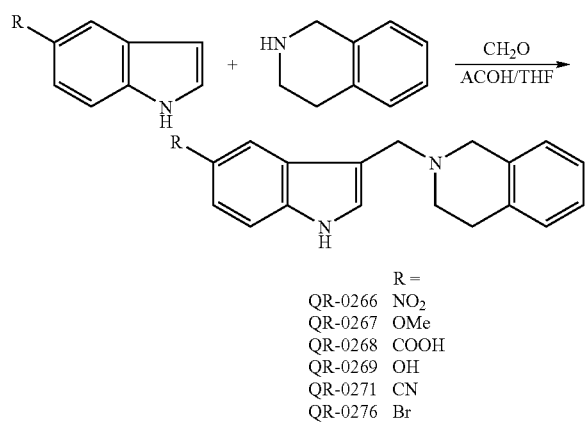

R =
QR-0266  NO₂
QR-0267  OMe
QR-0268  COOH
QR-0269  OH
QR-0271  CN
QR-0276  Br

The following General Procedure C was used.

General Procedure C

To a solution of 1,2,3,4-tetrahydroisoquinoline (4.4 mmol) in AcOH-THF (1:2, 6 mL) was added formaldehyde (0.327 mL, 4.4 mmol, 37% solution in water). After the solution was stirred for 15 min, substituted indole (4 mmol) was added. The resultant mixture was stirred at room temperature overnight. EtOAc (50 mL) was added to the mixture, and the mixture was washed with brine. After drying the organic phase with MgSO₄, solvents were removed under reduced pressure and flash chromatography, and the following compounds were recovered.

QR-0266 (88% yield), $^1$H NMR (DMSO): 2.72 (t, 2H, J=5.6), 2.80 (t, 2H, J=5.6), 3.60 (s, 2H), 3.87 (s, 2H), 7.01 (d, 1H, J=3.6), 7.06-7.12 (m, 3H), 7.55 (d, 1H, J=9.0), 7.59 (s, 1H), 8.00 (dd, 1H, J₁=9.0, J₂=2.3), 8.65 (d, 1H, J=2.2), 11.72 (s, 1H); $^{13}$C NMR (DMSO): 29.25, 50.55, 53.22, 56.04, 112.39, 114.64, 116.89, 117.02, 125.92, 126.39, 126.88, 127.19, 128.84, 128.90, 134.71, 135.40, 140.20, 140.77.

QR-0267 (59% yield), $^1$H NMR (DMSO): 3.04 (d, 1H, J=15.8), 3.22-3.33 (m, 2H), 3.68 (d, 1H, J=9.6), 3.81 (s, 3H), 4.31-4.41 (m, 2H), 4.58 (d, 2H, J=4.5), 6.81 (dd, 1H, J₁=8.8, J₂=2.2), 7.18 (d, 1H, J=7.4), 7.22-7.29 (m, 3H), 7.35 (d, J=8.8), 7.41 (d, 1H, J=1.9), 7.66 (d, 1H, J=2.5), 11.03 (s, 1H), 11.44 (s, 1H); $^{13}$C NMR (DMSO): 25.54, 47.99, 50.46, 51.28, 55.99, 101.13, 102.62, 112.38, 113.03, 127.03, 127.12, 128.05, 128.50, 128.98, 129.08, 129.95, 131.50, 132.12, 154.42.

QR-0268 (67% yield), $^1$H NMR (DMSO): 3.05 (d, 1H, J=15.4), 3.20-3.33 (m, 2H), 3.70 (s, 1H, b), 4.41 (s, 2H), 4.68 (s, 2H), 7.18-7.29 (m, 4H), 7.54 (d, 1H, J=8.5), 7.80 (d, 1H, J=8.5), 7.85 (s, 1H), 8.55 (s, 1H), 10.79 (s, 1H), 11.94 (s, 1H), 12.53 (s, 1H); $^{13}$C NMR (DMSO): 25.12, 47.78, 49.66, 51.25, 103.99, 111.64, 121.59, 122.29, 122.92, 126.53, 126.60, 126.96, 127.59, 128.45, 128.53, 130.68, 131.60, 138.48, 168.28.

QR-0269 (91% yield), $^1$H NMR (DMSO): 2.68 (t, 2H, J=5.6), 2.80 (t, 2H, J=5.6), 3.56 (s, 2H), 3.71 (s, 2H), 6.60 (dd, 1H, J₁=8.6, J₂=2.1), 7.00 (s, 2H), 7.07-7.10 (m, 3H), 7.16 (d, 1H, J=8.6), 7.18 (d, 1H, J=1.9), 8.55 (s, 1H), 10.61 (s, 1H); $^{13}$C NMR (DMSO): 29.36, 50.56, 53.98 56.13, 103.65, 110.58, 111.82, 112.08, 125.43, 125.86, 126.31, 126.83, 128.75, 128.86, 131.47, 134.84, 135.71, 150.70.

QR-0271 (88% yield). $^1$H NMR (DMSO): 2.70 (t, 2H, J=5.6), 2.80 (t, 2H, J=5.6), 3.58 (s, 2H), 3.83 (s, 2H), 7.00 (d, 1H, 6.8), 7.08-7.12 (m, 3H), 7.43 (dd, 1H, J₁=8.4, J₂=1.2), 7.53 (s, 1H), 7.54 (d, 1H, J=8.4), 8.17 (s, 1H), 11.55 (s, 1H); $^{13}$C NMR (DMSO): 29.28, 50.51, 53.08, 55.88, 100.99, 112.80, 113.21, 121.37, 174.23, 125.36, 125.89, 126.36, 126.86, 127.64, 127.83, 128.89, 134.71, 135.47, 138.67.

QR-0276 (82% yield), $^1$H NMR (DMSO): 2.68 (t, 2H, J=5.6), 2.79 (t, 2H, J=5.6), 3.57 (s, 2H), 3.77 (s, 2H), 7.00 (d, 1H, 7.0), 7.08-7.12 (m, 3H), 7.19 (dd. 1H, J₁=8.5, J₂=1.4), 7.35 (d, 1H, J=8.5), 7.37 (d, 1H, J=2.0), 7.81 (s, 1H), 11.17 (s, 1H); $^{13}$C NMR (DMSO): 29.28, 50.51, 53.42, 55.99, 111.42, 111.55, 113.90, 121.86, 123.94, 125.89, 126.35, 126.68, 126.86, 128.88, 129.84, 134.75, 135.54, 135.63.

EXAMPLE 25

Preparation of QR-0272

Compound QR-0272 was prepared by using reactions depicted in Scheme 30 below.

Scheme 30

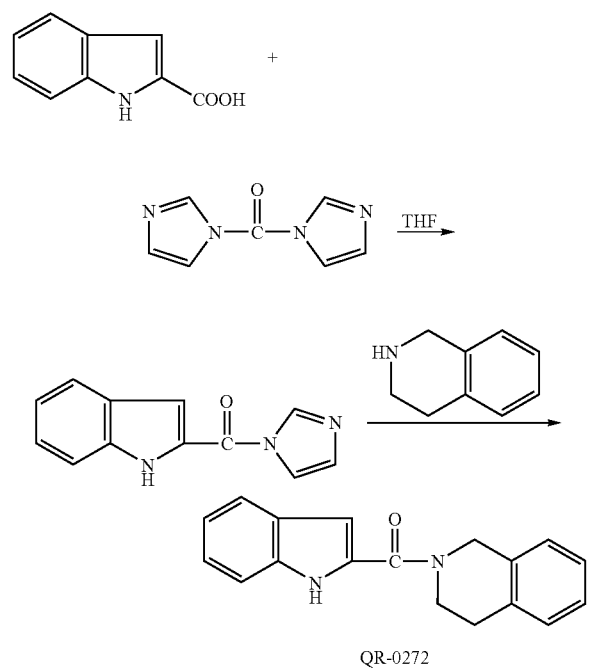

QR-0272

The following procedure was used.

1,1'-Carbonyldiimidazole (178 mg, 1.1 mmol) was added to the solution of indole-2-carboxyic acid (161 mg, 1 mmol) in dry THF (10 mL) at 0° C. After the mixture was stirred for 1 h, 1,2,3,4-tetrahydroisoquinoline (0.14 mL, 1.1 mmol) was added. The solution was stirred for 5 h at room temperature, The mixture was concentrated under vacuum and the residue purified by flash chromatography to yield the following.

QR-0272 (60% yield). $^1$H NMR (DMSO): 2.96 (s, 2H), 3.98-4.06 (m, 2H), 4.92 (s, 2H), 6.95 (s, 1H), 7.07-7.09 (m, 1H), 7.20-7.25 (m, 5H), 7.47 (d, 1H, J=8.2), 7.66 (d, 1H, J=8.0), 11.63 (s, 1H); $^{13}$C NMR (DMSO): 104.62, 112.60, 120.22, 121.95, 123.80, 126.73, 126.91, 127.06, 127.43, 128.92, 130.58, 133.84, 135.25, 136.46, 162.83.

EXAMPLE 26

Preparation of QR-274

Compound QR-274 was prepared by the reaction depicted in Scheme 31 below.

Scheme 31

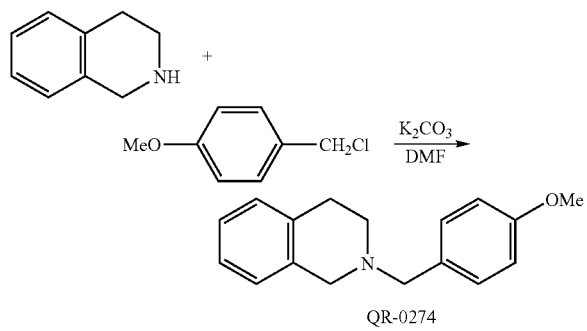

QR-0274

The following procedure was used.

To a solution of 1,2,3,4-tetrahydronisoquinoline (0.253 mL, 2 mmol) in DMF (5 mL) was added K$_2$CO$_3$ (552 mg, 4 mmol) and 4-methoxybenzylchloride (0.288 mL, 2 mmol). The resultant mixture was stirred at room temperature overnight. EtOAc (50 mL) was added to the mixture, and the mixture was washed with brine. After drying the organic layer with MgSO$_4$, evaporation of the solvents and flash chromatography yielded the following products.

QR-0274 (95% yield), $^1$H NMR (DMSO): 3.00-3.03 (m, 1H), 3.23-3.29 (2H), 3.57-3.62 (m, 1H), 3.81 (s, 3H), 4.25-4.26 (m, 2H), 4.35-4.39 (m, 2H), 7.04 (d, 2H, J=8.7), 7.18 (d, 1H, J=7.4), 7.22-7.29 (m, 3H), 7.63 (d, 2H, J=8.6); $^{13}$C NMR (DMSO): 25.29, 48.42, 51.50, 55.72, 58.21, 114.63, 122.00, 127.05, 127.10, 128.07, 128.82, 128.98, 132.07, 133.38, 160.54.

EXAMPLE 27

Preparation of QR-259

Compound QR-0259 was prepared by the reaction depicted in Scheme 32 below.

Scheme 32

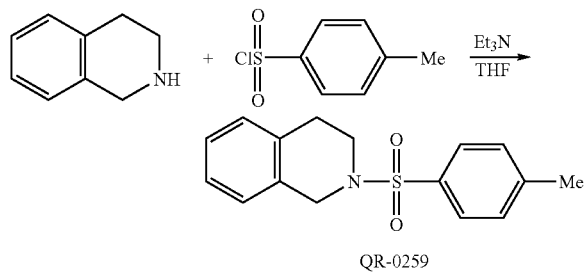

QR-0259

The following procedure was used.

To a solution of 1,2,3,4-tetrahydronisoquinoline (0.253 mL, 2 mmol) in THF (15 mL) was added Et$_3$N (0.306 mL, 2.2 mmol) and p-toluenesulfonylchloride (420 mg, 2.2 mmol). The resultant mixture was stirred at room temperature for 10 h. EtOAc (20 mL) was added and the mixture washed with brine. After drying the organic layer with MgSO$_4$, evaporation of the solvents and flash chromatography. The following compounds were recovered.

QR-0259 (92% yield), $^1$H NMR (DMSO): 2.42 (s, 3H), 2.92 (t, 2H, J=5.9), 3.35 (t, 2H, J=5.9), 4.25 (s, 2H), 7.02 (t, 1H, J=4.5), 7.07 (t, 1H, J=4.5), 7.12-7.15 (m, 2H), 7.32 (d, 2H, J=8.0), 7.73 (d, 2H, J=8.2); $^{13}$C NMR (DMSO): 21.53, 28.90, 43.73, 47.56, 126.35, 126.38, 126.75, 127.78, 128.83, 129.72, 131.70, 133.12, 133.41, 143.67.

EXAMPLE 28

Preparation of QR-0260

Compound QR-0260 was prepared by the reaction depicted in Scheme 33.

Scheme 33

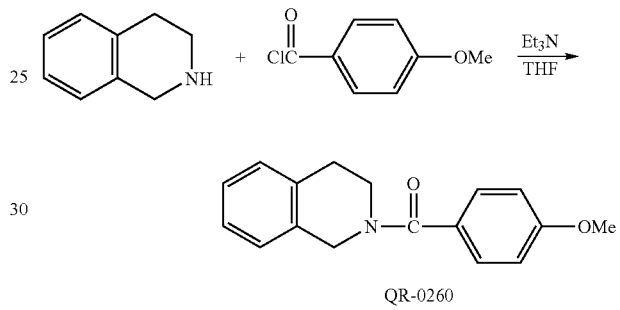

QR-0260

The following procedure was used.

To a solution of 1,2,3,4-tetrahydronisoquinoline (0.253 mL, 2 mmol) in THF (15 mL) was added Et$_3$N (0.306 mL, 2.2 mmol) and 4-anisolecarboxylic acid chloride (374 mg, 2.2 mmol). The resultant mixture was stirred at room temperature for 10 h. EtOAc (20 mL) was added and the mixture was washed with brine. After drying the organic layer with MgSO$_4$, evaporation of the solvents and flash chromatography produced the following product.

QR-0260 (89% yield), $^1$H NMR (DMSO): 2.51 (t, 2H, J=5.8), 3.67 (s, 2H, b), 3.82 (s, 3H), 4.69 (s, 2H), 7.02 (d, 2H, J=8.6), 7.19 (m, 4H), 7.44 (d, 2H, J=8.6).

EXAMPLE 29

Preparation of Bisindole Containing Fused Rings

Compounds QR-0278, QR-0288, QR-0279, QR-0291, QR-0290, and 250 were prepared by the reaction depicted in Scheme 34 below.

Scheme 34

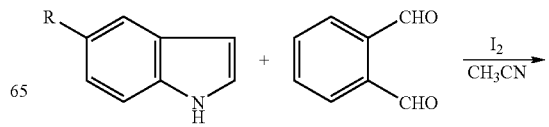

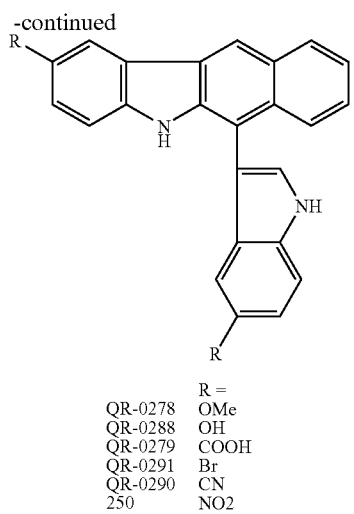

| R = | |
|---|---|
| QR-0278 | OMe |
| QR-0288 | OH |
| QR-0279 | COOH |
| QR-0291 | Br |
| QR-0290 | CN |
| 250 | NO2 |

The following General Procedure D was used.

General Procedure D

A mixture of phthalaldehyde (1 mmol), 5-substituted indole (2 mmol) and $I_2$ (0.2 mmol) in acetonitrile (10 mL) was stirred at room temperature for 30 min. to 10 hours. After completion of the reaction, aqueous $Na_2SO_3$ solution (5%, 10 mL) was added and the pH adjusted to 7 or 2 with HCl (1 N) when required. The mixture was extracted with ethyl acetate and the organic layer washed with brine and dried over $MgSO_4$. The solvent was evaporated and the residue purified by column chromatography to yield the following compounds.

QR-0278 (68% yield), $^1$H NMR (CDCl$_3$): 3.60 (s, 3H), 3.96 (s, 3H), 6.70 (s, 1H), 6.96 (d, 1H, J=2.4), 7.05 (d, 1H, J=2.4), 7.16 (s, 1H), 7.36-7.45 (m, 4H), 7.74 (s, 2H), 8.00 (s, 1H), 8.11 (d, 1H, J=7.9), 8.43 (s, 1H), 8.57 (s, 1H); $^1$H NMR (CDCl$_3$): 55.84, 56.23, 101.51, 104.67, 110.92, 111.30, 112.32, 113.42, 115.91, 118.04, 122.51, 124.94, 125.19, 127.86, 128.61, 128.83, 131.49, 154.71.

QR-0288 (65% yield), $^1$H NMR (DMSO): 6.37 (d, 1H, J=2.2), 6.70 (dd, 1H, J$_1$=8.7, J$_2$=2.3), 6.94 (d, 1H, J$_1$=8.6, J$_2$=2.4), 7.27 (d, 1H, J=8.5), 7.32-7.35 (m, 2H), 7.38 (d, 1H, J=8.7), 7.57 (d, 1H, J=2.4), 7.62 (d, 1H, J=2.3), 7.77-7.79 (m, 1H), 8.10-8.12 (m, 1H), 8.51 (s, 1H), 8.59 (s, 1H), 8.99 (s, 1H), 10.10 (s, 1H), 11.24 (s, 1H); $^{13}$C NMR (DMSO): 103.64, 106.42, 109.09, 111.81, 111.98, 112.15, 112.63, 116.56, 117.57, 122.10, 123.51, 124.58, 125.18, 125.53, 126.41, 128.05, 128.67, 129.07, 131.46, 136.84, 140.10, 150.85, 151.24.

QR-0279 (51% yield), $^1$H NMR (DMSO): 7.29 (t, 1H, J=8.1), 7.49-7.53 (m, 3H), 7.65 (s, 1H), 7.70s, 1H), 7.72, 1H), 7.81-8.84 (m, 2H), 7.97 (d, 1H, J=8.5), 8.04 (s, 1H) 8.12 (d, 1H, J=8.3), 11.75 (s, 1H), 12.01 (s, 1H), 12.23 (s, 1H); $^{13}$C NMR (DMSO): 106.13, 110.31, 112.28, 112.98, 120.88, 121.95, 122.35, 122.63, 123.21, 123.25, 124.73, 124.99, 125.52, 126.33, 126.49, 126.98, 127.41, 127.74, 128.73, 129.01, 132.99, 139.46, 140.19, 146.05, 168.01, 168.59.

QR-0291 (72% yield), $^1$H NMR (DMSO): 6.91 (d, 1H, J=1.6), 6.96 (d, 1H, J=1.5), 7.28 (t, 1H, J=7.6), 7.34 (d, 1H, J=8.7), 7.43-7.50 (m, 3H), 7.65 (d, 1H, J=8.7), 7.73 (d, 1H, J=8.8), 7.75 (d, 1H, J=2.3), 7.99 (s, 1H), 8.10 (d, 1H, J=8.3), 11.49 (s, 1H), 11.88 (s, 1H); $^{13}$C NMR (DMSO): 105.88, 110.23, 111.24, 112.44, 112.69, 114.67, 121.33, 123.06, 123.86, 124.67, 124.81, 125.00, 125.56, 126.22, 126.44, 127.17, 127.69, 128.33, 129.40, 129.60, 133.15, 135.60, 140.01, 141.91, QR-0290 (75% yield), $^1$H NMR (DMSO): 6.99 (s, 1H), 7.33-7.36 (m, 2H), 7.55 (t, 1H, J=7.5), 7.59-7.63 (m, 2H), 7.74-7.76 (m, 2H), 7.87 (d, 1H, J=8.5). 7.97 (d, 1H, J=2.3), 8.10 (s, 1H), 8.16 (d, 1H, J=8.3), 11.99 (s, 1H), 12.29 (s, 1H); $^{13}$C NMR (DMSO): 99.92, 102.18, 106.83, 111.98, 112.29, 114.12, 120.72, 120.77, 123.03, 123.53, 123.73, 124.84, 125.03, 125.96, 125.99, 126.36, 126.66, 127.22, 127.94 128.47, 128.76, 130.70, 133.38, 138.71, 139.84, 145.51.

250 (74% yield), $^1$H NMR (DMSO): 7.37 (t, 1H, J=7.5), 7.59 (t, 1H, J=7.5), 7.61 (d, 1H, J=8.9), 7.72 (d, 1H, J=2.3), 7.77 (d, 1H, J=2.2), 7.79 (d, 1H. J=8.7), 7.91 (d, 1H, J=9.1), 8.08 (d, 1H, J=2.3), 8.14 (dd, 1H, J$_1$=9.1, J$_2$=2.3), 8.17 (s, 1H), 8.20 (d, 1H, J=8.4), 8.28 (d, 1H, J=8.9), 12.14 (s, 1H), 12.52 (s, 1H); $^{13}$C NMR (DMSO): 107.61, 110.95, 113.40, 113.66, 115.96, 117.70, 118.78, 122.42, 123.50, 124.06, 124.15, 125.94, 126.22, 126.33, 126.73, 128.12, 128.86, 129.74, 133.46, 139.48, 140.24, 140.41, 141.60, 147.16.

EXAMPLE 30

Preparation of QR-0209 and QR-0214

Compounds 251, QR-0209 and QR-0214 were prepared by reactions depicted in Scheme 35 below.

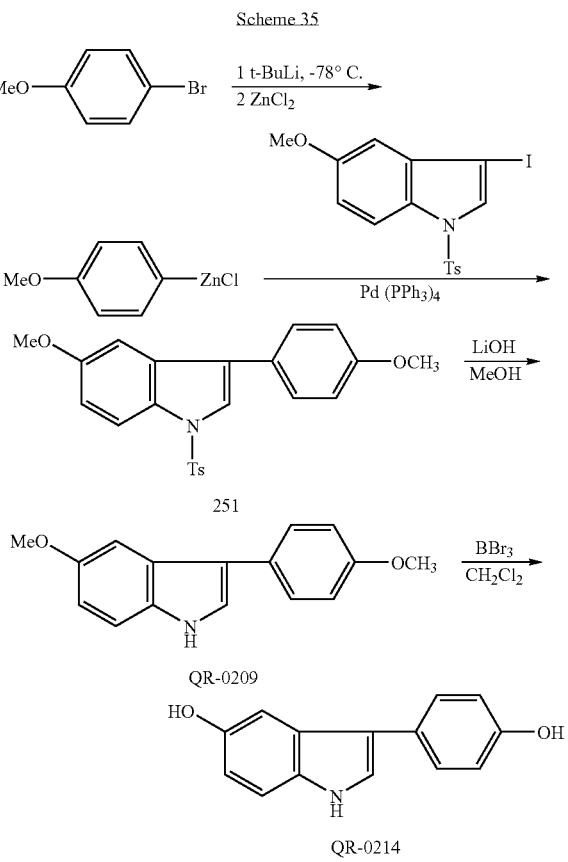

The following General Procedure E was used.

General Procedure E

A flask was charged with arylbromide (3 mmol) and dry THF (20 mL) under argon. The solution was cooled to −78° C.

and then t-BuLi (2.35 mL, 4 mmol, 1.7 M in hexanes) was added via a syringe through the septum, and the solution was stirred at −78° C. for 20 min. ZnCl$_2$ (4 mL, 4 mmol, 1 M in ether) was then added via a syringe. The mixture was stirred for 30 min. at −78° C. and the flask was removed from the cooling bath and stirred at room temperature for 30 min. This mixture was transferred to another flask containing Pd(PPh$_3$)$_4$ (0.05 mmol) catalyst and iodoindole (1 mmol) under argon. Then the mixture was stirred at 50-70° C. for 3-5 h. The reaction mixture was then cooled to roomo temperature, diluted with water (15 mL), and extracted with EtOAc(3×15 mL). The combined organic phases were dried over MgSO$_4$ and concentrated under reduced pressure. The crude material was purified by flash chromatography to yield 251. 251 (68% yield), $^1$H NMR (CDCl$_3$): 2.33 (s, 3H), 3.81 (s, 3H), 3.86 (s, 3H), 6.96 (dd, 1H, J$_1$=9.0, J$_2$=2.4), 7.00 (d, 2H, J=8.6), 7.15 (d, 1H, J=2.4), 7.21 (d, 2H, J=8.2), 7.49 (d, 2H, J=8.6), 7.57 (s, 1H), 7.76 (d, 2H, J=8.3), 7.94 (d, 1H, J=9.0).

LiOH (2 mmol) and 251 (0.5 mmol) in methanol (10 mL) were heated under reflux for 2 h. The resulting mixture was concentrated and the residue was dissolved with ethyl acetate. The solution was washed with brine and dried over MgSO$_4$. The solvent was then evaporated and the residue purified by column chromatography to yield QR-0209 (90% yield), $^1$H NMR (CDCl$_3$): 3.86 (s, 6H), 6.91 (dd, 1H, J$_1$=8.8, J$_2$=2.4), 7.00-7.02 (m, 2H), 7.26 (d, 1H, J=2.5), 7.31 (d, 1H, J=5.6), 7.33 (d, 1H, J=2.3), 7.55-7.57 (m, 21-1), 8.07 (s, 1H); $^{13}$C NMR (CDCl$_3$): 55.39, 56.02, 101.58, 112.03, 112.64, 114.33, 117.93, 122.01, 126.36, 128.24, 128.56, 131.76, 154.68, 158.10.

QR-0214 was prepared by General Procedure A of Example 14, to deprotect O-methyl group of QR-0209 to obtain QR-0214 (83% yield), $^1$H NMR (DMSO): 6.64 (dd, 1H, J$_1$=8.6, J$_2$=2.2), 6.82 (d, 2H, J=8.5), 7.12 (d, 1H, J=2.0), 7.20 (d, 1H, J=8.6), 7.38 (d, 1H, J=2.5), 7.40 (d, 2H, J=8.5), 8.64 (s, 1H), 9.22 (s, 1H), 10.85 (s, 1H); $^{13}$C NMR (DMSO): 103.55, 111.97, 112.55, 115.55, 116.00, 122.98, 126.27, 127.56, 127.89, 131.74, 151.47, 155.55.

EXAMPLE 31

Preparation of QR-0208 and QR-0215

Compounds QR-0208 and QR-0215 were prepared by reactions depicted in Scheme 36 below.

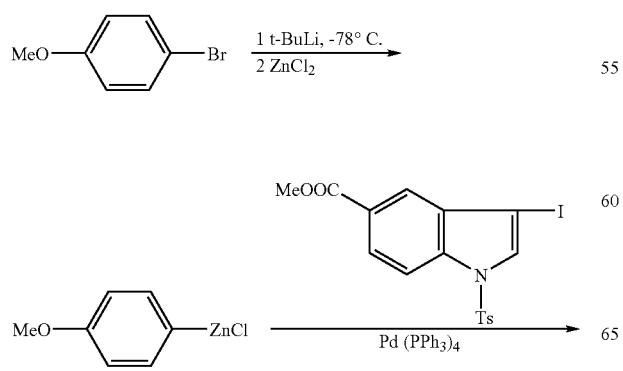

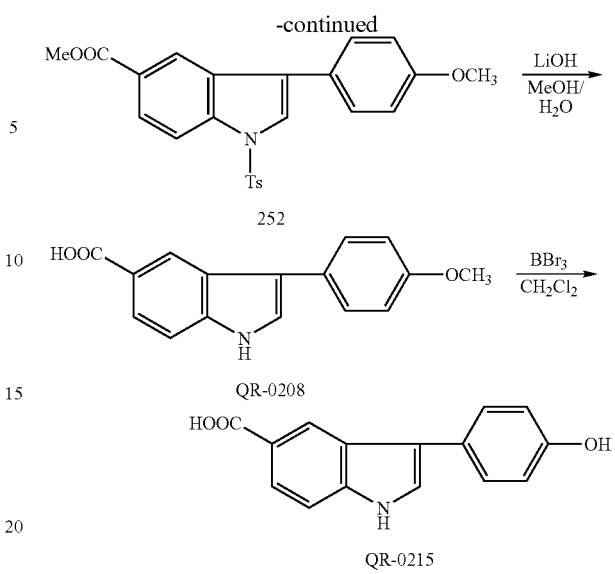

General Procedure E of Example 30 was used to yield compound 252 (71% yield). $^1$H NMR (CDCl$_3$): 2.32 (s, 3H), 3.82 (s, 3H), 3.85 (s, 3H), 7.10 (d, 2H, J=8.7), 7.41 (d, 2H, J=8.2), 7.63 (d, 2H, J=8.7), 7.98-8.01 (m, 3H), 8.11 (s, 1H), 8.14 (d, 1H, J=8.7), 8.31 (d, 1H, 0.9)

LiOH (2 mmol) and 252 (0.5 mmol) in MeOH/H$_2$O (1:1, 10 mL) were heated under reflux for 2 h. The resulting mixture was cooled to room temperature and concentrated. The residue was adjusted to pH 2 with 1N HCl. EtOAc (30 mL) was added and the resultant mixture was washed with brine and dried over MgSO$_4$. The solvent was evaporated and the residue purified by column chromatography to yield QR-0208 (89% yield), $^1$H NMR (DMSO): 3.81 (s, 3H), 7.07 (d, 2H, J=8.7), 7.51 (d, 1H, J=8.6), 7.60 (d, 2H, J=8.7), 7.69 (d, 1H, J=1.2), 7.78 (dd, 1H, J$_1$=8.6. J$_2$=1.2), 8.48 (s, 1H), 11.60 (s, 1H), 12.47 (s, 1H); $^{13}$C NMR (DMSO): 55.60, 112.10, 114.91, 117.34, 122.07, 122.36, 123.03, 124.55, 125.24, 127.97, 128.44, 139.65, 158.13, 168.83.

General Procedure A of Example 14 was used to prepare QR-0215 (82% yield), $^1$H NMR (DMSO): 6.88 (d, 2H, J=8.4), 7.47 (d, 2H, J=8.4), 7.48 (d, 1H. J=8.8), 7.61 (d, 1H, J=2.1), 7.76 (d, 1H, J=8.6), 8.44 (s, 1H), 9.36 (s, 1H), 11.52 (s. 1H), 12.42 (s, 1H); $^{13}$C NMR (DMSO): 111.52, 115.72, 117.28, 121.65, 121.71, 122.44, 123.63, 124.78, 125.79, 127.99, 139.11, 155.75, 168.37.

EXAMPLE 31A

Preparation of QR-0216 and QR-0217

Compounds 254, QR-0216 and QR-0217 were prepared by reactions depicted in Scheme 37 below.

Scheme 37

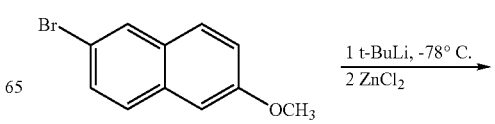

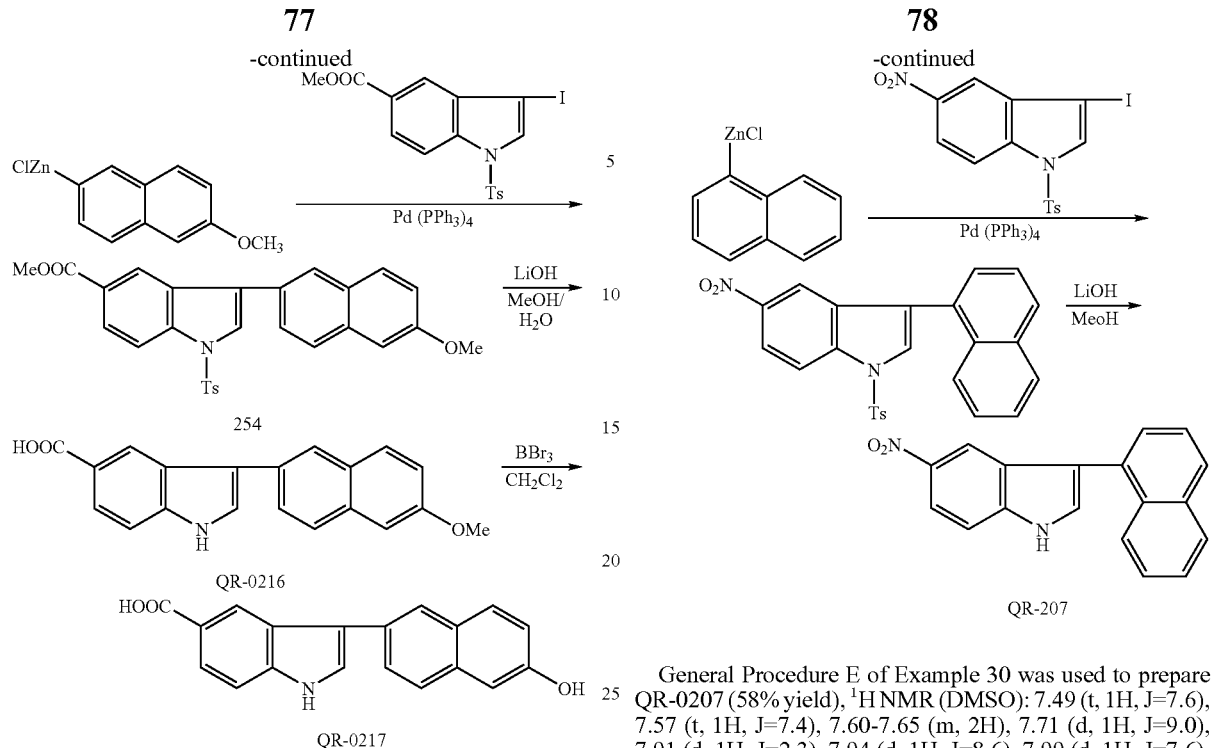

The following procedure was used.

General Procedure E of Example 30 was used to prepare 254 (64% yield), $^1$H NMR (CDCl$_3$): 2.35 (s, 3H), 3.92 (s, 3H), 3.96 (s, 3H), 7.19-7.22 (m, 2H). 7.26 (d, 2H, J=8.2), 7.67 (dd, 1H, J$_1$=8.4, J$_2$=1.6), 7.80-7.85 (m, 5H), 7.99 (s, 1H), 8.06-8.12 (m, 2H), 8.55 (s, 1H).

QR-0216 was prepared by the procedure of Example 31 for QR-0208 to yield QR-0216 (93% yield), $^1$H NMR (DMSO): 3.90 (s, 3H), 7.18 (dd, 1H, J$_1$=8.9, J$_2$=2.4), 7.34 (d, 1H, J=2.1), 7.54 (d, 1H, J=8.5), 7.80-7.83 (m, 2H), 7.87-7.92 (m, 3H), 8.10 (s, 1H), 8.61 (s, 1H), 11.72 (s, 1H), 12.48 (s, 1H); $^{13}$C NMR (DMSO): 55.67, 106.42, 112.24, 117.60, 119.29, 122.21, 122.62, 123.23, 124.71, 125.26, 125.59, 127.01, 127.76, 129.49, 129.69, 130.88, 133.20, 139.85, 157.40, 168.85.

General Procedure A of Example 14 was used to yield QR-0217 (86% yield), $^1$H NMR (DMSO): 7.10 (dd, 1H, J$_1$=8.8, J$_2$=2.3), 7.15 (d, 1H, J=2.1), 7.53 (d, 1H, J=8.5), 7.73-7.84 (m, 5H), 8.04 (s, 1H), 8.59 (s, 1H), 9.68 (s, 1H), 11.69 (s, 1H), 12.41 (s, 1H); $^{13}$C NMR (DMSO): 108.66, 111.70, 117.27, 118.89, 121.73, 122.05, 122.68, 124.29, 124.80, 124.85, 126.34, 126.60, 128.19, 129.20, 129.45, 133.04, 139.32, 154.94, 168.35.

EXAMPLE 32

Preparation of QR-0207

QR-0207 was prepared by reactions depicted in Scheme 38 below.

Scheme 38

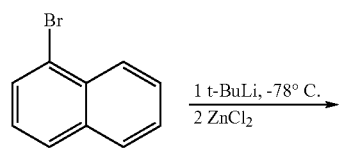

General Procedure E of Example 30 was used to prepare QR-0207 (58% yield), $^1$H NMR (DMSO): 7.49 (t, 1H, J=7.6), 7.57 (t, 1H, J=7.4), 7.60-7.65 (m, 2H), 7.71 (d, 1H, J=9.0), 7.91 (d, 1H, J=2.3), 7.94 (d, 1H, J=8.6), 7.99 (d, 1H, J=7.6), 8.04 (d, 1H, J=8.1), 8.08 (dd, 1H, J$_1$=9.0, J$_2$=2.2), 8.19 (d, 1H, J=2.0), 12.20 (s, 1H); $^{13}$C NMR (DMSO): 113.03, 116.39, 117.02, 117.36, 125.94, 126.29, 126.51, 126.74, 126.87, 127.94, 128.26, 128.92, 129.26, 131.68, 132.08, 134.18, 139.90, 141.43.

EXAMPLE 33

Preparation of Bisindoles Containing 7-Azaindole

Bisindoles containing 7-azaindole were prepared by reactions depicted in Scheme 39 below.

Scheme 39

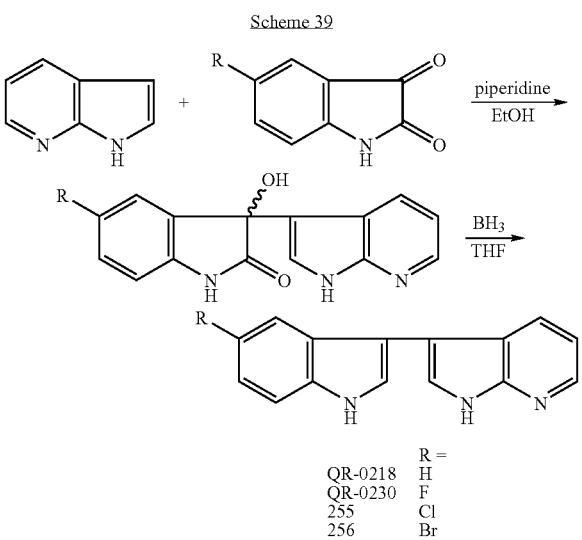

| | R = |
|---|---|
| QR-0218 | H |
| QR-0230 | F |
| 255 | Cl |
| 256 | Br |

The following General Procedure F was used.

General Procedure F

A solution of 5-substituted isatin (5 mmol), 7-azaindole (5 mmol), and piperidine (0.5 mmol) was stirred in ethanol at 45° C. overnight. When TLC indicated the reaction was complete, the reaction mixture was concentrated and the product rinsed with EtOAc/hexane. The product was used in the next step without further purification.

To a solution of the product (4 mmol) in dry THF at 0° C. was added BH$_3$.THF (10 mL, 10 mmol) dropwise over 10 min. The solution was stirred at room temperature overnight, and then quenched by the dropwise addition of MeOH (30 mL). The solvent was removed under vacuum and a solution of acetic acid and 1 M HCl (1:1, 30 mL) was added. The mixture was stirred for 2 h to remove any BH$_3$ bonded at the pyridine nitrogen. K$_2$CO$_3$ was added to adjust the pH to 7.0, and the aqueous solution was extracted with ethyl acetate (3×50 mL). The combined organic phase was dried with MgSO$_4$, filtered and concentrated under vacuum. The residue was purified by flash chromatography to yield the following compounds.

QR-0218 (68% yield). $^1$H NMR (DMSO): 7.06-7.17 (m, 3H), 7.45 (d, 1H, J=8.1), 7.70 (d, 1H, J=2.3), 7.75 (d, 1H, J=2.3), 7.80 (d, 1H, J=7.9), 8.18 (dd, 1H, J$_1$=7.8, J$_2$=0.8), 8.27 (dd, J$_1$=4.6, J$_2$=1.3), 11.20 (s, 1H), 11.67 (s, 1H); $^{13}$C NMR (DMSO): 109.24, 109.50, 112.10, 115.81, 118.72, 119.48, 119.97, 121.81, 122.39, 122.62, 126.26, 128.27, 136.89, 143.17, 149.18.

QR-0230 (65% yield). $^1$H NMR (DMSO): 7.00 (t, 1H, J=9.1), 7.12 (q, 1H, J=4.6, J=3.2), 7.45 (q, 1H J=4.6, J=4.2), 7.46 (d, 1H, J=10.2), 7.79 (s, 2H), 8.18 (d, 1H, J=7.8), 8.27 (d, 1H, J=4.6), 11.32 (s, 1H), 11.71 (s, 1H); $^{13}$C NMR (DMSO): 104.54, 104.73, 108.70, 109.84, 109.88, 110.08, 112.99, 113.07, 115.86, 118.56, 122.53, 124.72, 126.29, 126.36, 128.17, 133.56, 143.23, 149.18, 156.74, 158.58.

255 (60% yield). $^1$H NMR (DMSO): 7.11-7.16 (m, 2H), 7.47 (d, 1H, J=8.6), 7.77-7.78 (m, 2H), 7.81 (d, 1H, J=2.3), 8.17 (d, 1H, J=7.8), 8.27 (dd, 1H, J$_1$=4.6, J$_2$=1.3), 11.43, (s, 1H), 11.73 (s, 1H); $^{13}$C NMR (DMSO): 108.39, 109.43, 113.64, 115.91, 118.61, 119.05, 121.82, 122.81, 124.24, 124.48, 127.32, 128.10, 135.34, 143.28, 149.19.

256 (62% yield), $^1$H NMR (DMSO): 7.14 (t, 1H, J=4.6, J=3.3), 7.28 (d, 1H, J=8.6), 7.44 (d, 1H, J=8.6), 7.78 (d, 1H, J=2.2), 7.82 (s, 1H), 7.92 (d, 1H. J=1.5), 8.17 (d, 1H, J=7.8), 8.29 (d, 1H, J=4.5), 11.46 (s, 1H), 11.75 (s, 1H); $^{13}$C NMR (DMSO): 108.35, 109.32, 112.20, 114.12, 115.92, 118.63, 122.03, 122.86, 124.33, 124.36, 128.08, 135.56, 143.29, 149.19.

EXAMPLE 34

Preparation of QR-0241

Compound QR-0241 was prepared using the reaction depicted in Scheme 40 below.

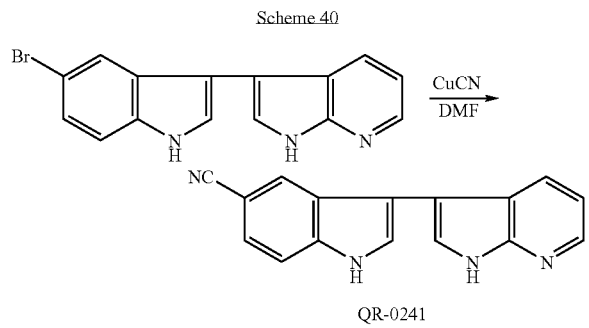

The following General Procedure G was used.

General Procedure G

A bromoindole-containing compound (1 mmol), copper cyanide (2-4 mmol) and DMF (5 mL) were stirred under argon at 150 ° C. for 3-5 h. The mixture was then cooled to room temperature and water (25 mL) added. The aqueous layer was extracted with EtOAc (3×25 mL) and the combined organic layer dried with MgSO$_4$, filtered and concentrated under vacuum. The residue was purified by flash chromatography to yield QR-0241 (52% yield). $^1$H NMR (DMSO): 7.15 (q, 1H, J=7.5, J=4.6), 7.51 (dd, 1H, J$_1$=8.4, J$_2$=1.3), 7.62 (d, 1H, J=8.4), 7.96 (d, 1H, J=2.2), 7.98 (d, 1H, J=2.4), 8.23 (d, 1H, J=7.5), 8.29 (dd, 1H, J$_1$=4.6, J$_2$=1.3), 8.35 (s, 1H), 11.83 (s, 2H); $^{13}$C NMR (DMSO): 101.62, 107.71, 110.74, 113.34, 116.03, 118.45, 121.36, 123.36, 124.63, 125.00, 125.78, 125.91, 128.12, 138.51, 143.37, 149.20.

EXAMPLE 35

Preparation of QR-0239 and QR-0240

Compounds QR-0239 and QR-0240 were prepared by the reaction depicted in Scheme 41 below.

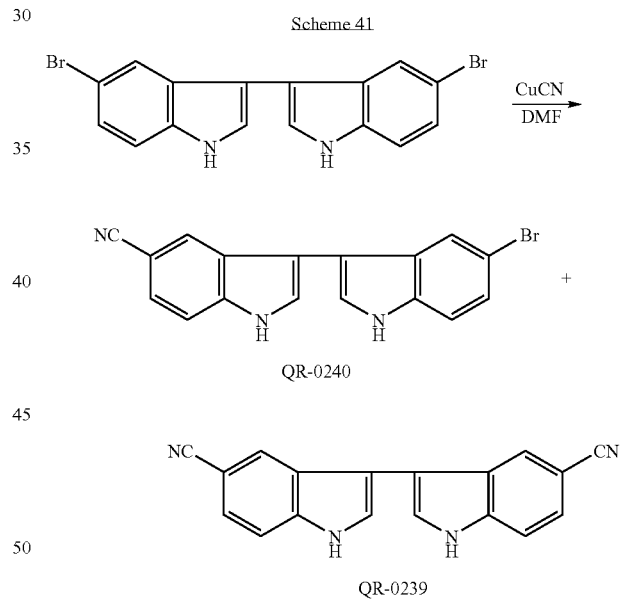

General Procedure G of Example 34 was used to yield the following compounds.

QR-239 (15% yield). $^1$H NMR (DMSO): 7.52 (dd, 2H, J$_1$=8.4, J$_2$=1.4), 7.63 (d, 2H, J=8.4), 8.09 (d, 2H, J=2.3), 8.35 (s, 2H), 11.88 (s, 2H); $^{13}$C NMR (DMSO): 101.72, 109.97, 113.37, 121.36, 124.68, 125.56, 125.64, 125.95, 138.55.

QR-240 (37% yield). $^1$H NMR (DMSO): 7.28 (dd, 1H, J$_1$=8.6, J$_2$=1.8), 7.44 (d, 1H, J$_1$=8.6), 7.50 (dd, 1H, J$_1$=8.4, J$_2$=1.4), 7.62 (d, 1H, J=8.4), 7.91 (d, 1H, J=2.4), 7.92 (d, 1H, J=1.5), 7.94 (d, 1H, J$_2$=2.3), 8.28 (s, 1H), 11.51 (s, 2H), 11.79 (s, 1H); $^{13}$C NMR (DMSO): 101.53, 108.53, 110.56, 112.29, 113.36, 114.14, 121.38, 121.89, 124.42, 124.57, 124.82, 125.10, 125.61, 126.10, 128.03, 135.57, 138.51.

EXAMPLE 36

Preparation of QR-0238 and QR-0276

Compounds QR-0238 and QR-0276 were prepared by reactions depicted in Scheme 42 below.

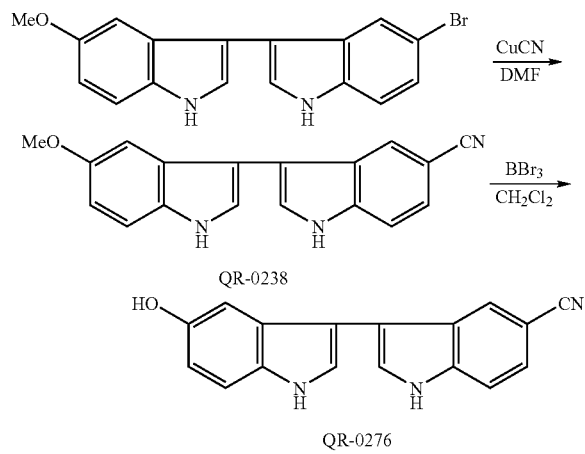

General Procedure E of Example 30 was used to yield QR-0238 (55% yield). $^1$H NMR (DMSO): 3.80 (s, 3H), 6.83 (d, 1H, J=7.7), 7.22 (s, 1H), 7.36 (d, 1H, J=8.1), 7.50 (d, 1H, J=7.5), 7.62 (d, 1H, J=7.8), 7.77 (s, 1H), 7.89 (s, 1H), 8.26 (s, 1H), 11.13 (s, 1H), 11.73 (s, 1H); $^{13}$C NMR (DMSO): 55.89, 101.33, 101.65, 108.49. 111.55, 112.00, 112.79, 113.30, 121.43, 123.88, 124.44, 124.59, 125.74, 126.25, 126.56, 132.05, 138.50, 154.10.

General Procedure A of Example 14 was used to yield QR-0276 (53% yield). $^1$H NMR (DMSO): 6.69 (dd, 1H, $J_1$=8.6, $J_2$=2.0), 7.09 (d, 1H, J=1.8), 7.26 (d, 1H, J=8.6), 7.49 (dd, $J_1$=8.4, $J_2$=1.1), 7.61 (d, 1H, J=8.4), 7.68 (s, 1H, J=2.2), 7.73 (d. 1H, J=2.1), 8.22 (s, 1H), 8.58 (s, 1H), 10.97 (s, 1H), 11.71 (s, 1H); $^{13}$C NMR (DMSO): 101.25, 103.70, 107.84, 111.89, 112.18, 112.47, 113.31, 121.45, 123.65, 124.25, 124.39, 125.79, 126.27, 127.05, 131.43, 138.45, 151.38.

EXAMPLE 37

Preparation of QR-0235 and QR-0236

Compounds QR-0235 and QR-0236 were prepared by reactions depicted in Scheme 43 below.

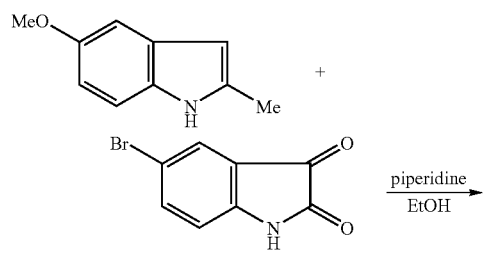

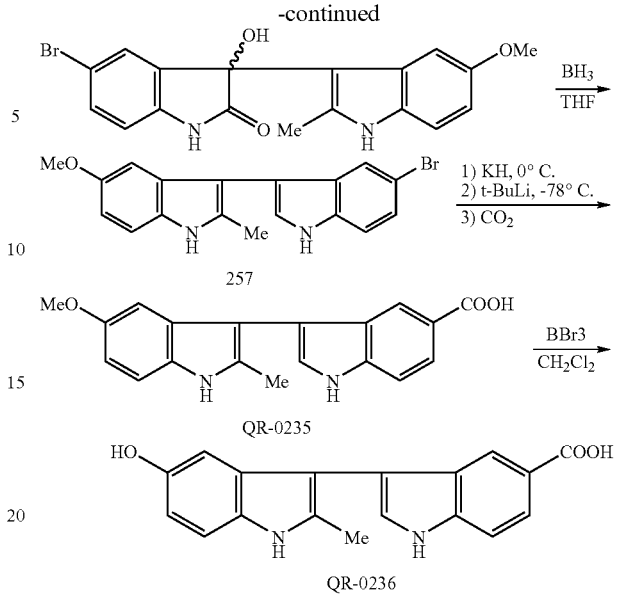

The following procedure was used.

A solution of 5-bromoisatin (5 mmol), 5-methoxy-2-methylindole (5 mmol), and piperidine (0.5 mmol) were stirred in ethanol at 45° C. overnight. When TLC indicated the reaction was complete, the reaction mixture was concentrated and the product washed with EtOAc and hexane. The product was used in the next step without further purification. To a solution of the product (3 mmol) in dry THF at 0° C. was added $BH_3$.THF (7.5 mL, 7.5 mmol) dropwise over 10 min. The solution was stirred at room temperature overnight, and then quenched by the dropwise addition of MeOH (30 mL). The solvent was removed under reduced pressure and the residue purified by flash chromatography to yield 257 (48% yield). $^1$H NMR ($CDCl_3$): 2.42 (s, 3H), 3.76 (s, 3H), 6.83 (dd, 1H, $J_1$=8.7, $J_2$=2.5), 6.93 (d, 1H, J=2.3), 7.25 (d, 2H, J=4.0), 7.30-7.34 (m, 2H), 7.69 (s, 1H), 7.90 (s, 1H), 8.28 (s, 1H).

Bromoindole species 257 (1.0 mmol) was dissolved in dry THF (10 mL) and added dropwise to a suspension of KH (2.2 eq., 35 wt. % in oil) in THF (10 mL) at 0° C. After 20 min., the reaction was cooled to −78° C. and t-BuLi (3 eq., 1.7M in pentane) was added dropwise. After a further 20 min. of stirring, a large excess of $CO_2$ gas was added via a balloon. After stirring 2 h, the reaction was quenched by adding water (10 mL) and HCl (1N) until a pH of 2 was reached. The aqueous layer was extracted with EtOAc (2×20 mL) and the organic layer dried with $MgSO_4$. After concentration, product was purified by flash column chromatography to yield QR-0235 (46% yield). $^1$H NMR (DMSO): 2.39 (s, 3H), 3.65 (s, 3H), 6.71 (dd, 1H, $J_1$=8.7, $J_2$=2.4), 6.81 (d, 1H, J=2.3), 7.25 (d, 1H, J=8.7), 7.48 (d, 1H, J=2.2), 7.52 (d, 1H, J=8.6), 7.77 (dd, 1H, $J_1$=8.6, $J_2$=1.6), 8.15 (s, 1H), 10.94 (s, 1H), 11.52 (s, 1H), 12.28 (s, 1H); $^{13}$C NMR (DMSO): 11.92, 55.60, 101.08, 105.72, 110.49, 110.98, 111.72, 111.85, 121.46, 122.69, 123.18, 125.28, 127.07, 128.98, 130.96, 133.52, 139.24, 153.66, 168.90.

General Procedure A of Example 14 was used to yield QR-0236 (67% yield). $^1$H NMR (DMSO): 2.35 (s, 3H), 6.56 (d, 1H, J=8.5), 6.66 (d, 1H, J=1.6), 7.14 (d, 1H, J=8.5), 7.42 (d, 1H, J=1.9), 7.50(d, 1H, J=8.5), 7.76 (d, 1H, J=8.5), 8.08 (s, 1H), 8.45 (s, 1H), 10.76 (s, 1H), 11.50 (s, 1H), 12.32 (s, 1H); $^{13}$C NMR (DMSO): 12.84, 103.16, 105.04, 110.67, 111.23, 111.31, 111.77, 121.47, 122.64, 123.12, 125.22, 127.26, 129.59, 130.31, 133.26, 139.19, 150.97, 168.94.

EXAMPLE 38

Preparation of QR-0252 and QR-0253

Compounds QR-0252 and QR-0253 were prepared by reactions depicted in Scheme 44 below.

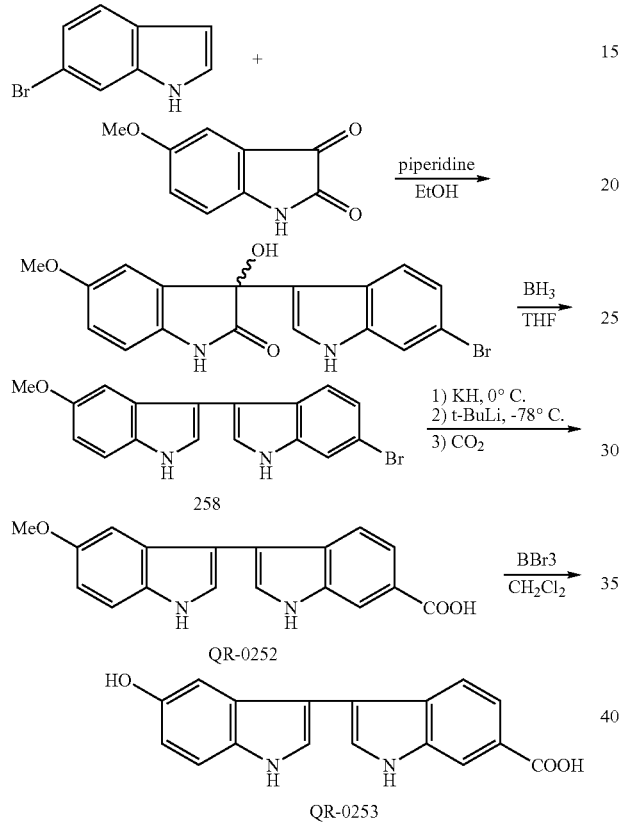

Preparation of 258 followed the same procedure as that for 257 in Example 37 to yield 258 (70% yield). $^1$H NMR (DMSO): 6.81 (dd, 1H, $J_1$=8.7, $J_2$=2.4), 7.18-7.20 (m, 2H), 7.35 (d, 1H, J=8.7), 7.59 (d, 1H, J=2.4), 7.64 (d, 1H, J=1.7), 7.68 (d, 1H, J=2.3), 7.72 (d, 1H, $J_2$=8.5), 11.04 (s, 2H), 11.27 (s, 1H).

Preparation of QR-0252 followed the same procedure as that for QR-0235 of Example 37 to yield QR-0252 (66% yield). $^1$H NMR (DMSO): 3.78 (s, 3H), 6.82 (dd, 1H, $J_1$=8.7, $J_2$=2.4), 7.20 (d, 1H, J=2.3), 7.35 (d, 1H, J=8.7), 7.62 (d, 1H, J=2.3), 7.67 (dd 1H, $J_1$=8.4, $J_2$=1.4), 7.82 (d, 1H, J=8.4), 7.88 (d, 1H, J=2.4), 8.11 (s, 1H), 11.05 (s, 2H), 11.50 (s, 1H), 12.58 (1H); $^{13}$C NMR (DMSO):55.86, 101.74, 109.30, 110.89, 111.92, 112.74, 114.17, 119.65, 120.21, 123.43, 123.78, 125.92 126.74, 129.69, 132.02, 136.14, 153.97, 168.84.

General Procedure A of Example 14 was used to prepare QR-0253 (70% yield). $^1$H NMR (DMSO): 6.68 (dd, 1H, $J_1$=8.6, $J_2$=2.2), 7.08 (d, 1H, J=2.1), 7.25 (d, 1H, J=8.6), 7.55 (d, 1H J=2.3), 7.67 (dd, 1H, $J_1$=8.4, $J_2$=1.4), 7.75 (d, 1H, J=2.3), 7.80 (d, 1H, J=8.4), 8.10 (s, 1H), 8.64 (s, 1H), 10.90 (s, 2H), 11.48 (s, 1H), 12.48 (1H); $^{13}$C NMR (DM50): 103.87, 108.65, 111.21, 112.09, 112.39, 114.14, 119.73, 120.15, 123.18, 123.81, 125.56, 127.22, 129.68, 131.41, 136.09, 151.25, 168.87.

EXAMPLE 39

Preparation of QR-0303 and QR-0289

Compounds QR-0303 and QR-0289 were prepared by reactions depicted in Scheme 45 below.

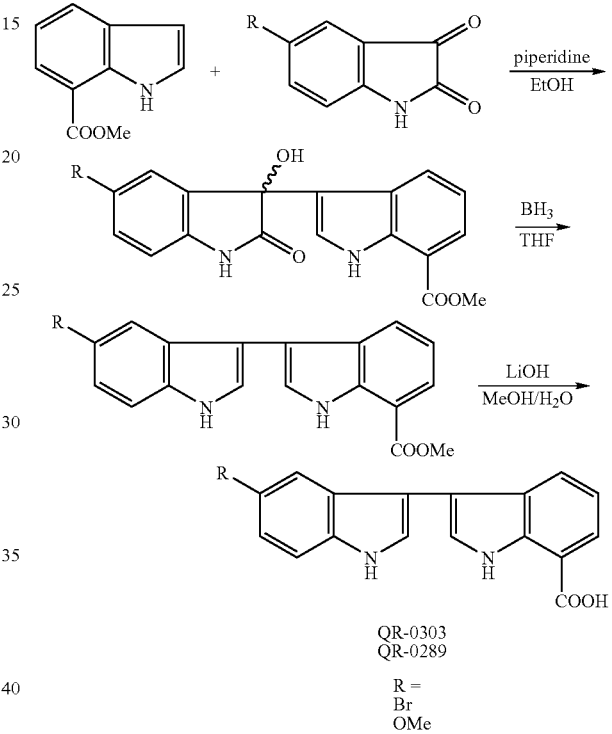

The procedure was as follows.

A solution of 5-substituted isatin (5 mmol), indole-7-carboxylic acid methyl ester (5 mmol), and piperidine (0.5 mmol) were stirred in ethanol at room temperature for 2-4 d. When TLC indicated the reaction was complete. the reaction mixture was concentrated and the product washed with EtOAc and hexane. The product was used in the next step without further purification. To a solution of the product (4 mmol) in dry THF at 0° C. was added BH$_3$.THF (10 mL, 10 mmol) dropwise over 10 min. The solution was stirred at room temperature overnight, and then quenched by the dropwise addition of MeOH (30 mL). The solvent was removed under vacuum, giving crude product which was stirred with LiOH (10 mmol) in MeOH/H$_2$O (1:1, 40 mL) at 70° C. for 2 h. The mixture was concentrated and the pH adjusted to 2 with 1N HCl. The aqueous layer was extracted with EtOAc (2×20 mL) and the organic layer dried with MgSO$_4$. Final product was purified by flash column chromatography to yield the following compounds.

QR-0303 (32% yield). $^1$H NMR (DMSO): 7.19 (t, 1H, J=7.7), 7.28 (d, 1H, J=8.6), 7.45 (d, 1H, J=8.6), 7.62 (d, 1H, J=2.3), 7.76 (d, 1H, J=2.3), 7.79 (d, 1H, J=1.7), 7.83 (d, 1H, J=8.6), 8.02 (d, 1H, J=7.8), 11.15 (s, 1H), 11.49 (s, 1H), 13.12 (s, 1H); $^{13}$C NMR (DMSO): 109.09, 109.79, 112.07, 114.15, 114.22, 119.05, 121.74, 123.96, 124.30, 124.57, 124.78, 125.40, 128.13, 128.33, 135.53, 135.55, 168.47.

QR-0289 (27% yield). $^1$H NMR (DMSO): 3.76 (s, 3H), 6.82 (d, 1H, J=8.7), 7.14 (d, 1H, J=2.0), 7.19 (t, 1H, J=7.6), 7.36 (d, 1H, J=8.7), 7.60 (d, 1H, J=2.2), 7.63 (d, 1H, J=2.2), 7.82 (d, 1H, J=7.3), 8.03 (d, 1H, J=7.8), 11.11 (s, 2H), 13.10 (s, 1H); $^{13}$C NMR (DMSO): 55.82, 101.60, 109.10, 110.72, 111.83, 112.81, 114.13, 118.85, 123.58, 123.62, 124.64, 125.54, 126.87, 128.31, 132.06, 135.56, 153.97, 168.52.

EXAMPLE 40

Preparation of QR-0254

Compound QR-0254 was prepared by reactions depicted in Scheme 46 below.

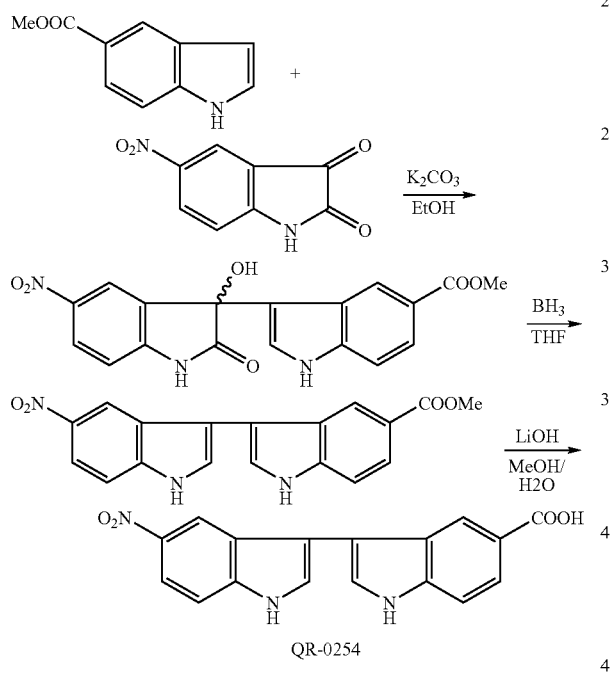

QR-0254

The following procedure was used.

A solution of 5-nitroisatin (5 mmol), indole-5-carboxylic acid methyl ester (5 mmol), and K$_2$CO$_3$ (10 mmol) were stirred in ethanol at room temperature overnight. When TLC indicated the reaction was complete, the reaction mixture was concentrated. The product was washed with EtOAc and hexane. The product was used in the next step without further purification. To a solution of the product (4 mmol) in dry THF at 0° C. was added BH$_3$.THF (10 mL, 10 mmol) dropwise over 10 min. The solution was stirred at room temperature overnight, then quenched by the dropwise addition of MeOH (30 mL). The solvent was removed under vacuum, giving crude product which was stirred with LiOH (10 mmol) in MeOH/H$_2$O (1:1, 40 mL) at 70° C. for 2 h. The mixture was concentrated and adjusted pH to 2 with 1N HCl. The aqueous layer was extracted with EtOAc (2×20 mL) and the organic layer was dried with MgSO$_4$. Final product was purified by flash column chromatography to yield QR-0254 (38% yield). $^1$H NMR (DMSO): 7.56 (d, 1H, J=8.5), 7.67 (d, 1H, J=9.0), 7.81 (dd, 1H, J$_1$=8.6, J$_2$=1.4), 7.88 (d, 1H, J=2.3), 7.93 (d, 1H, J=2.2), 8.08 (dd, 1H, J$_1$=9.0, J$_2$=2.2), 8.40 (s, 1H), 8.65 (d, 1H, J=2.1), 11.69 (s, 1H), 12.02 (s, 1H), 12.46 (s, 1H); $^{13}$C NMR (DMSO): 109.80, 112.03, 112.22, 112.71, 116.94, 117.31, 122.25, 122.28, 123.27, 124.88, 125.91, 126.06, 126.50, 139.36, 139.95, 141.25, 168.83.

EXAMPLE 41

Preparation of QR-0251

Compound QR-0251 was prepared by reactions depicted in Scheme 47 below.

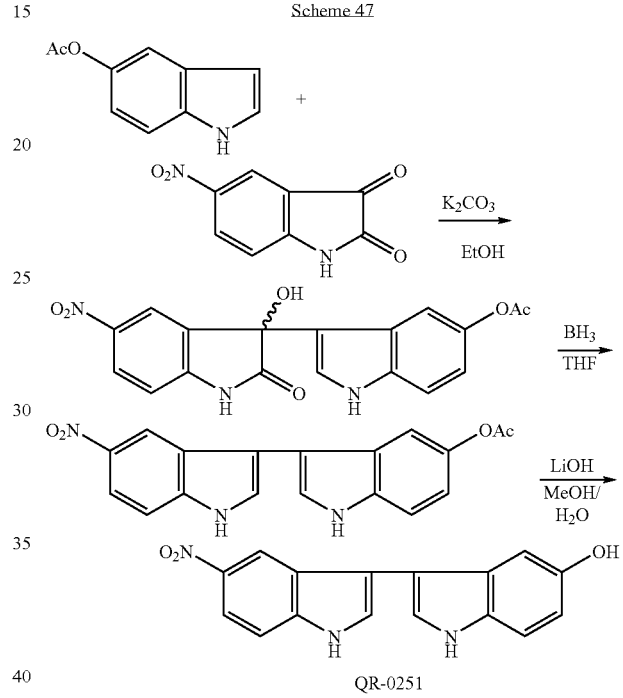

QR-0251

Procedures of Example 40 were used to yield QR-0251 (18% yield). $^1$H NMR (DMSO): 6.70 (d, 1H, J=8.6), 7.06 (d, 1H, J=2.0), 7.28 (d, 1H, J=8.6), 7.61-7.63 (m, 2H), 7.77 (d, 1H, J=2.2), 8.06 (d, 1H, J=8.8), 8.63 (d, 1H, J=2.1), 8.7 (s, 1H), 11.01 (s, 1H), 11.92 (s, 1H); $^{13}$C NMR (DMSO): 103.54, 107.61, 112.32, 112.53, 112.57, 113.51, 117.09, 117.21, 123.66, 125.60, 125.94, 127.14, 131.44, 139.86, 141.00, 151.47.

EXAMPLE 42

Preparation of QR-0327

Compound QR-0327 was prepared by reactions depicted in Scheme 48 below.

Scheme 48

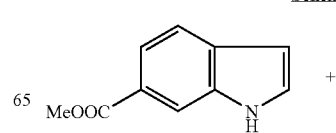

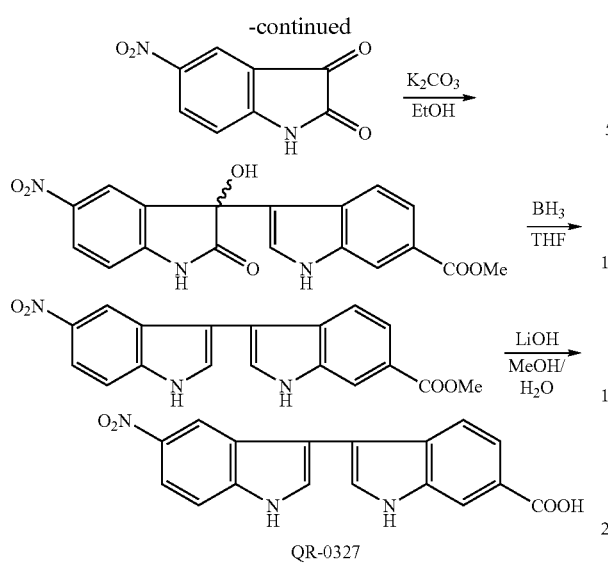

1H, J=9.0), 7.72(d, 1H, J=2.5), 7.86 (d, 1H, J=7.0), 7.97 (d, 1H, J=2.3), 8.05-8.09 (m, 2H), 8.62 (d, 1H, J=2.1), 11.25 (s, 1H), 12.02 (s, 1H), 13.08 (s, 1H); $^{13}$C NMR (DMSO): 108.97, 112.16, 112.67, 114.31, 116.81, 117.29, 119.32, 124.49, 124.97, 125.29, 125.88, 126.55, 128.01, 135.59, 139.96, 141.22, 168.38.

EXAMPLE 44

Preparation of QR-0311

Compound QR-0311 was prepared by reactions depicted in Scheme 50 below.

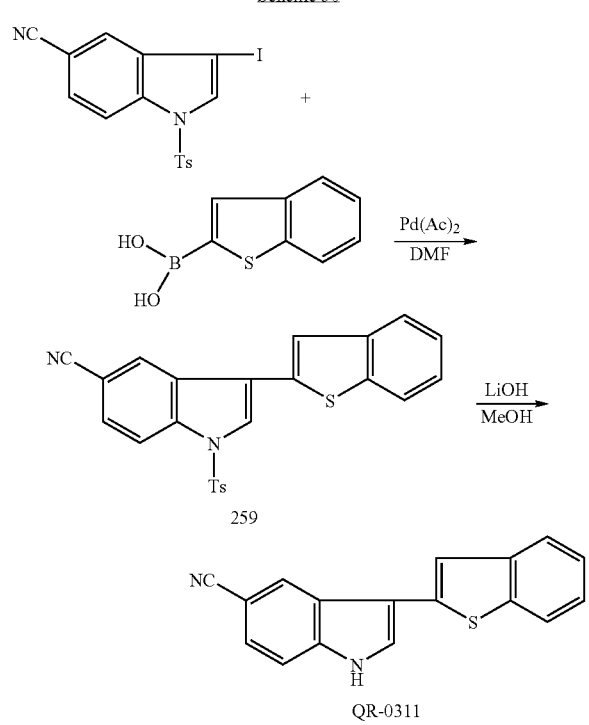

The procedure of Example 40 was used to yield QR-0327 (36% yield). $^{1}$H NMR (DMSO): 7.64 (d, 1H, J=9.0), 7.71 (dd, 1H, $J_1$=8.4, $J_2$=1.0), 7.83 (d, 1H, J=8.4), 7.95 (d, 1H, J=1.6), 8.00 (d, 1H, J=2.4), 8.07 (dd, 1H, $J_1$=9.0, $J_2$=2.1), 8.15 (s, 1H), 8.67 (d, 1H, J=2.0), 11.69 (s, 1H), 12.03 (s, 1H), 12.57 (s, 1H); $^{13}$C NMR (DMSO): 109.02, 112.38, 112.63, 114.34, 117.04, 117.25, 119.33, 120.62, 124.41, 125.81, 126.41, 126.77, 129.42, 136.25, 139.93, 141.23, 168.79.

EXAMPLE 43

Preparation of QR-0295

Compound QR-0295 was prepared by reactions depicted in Scheme 49 below.

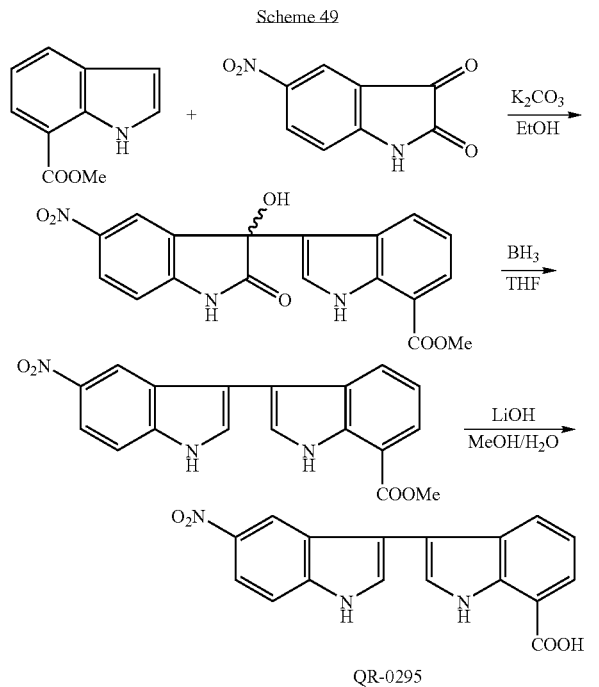

Procedures of Example 40 were used to yield QR-0295 (5% yield). $^{1}$H NMR (DMSO): 7.22 (t, 1H, J=7.7), 7.64 (d, The following General Procedure H was used.

General Procedure H

Arylbromide or aryliodide (1 mmol), boric acid (1.2 mmol) and Pd(OAc)$_2$ (0.05 mmol) in DMF (5 mL) were stirred under argon at 60-90° C. for 5-16 h. The mixture was then cooled to room temperature, ethyl acetate (50 mL) was added and the mixture washed with brine 3 times (50 mL). The organic layer was dried with MgSO$_4$ and concentrated. The residue was purified by flash column chromatography.

General Procedure H was used to yield 259 (63% yield). $^{1}$H NMR (CDCl$_3$): 2.38 (s, 3H), 7.30 (d, 2H, J=8.4), 7.37-7.41 (m, 2H), 7.55 (s, 1H), 7.64 (d, 1H, J=8.6), 7.82-8-7.86 (m, 4H), 7.96 (s, 1H), 8.14 (d, 1H J=8.6), 8.31 (s, 1H).

LiOH (2 mmol) and 259 (0.5 mmol) in methanol (10 mL) were stirred at room temperature for 2 h. The mixture was then concentrated and the residue dissolved in ethyl acetate. The solution was washed with brine and the organic layer dried over MgSO$_4$. The solvent was evaporated and the residue purified by column chromatography to yield QR-0311 (82% yield). $^{1}$H NMR (DMSO): 7.32 (t, 1H, J=7.2), 7.39 (t, 1H, J=7.2), 7.58 (d, 1H, J=8.4), 7.67 (d, 1H, J=8.4), 7.85 (d, 1H, J=7.9), 7.87 (s, 1H), 7.95 (d, 1H, J=7.9), 8.06 (d, 1H, J=2.5), 8.55 (s, 1H), 11.12 (s, 1H); $^{13}$C NMR (DMSO): 102.94, 111.12, 114.04, 119.21, 120.96, 122.55, 123.53, 124.36, 124.83, 125.08, 125.35, 125.46, 127.72, 137.07, 137.83, 139.02, 141.26.

EXAMPLE 45

Preparation of QR-0310

Compound QR-0310 was prepared by the reaction depicted in Scheme 51 below.

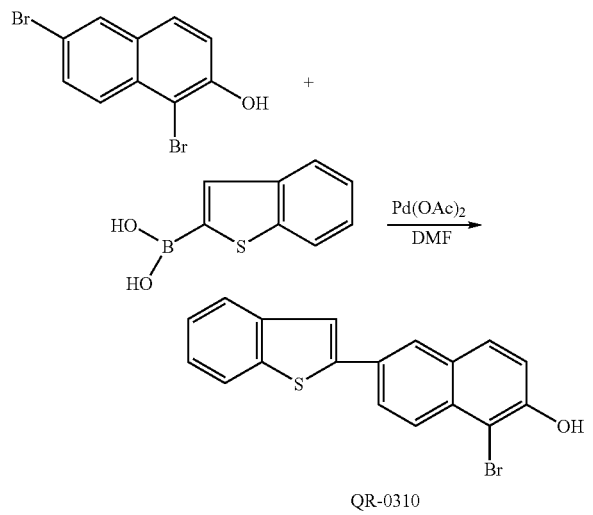

General Procedure H of Example 44 was used to yield QR-0310 (50% yield). $^1$H NMR (DMSO): 7.33-7.43 (m, 3H), 7.87-8.11 (m, 6H), 8.25 (s, 1H), 10.72 (s, 1H); $^{13}$C NMR (DMSO): 104.85, 119.62, 120.67, 122.95, 124.21, 125.18, 125.36, 125.71, 126.25, 126.28, 129.12, 129.20, 129.87, 133.01, 139.06, 141.03, 143.40, 153.56.

EXAMPLE 46

Synthesis of QR-0292 and QR-0306

Compound QR-0292 was prepared by using the reaction depicted in the following Scheme:

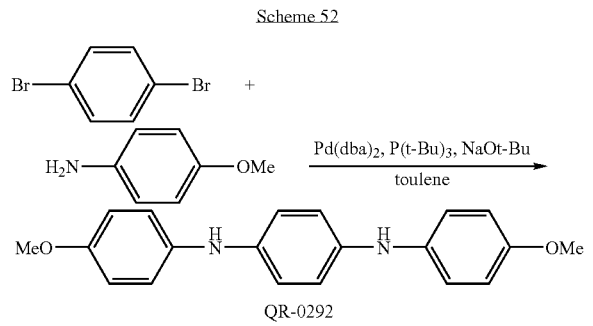

The following procedure was used.

A mixture of 1,4-dibromobenzene (0.236 g, 1.00 mmol), 4-methoxyaniline (0.369 g, 3.00 mmol), Pd(dba)$_2$ (28.8 mg, 0.05 mmol), P(t-Bu)$_3$ (8.1 mg, 0.04 mmol) and sodium tert-butoxide (288 mg, 3.00 mmol) in dry toluene (10 mL) were refluxed together under an argon atmosphere. The reaction was monitored by thin layer chromatography. Upon completion, the mixture was cooled to room temperature, distilled water was added, and the mixture extracted with ethyl acetate (3×30 mL). The combined ethyl acetate extracts were washed with brine before being dried over MgSO$_4$. The solution was concentrated under reduced pressure, and the product purified by flash column chromatography (20% EtOAc/hexanes) to yield QR-0292 (51 mg, 16%) as a colorless solid. $^1$H NMR (DMSO-d$_6$): δ 7.46 (2H, s), 6.91 (4H, d, J=8.9 Hz), 6.88 (4H, s), 6.80 (4H, d, J=8.9 Hz) 3.68 (6H, s),.; $^{13}$C NMR: δ 152.6, 138.3, 137.3, 118.2, 117.8, 114.5, 55.2.

Compound QR-0306 was prepared by the reaction depicted in the following Scheme:

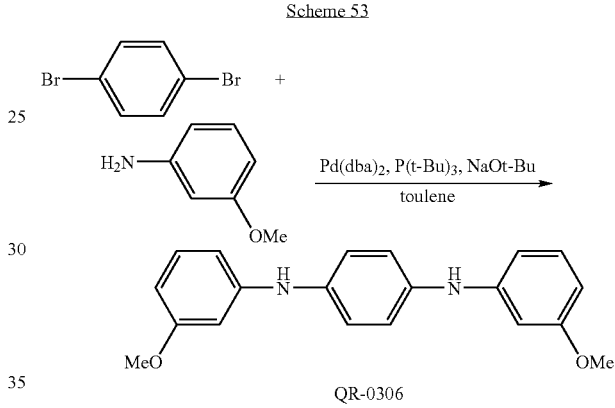

The same procedure as described above with regard to QR-0292 was used to yield QR-0306 (Yield: 12%). $^1$H NMR (DMSO-d$_6$): δ 7.89 (2H, s), 7.07 (2H, t, J=8.2 Hz), 7.04 (4H, s), 6.56 (2H, m), 6.50 (2H, m), 6.32(2H, m), 3.69 (6H, s); $^{13}$C NMR (DMSO-d$_6$): δ 160.2, 146.2, 136.4, 129.8, 120.0, 107.7, 103.8, 100.7, 54.7.

EXAMPLE 47

Preparation of QR-0293, QR-0294, QR-0304

QR-0293, QR-0294 and QR-0304 were prepared by the reaction depicted in the following Scheme:

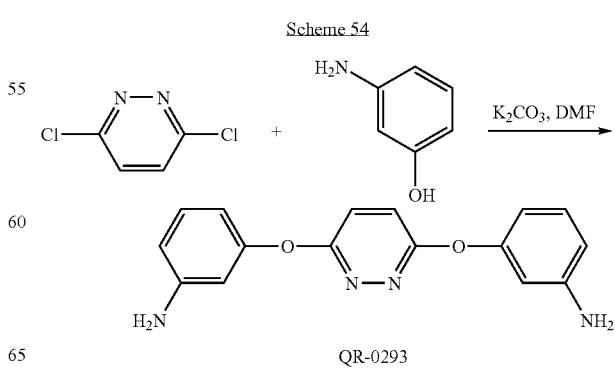

The following procedure was used. A solution of 3,6-dichloropyridazine (0.298 g, 2.00 mmol), m-aminophenol (0.480 g, 4.40 mmol), potassium carbonate (0.414 g, 3.00 mmol) in DMF (10 mL) was refluxed for 12 h. Upon completion, the mixture was cooled to room temperature, distilled water (50 mL) was added, and the mixture was extracted with ethyl acetate (3×40 mL). The combined organic extracts were washed with brine before being dried over MgSO$_4$. The solution was concentrated under reduced pressure, and the residue washed with Et$_2$O (20 mL×3) and hexane (20 mL×2), yielding the following compounds.

QR-0293 (0.419 mg, 71%) as a colourless solid. $^1$H NMR (DMSO-d$_6$): δ 7.42 (2H, s), 7.04 (2H, t, J=8.1 Hz), 6.43 (2H, m), 6.34 (2H, t, J=2.2 Hz), 6.26 (2H, m), 5.26 (4H, s); $^{13}$C NMR(DMSO-d$_6$): δ 163.1, 155.1, 150.4, 129.9, 122.3, 110.5, 107.0, 105.4.

QR-0294

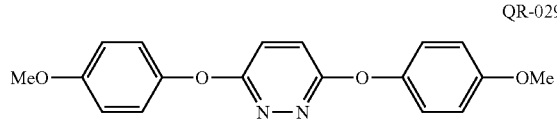

Yield 39%; $^1$H NMR (DMSO-d$_6$): δ 7.48 (2H, s), 7.11 (4H, d, J=9.0 Hz), 6.96 (4H, d, J=9.0 Hz), 3.75 (6H, s); $^{13}$C NMR (DMSO-d$_6$): δ 163.2, 156.3, 147.0, 122.1, 122.0, 114.7, 55.4.

QR-0304

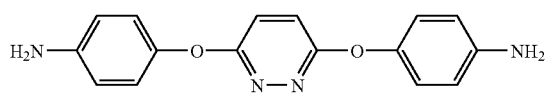

Yield: 84%; $^1$H NMR (DMSO-d$_6$): δ 7.32 (2H, s), 6.84 (4H, m), 6.59 (4H, m), 5.00 (4H, s); $^{13}$C NMR (DMSO-d$_6$): δ163.4, 146.0, 143.8, 121.48, 121.46, 114.4.

EXAMPLE 48

Preparation of QR-0315, QR-0316, QR-0317

Compounds QR-0315, QR-0316, and QR-0317 were prepared by the reaction depicted in the following Scheme:

Scheme 55

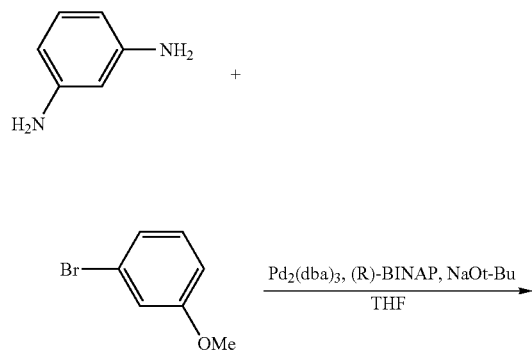

-continued

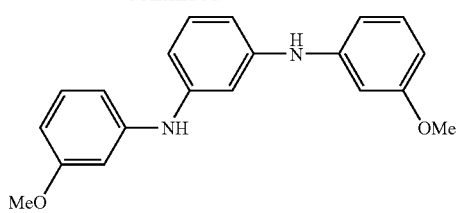

The following procedure was used. A mixture of 1.3-benzediamine (0.216 g, 2.00 mmol), 3-bromoanisole (0.767 g, 4.1 mmol), tris(dibenzylideneacetone)dipalladium (Pd$_2$(dba)$_3$) (36.6 mg, 0.04 mmol), (R)-BINAP (62.3 mg, 0.10 mmol), and sodium tert-butoxide (0.499 g, 5.20 mmol) in THF (10 ml) was refluxed for 12 h, a second portion of (Pd$_2$(dba)$_3$ (18.0 mg) was added and the mixture refluxed for another 12 h. Upon completion, the reaction mixture was concentrated and ethyl acetate (30 mL) and brine (20 mL) were added. The layers were separated and the aqueous layer extracted further with ethyl acetate (3×20 mL). The combined organic layers were washed with brine (20 mL), dried over MgSO$_4$. and concentrated under vacuum. Flash column chromatography (20% EtOAc/hexane) of the residue yielded the following compounds.

QR-0315 (0.486, 76%) as a colorless liquid. $^1$H NMR (CDCl$_3$): δ 7.13 (3H, m), 6.75 (1H, m) 6.62 (6H, m), 6.46 (2H, m), 5.67 (2H, m), 3.74(6H, s); $^{13}$C NMR(CDCl$_3$): δ 160.9, 144.5, 144.3, 130.3, 130.2, 111.1, 110.8, 107.5, 106.5, 104.0, 55.4.

QR-0316

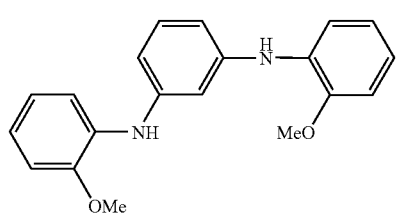

Yield: 96%; $^1$H NMR (CDCl$_3$): δ 7.31 (2H, d, J=7.0 Hz), 7.12 (1H, t, J=8.0 Hz), 6.84 (7H, m), 6.68 (2H, m), 6.09 (2H, m), 3.79 (6H, s); $^{13}$C NMR (CDCl$_3$): δ 148.5, 144.0, 133.0, 130.1, 120.9, 120.1, 115.4, 111.4, 110.7, 108.1, 55.6.

QR-0318

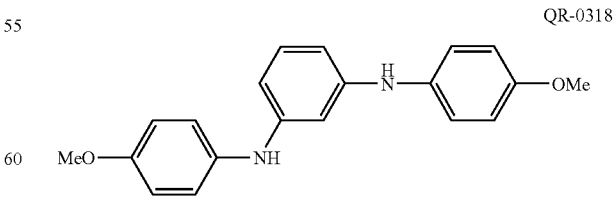

Yield: 63%; $^1$H NMR (CDCl$_3$): δ 7.04 (511, m), 6.84 (4H, m), 6.43 (1H, m), 6.37 (2H, m), 5.41 (2H, s), 3.78 (6H, s); $^{13}$C NMR (CDCl$_3$): δ 155.5, 146.6, 135.9, 130.3, 122.7, 114.8, 107.4, 102.8, 55.8.

EXAMPLE 49

Preparation of QR-0319, QR-0325, QR-0326

Compounds QR-0319, QR-0325, and QR-0326 were prepared by the reaction depicted in the following Scheme:

Scheme 56

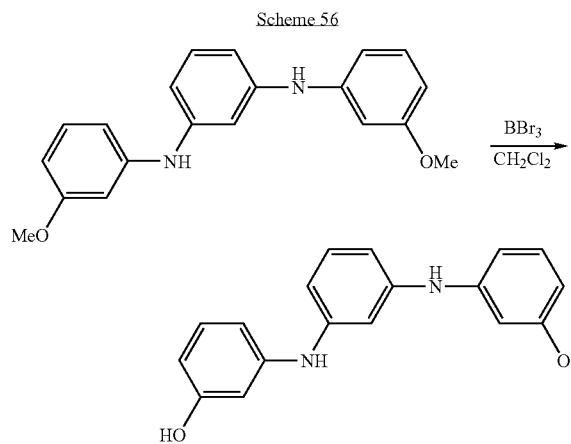

The following procedure was used. To a suspension of compound QR-315 (0.215 g, 0.672 mmol) in dry $CH_2Cl_2$ (50 mL) cooled to −78° C. was added $BBr_3$ (0.38 mL, 4.03 mmol) dropwise. The reaction mixture was left to warm to room temperature overnight. The mixture was washed with saturated aqueous $NaHCO_3$ (20 mL) the aqueous layer was extracted further with $CH_2Cl_2$ (3×30 mL), and the combined $CH_2Cl_2$ extracts were washed with brine (30 mL). The organic layer was dried over $MgSO_4$ and concentrated under vacuum. Flash column chromatography (20% EtOAc/hexane) of the residue gave the following comounds.

Dihydroxyl compound QR-0319 (0.188 g, 96%) was obtained as a colorless solid. $^1H$ NMR ($CDCl_3$): 7.04 (2H, m), 7.02 (2H, m), 6.95 (1H, t, J=7.9 Hz), 6.93 (2H, m), 6.86 (2H, m), 6.24 (2H, dd, J=8.0, 2.2 Hz), 6.12 (1H, t, 2.2 Hz), 5.75 (2H, bs); $^{13}C$ NMR ($CDCl_3$): 151.2, 146.9, 130.6, 129.0, 126.4, 125.3, 121.2, 115.6, 107.9, 103.1.

QR-0325

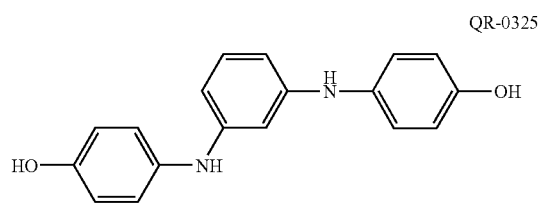 [SMILES: Oc1ccc(Nc2cccc(Nc3ccc(O)cc3)c2)cc1]

Yield: 78%; $^1H$ NMR($CD_3OD$): 6.94 (6H, m), 6.69 (5H, m), 6.50 (1H, m), 6.30 (2H, m); $^{13}C$ NMR ($CD_3OD$): 153.3, 148.4, 137.1, 130.6, 123.2, 116.7, 107.6, 103.3.

QR-0326

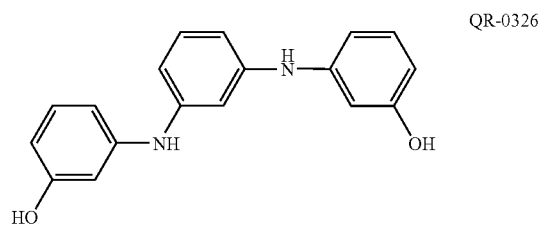 [SMILES: Oc1cccc(Nc2cccc(Nc3cccc(O)c3)c2)c1]

Yield: 75%; $^1H$ NMR ($CD_3OD$): 7.03 (511, m), 6.86 (1H, m) 6.57 (6H, m), 6.30 (2H, m); $^{13}C$ NMR ($CD_3OD$): 159.05, 146.53, 145.76, 145.69, 130.8, 130.7. 130.4, 110.2, 108.2, 105.2.

EXAMPLE 50

Activity Against Aβ Agregation

The compounds of the invention were evaluated for activity against Aβ aggregation in a kinetic thioflavin T (ThT) fluorescence assay similar to that of Chalifour, R. J., et al., *J. Biol. Chem.* (2003) 278: 34874-81.

The following procedures were used. The compounds were examined by circular dichroism (CD) to confirm their anti-amyloidogenic activity and were further evaluated for inhibition of both tau and α-synuclein aggregation in Thioflavin S (ThS) and ThT dye-binding fluorescence assays, respectively. The compounds were also evaluated in a MTT [3-(4, 5-dimethylthiazol-2-yl)-2,5-diphenyltetrazolium bromide] cell viability assay (Kaneko, I., et al., *J. Neurochem.* (1995) 65: 2585-93). Pharmacokinetic (PK) testing was also performed. Compounds administered to mice (IP or PO dosing) had no toxicity at doses up to 300 mg/kg and were present in brain more than four hours after administration.

Many of the in-vitro tests discussed above were performed in accordance with the methods disclosed in U.S. patent application Ser. No. 11/443,396, U.S. Publication No. 2007-0015813, filed May 30, 2006, herein incorporated by reference.

The structure, in vitro activities and PK data for certain compounds are summarized below.

(I) QR-0109

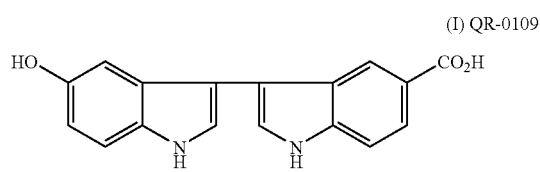

- Inhibits Aβ40 and Aβ42 aggregation (ThT)
- Inhibits tau aggregation (ThS)
- Inhibits α-synuclein aggregation (ThT)
- Non-toxic up to 300 mg/kg, crosses blood-brain barrier, has $t_{1/2}$ of several hours in mouse PK studies (II) QR-0112

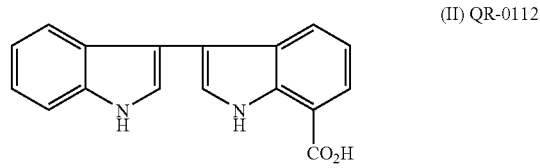

- Inhibits Aβ40 aggregation (ThT and CD)
- Binds Aβ28 in MS experiments
- Protects SH-SY5Y cells from Aβ40 toxicity (MTT)

(III) QR-0161

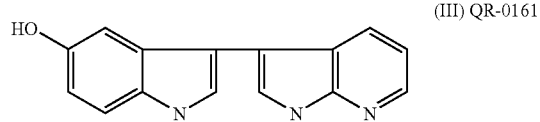

- Inhibits Aβ aggregation (ThT)
- Inhibits tau aggregation (ThS)
- Protects SH-SY5Y cells from Aβ40 toxicity (MTT)
- Non-toxic in mice up to 300 mg/kg (IV) QR-0194

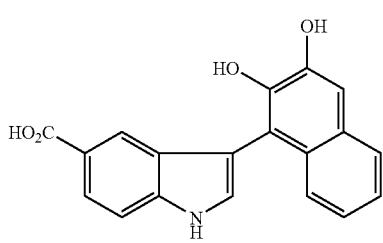 [SMILES: O=C(O)c1ccc2[nH]cc(-c3c(O)c(O)cc4ccccc34)c2c1]

- Inhibits Aβ aggregation (ThT)
- Inhibits α-synuclein aggregation (ThT)
- Protects SH-SY5Y cells from Aβ40 toxicity (MTT)

The compounds were found to inhibit aggregation of both Aβ40 and Aβ42, as well as reverse the aggregation of both species when added to pre-formed aggregates.

EXAMPLE 50A

Cell Viability Assay

The cell viability assay was performed for QR-0112 and QR-0161 of Example 50.

The assay was based on that reported by Conte and co-workers (Conte, A., Pellegrini, s. & Tagliazucchi, D. 2Q03. *Brain Res. Bull.* 62, 29-38). Briefly, Aβ1-40 (1.0 mg) was dissolved directly in Tris base (15 mL, 20 microM, pH approximately 10). The pH was dropped to 7.4 using concentrated HCl and the solution diluted ten-fold with growth medium consisting of Dulbecco's Modified Eagle Medium (high glucose) containing 10% fetal bovine serum. penicillin-G (10,000 units/mL) and streptomycin (10 mg/mL); giving 20 μM Aβ40. For non-Aβ-containing controls. growth medium was diluted 10% with Tris buffer (20 mM, pH 7.4). SH-SY5Y neuroblastoma cells were seeded at approximately 20,000 cells per well in a covered 96-well clear polystyrene plate and incubated at 37° C., 5% $CO_2$ for 24 h. After discarding supernatant, growth medium (200 μL), containing either Aβ3-40 or vehicle (controls), was added to the wells, followed by test compound in DMSO (0.5 μL) or DMSO alone (controls). Incubations all had 5 or more replicates. After incubating for 6-10 h (37° C., 5% $CO_2$), the dye 3-(4,5-dimethylthiazol-2-yl)-2,5-diphenyltetrazolium bromide (MTT, 20 microL. 5 mg/mL in PBS) was added to each well and the plate incubated for another 2 h. Medium was discarded and the formazan product dissolved by adding DMSO (100 μL) and shaking. Absorbance was measured at 540 nm in a Tecan Genios microplate reader. Absorbance values for wells containing neither Aβ40 nor test compound at the beginning of the experiment were taken as 100%, while wells to which was added 20% Triton X-100 (0.5 μL) to lyse the cells were taken as a complete inhibition of cell function (0%).

Figure 2:
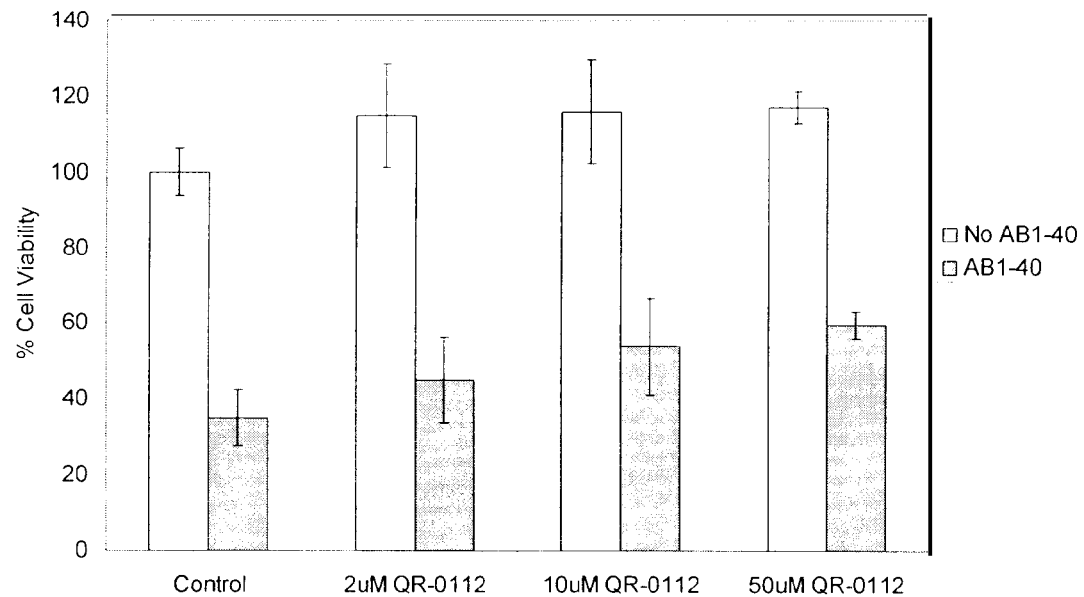
FIGS. 2 and 3 are % cell viability graphs for the cell viability assay performed on QR-0112 in EXAMPLE 50A.
Figure 3:
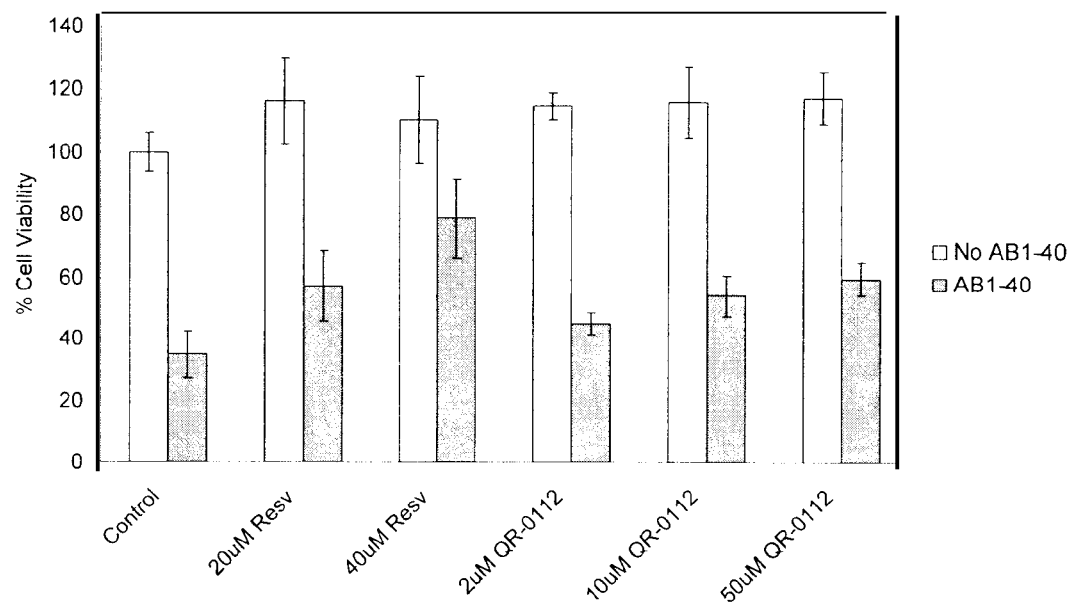
Figure 4:
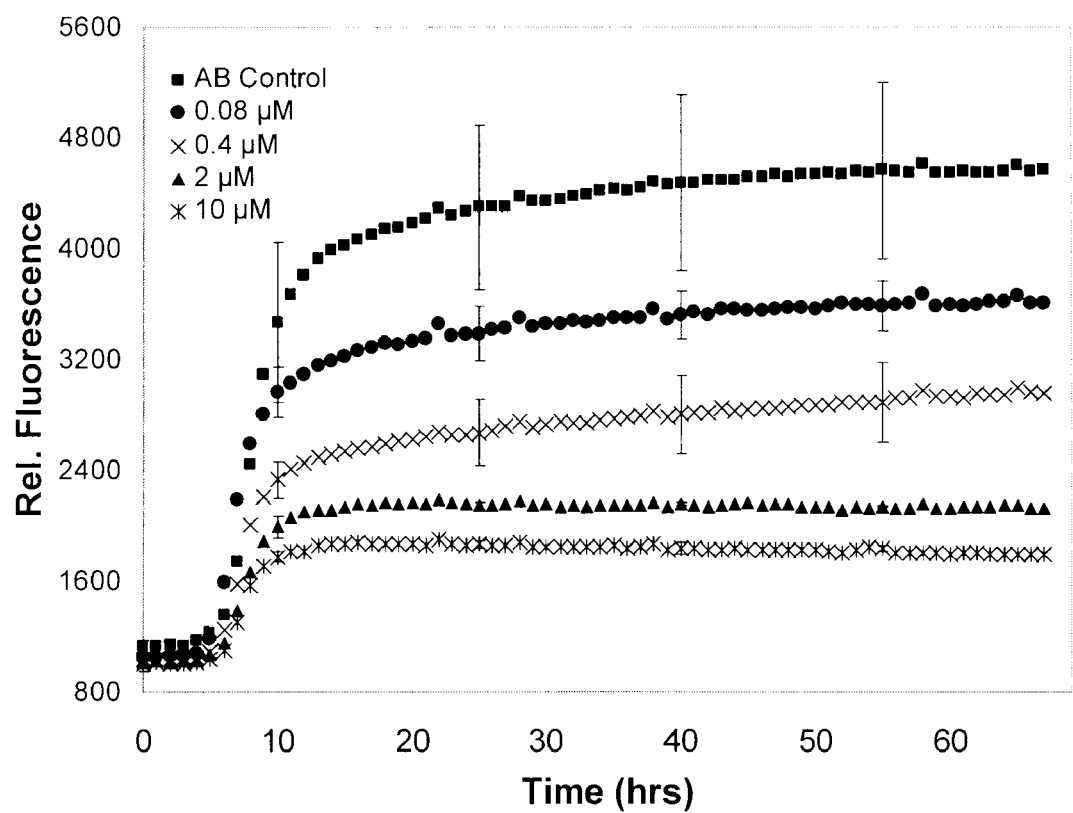
FIG. 4 is a graph (Rel. Fluorescene v. Time) for QR-0292 for assays of EXAMPLE 52.

The results of the assay are graphically depicted in FIG. 1, FIG. 2 and FIG. 3.

It was concluded that QR-0112 ($p<0.05$) is significantly protective at 50 μM and trends towards protection at the lower concentrations of 2 and 10 μM; and that QR-0161 is significantly active at both 20 and 50 μM and protects SH-SY5Y cells from Aβ40 (20 μM).

EXAMPLE 51

Inhibition of Aβ1-40 Aggregation in the ThT Fluorescence Assay $IC_{50}$ values for inhibition of Aβ1-40 aggregation in the ThT fluorescence assay for a number compounds of the present invention were determined. Values were calculated by solving the equation $y=(m_2)/(1+(x/m_3)^{m_4})$ where y is percent aggregation, x is compound concentration, and $m_3$ is the concentration giving 50% aggregation (i.e. $IC_{50}$), using KaleidaGraph 4.0 (Synergy Software). The data obtained is summarized in Table 1 below.

TABLE 1

| | Compound | Structure | IC$_{50}$ (μM) | Error (μM) |
|---|---|---|---|---|
| 1 | QR-0109 | (structure) | 6.5 | 0.8 |
| 2 | QR-0112 | (structure) | 34.4 | 9.6 |
| 3 | QR-0142 | (structure) | 150.7 | 15.1 |

TABLE 1-continued

| Compound | Structure | IC$_{50}$ (µM) | Error (µM) |
|---|---|---|---|
| 4 QR-0162 | | 17.5 | 0.7 |
| 5 QR-0164 | | 3.0 | 1.7 |
| 6 QR-0171 | | 5.8 | 0.2 |
| 7 QR-0176 | | 1.99 | 1.13 |
| 8 QR-0185 | | 12.5 | 3.2 |
| 9 QR-0189 | | 19.0 | 1.5 |
| 10 QR-0194 | | 17.7 | 3.8 |

TABLE 1-continued

| | Compound | Structure | IC$_{50}$ (µM) | Error (µM) |
|---|---|---|---|---|
| 11 | QR-0212 | 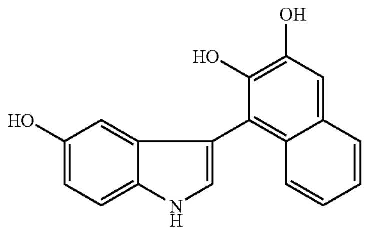 [SMILES: Oc1ccc2[nH]cc(-c3c(O)c(O)cc4ccccc34)c2c1] | 8.2 | 1.1 |
| 12 | QR-0216 | 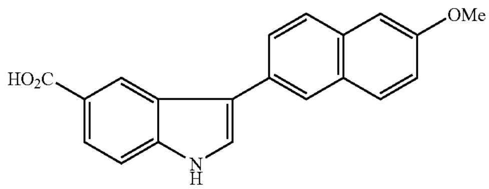 [SMILES: COc1ccc2cc(-c3c[nH]c4ccc(C(=O)O)cc34)ccc2c1] | 35.5 | 21.1 |
| 13 | QR-0217 | 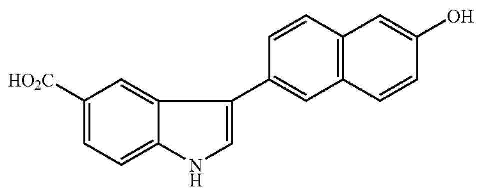 [SMILES: O=C(O)c1ccc2[nH]cc(-c3ccc4cc(O)ccc4c3)c2c1] | 7.5 | 1.2 |
| 14 | QR-0225 | 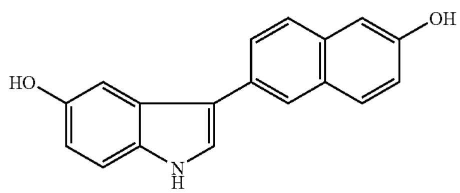 | 7.0 | 0.8 |
| 15 | QR-0229 | 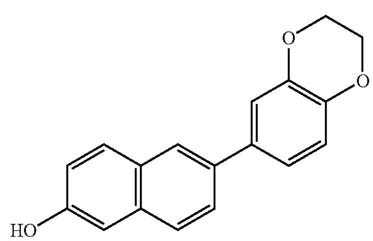 [SMILES: Oc1ccc2cc(-c3ccc4c(c3)OCCO4)ccc2c1] | 18.9 | 2.3 |
| 16 | QR-0231 | 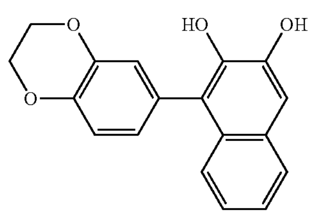 [SMILES: Oc1cc2ccccc2c(-c2ccc3c(c2)OCCO3)c1O] | 27.8 | 5.1 |
| 17 | QR-0238 | 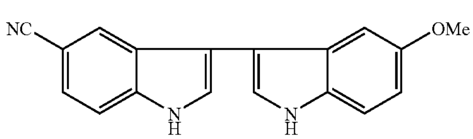 | 20.9 | 8.1 |
| 18 | QR-0240 | 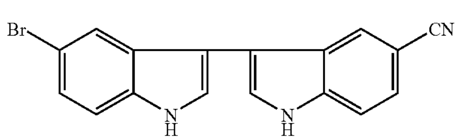 [SMILES: N#Cc1ccc2[nH]cc(-c3c[nH]c4ccc(Br)cc34)c2c1] | 12.0 | 0.1 |

TABLE 1-continued

| Compound | Structure | IC$_{50}$ (μM) | Error (μM) |
|---|---|---|---|
| 19 QR-0244 | | 5.6 | 0.1 |
| 20 QR-0253 | | 11.8 | 4.6 |
| 21 QR-0256 | | 17.1 | 3.4 |
| 22 QR-0258 | | 10.0 | 3.4 |
| 23 QR-0261 | | 10.3 | 3.2 |
| 24 QR-0262 | | 4.4 | 0.1 |
| 25 QR-0263 | | 1.93 | 0.07 |
| 26 QR-0269 | | >200 μM | — |

TABLE 1-continued

| Compound | | Structure | IC$_{50}$ (μM) | Error (μM) |
|---|---|---|---|---|
| 27 | QR-0273 | 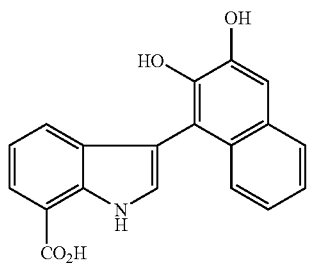 [SMILES: O=C(O)c1cccc2c(-c3c(O)c(O)cc4ccccc34)c[nH]c12] | 10.3 | 2.0 |
| 28 | QR-0276 | 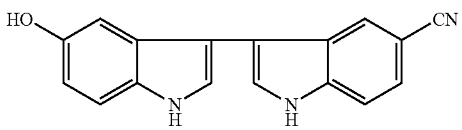 [SMILES: N#Cc1ccc2[nH]cc(-c3c[nH]c4ccc(O)cc34)c2c1] | 16.5 | 6.9 |
| 29 | QR-0284 | 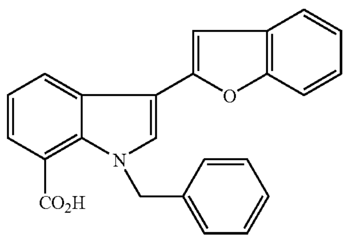 [SMILES: O=C(O)c1cccc2c(-c3cc4ccccc4o3)cn(Cc3ccccc3)c12] | >50 μM | — |
| 30 | QR-0281 | 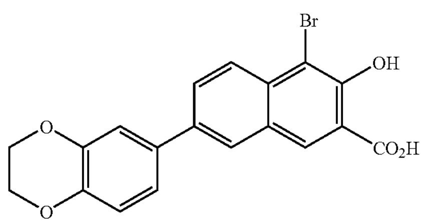 [SMILES: O=C(O)c1cc2cc(-c3ccc4c(c3)OCCO4)ccc2c(Br)c1O] | 4.6 | 0.8 |
| 31 | QR-0287 | 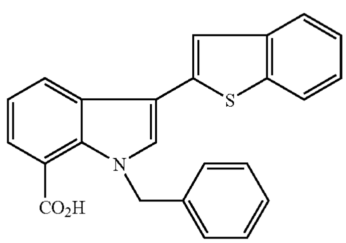 [SMILES: O=C(O)c1cccc2c(-c3cc4ccccc4s3)cn(Cc3ccccc3)c12] | 19.5 | 21.9 |
| 32 | QR-0292 | 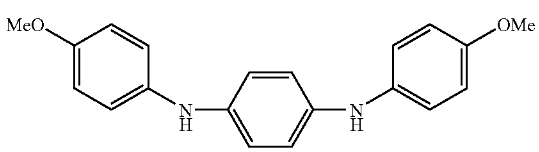 [SMILES: COc1ccc(Nc2ccc(Nc3ccc(OC)cc3)cc2)cc1] | 0.54 | 0.01 |
| 33 | QR-0297 | 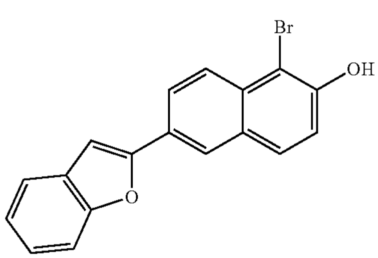 [SMILES: Oc1ccc2cc(-c3cc4ccccc4o3)ccc2c1Br] | 0.57 | 0.95 |

TABLE 1-continued

| | Compound | Structure | IC$_{50}$ (μM) | Error (μM) |
|---|---|---|---|---|
| 34 | QR-0300 | 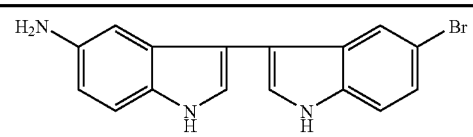 | 1.7 | 0.6 |
| 35 | QR-0313 | 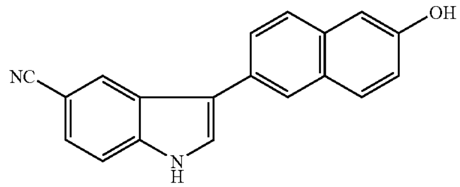 | 6.5 | 5.4 |
| 36 | QR-0302 | 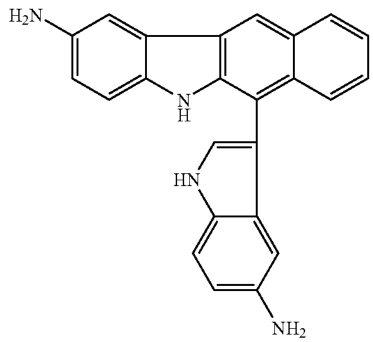 [SMILES: Nc1ccc2[nH]cc(-c3c4ccccc4cc4c3[nH]c3ccc(N)cc34)c2c1] | 3.2 | 0.4 |
| 37 | QR-0303 | 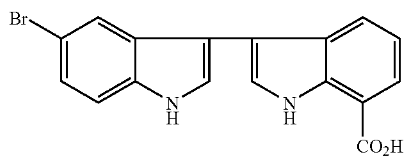 [SMILES: O=C(O)c1cccc2c(-c3c[nH]c4ccc(Br)cc34)c[nH]c12] | 21.0 | 3.9 |
| 38 | QR-0315 | 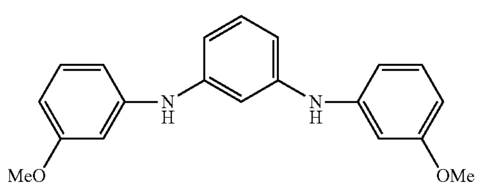 | 5.7 | N.D. |
| 39 | QR-0316 | 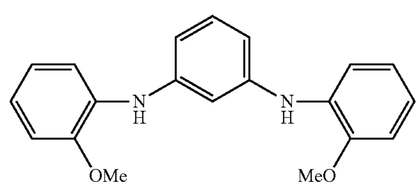 | >50 | — |
| 40 | QR-0317 | 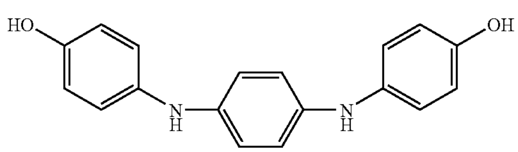 [SMILES: Oc1ccc(Nc2ccc(Nc3ccc(O)cc3)cc2)cc1] | 2.3 | 0.07 |
| 41 | QR-0319 | 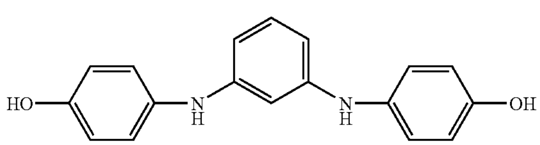 [SMILES: Oc1ccc(Nc2cccc(Nc3ccc(O)cc3)c2)cc1] | 2.4 | 0.2 |

TABLE 1-continued

| Compound | | Structure | IC$_{50}$ (μM) | Error (μM) |
|---|---|---|---|---|
| 42 | QR-0321 | [structure: 5-cyanoindole linked to dihydroxynaphthalene] | 9.4 | 6.1 |
| 43 | QR-0325 | [structure: 1,3-bis(4-hydroxyphenylamino)benzene] | 1.03 | 0.09 |
| 44 | QR-0326 | [structure: 1,3-bis(3-hydroxyphenylamino)benzene] | 3.3 | 1.3 |
| 45 | QR-0327 | [structure: 5-nitroindole linked to indole-7-carboxylic acid] | 11.5 | 5.3 |

EXAMPLE 52

Thioflavin T (ThT) and Thioflavin S (ThS) Aggregation Assays for Aβ, Tau and α-Synuclein 1) Thioflavin T (ThT) and Thioflavin S (ThS) Aggregation Assays for Aβ, Tau and α-Synuclein Dye-binding ThT/ThS protein aggregation assays for Aβ, tau and α-synuclein were performed as described in Example 8 of US2007/0015813.

2) Tris-Tricine SDS-PAGE:

Pre-cast polyacrylamide gels were purchased from NuSep (10-20% Tris-tricine-SDS). These were chosen for their large separation range of 2.5 to 205 kDa. Molecular weight markers were purchased from Sigma Aldrich and diluted twenty fold for individual use. Three buffers were used for this technique: 1) Sample buffer (1.25 mL 0.5 M Tris-HCl (pH 6.8), 2.5 mL glycerol, 2.0 mL 10% SDS, 0.2 mL 0.5% bromophenol blue, 3.55 mL distilled water) which was used as the leading band in the gel. 2) Cathode Buffer (12.11 g tris base, 17.92 g tricine, 1 g SDS, diluted to 1 L with distilled water) which was the inner buffer in the tank assembly. 3) Anode Buffer (5× concentrated: 121.1 g tris base in 1 L of distilled water, pH 8.9 adjusted with concentrated HCl) which was the outer buffer and loaded at 1× concentration. Both Aβ1-40 and Aβ1-42 were purchased from Anaspec.

Five solutions were required to stain the gels using the silver stain protocol: 1) Fixer 1 (40% methanol, 10% acetic acid, diluted to 1 L with Millie-Q water) 2) Fixer 2 (45 g anhydrous sodium acetate, 300 mL methanol, 5 mL 25% glutaraldehyde, diluted to 1 L with Millie-Q water), 3) a) Silver stain A (15 mL of 25% ammonia solution, 0.8 g sodium hydroxide, diluted to 950 mL with Millie Q water). b) Silver stain B (6 g of silver nitrate in 50 mL Millie Q water). Solution B was then slowly added to solution A. 4) Developer (0.1 g citric acid, 1 mL formaldehyde, diluted to 1 L with Millie-Q water), 5) Stop solution (50 mL acetic acid, diluted to 1 L with Millie-Q water).

Sample preparation: Aβ1-40 and Tau 441

Following a ThT (Aβ1-40) or ThS (Tau 441) aggregation assay, described in Example 8 of US2007/0015813, samples were immediately aspirated and stored in centrifuge tubes. 10 μL of each sample was transferred to a microfuge tube and diluted 1:1 with sample buffer before being incubated (37° C.) for 30 minutes and loaded in the precast gels (15 μL in each well). The gel was then run at 100 V for approximately one hour or until the leading band reached the bottom of the gel.

Sample Preparation: Aβ1-42 Treatment

Aβ1-42 was dissolved in 1.15 mL tris base (pH~10), vortexed and sonicated, giving a concentration of 200 μM. The pH was then dropped to 7.4 using concentrated HCl and the solution diluted 10-fold with PBS and transferred as 20 μL aliquots to microfuge tubes. Compounds were added as 0.2 μL additions of DMSO stock solutions. Samples were then diluted 1:1 with sample buffer and incubated (37° C.) for 30 minutes before being loaded into precast gels. The load volume was 15 μL and the gel was run at 100 volts for approximately one hour or until the leading band reached the bottom of the gel.

Silver Staining

Once the gel had finished running, it was removed from its plastic case and placed in a tray for staining. Approximately 200-250 mL volume was used for all the solutions. The gel was first washed with distilled water briefly to rinse off the excess buffer from the tank. It was then immersed in Fixer 1 for 30 minutes. followed by Fixer 2 for 30 minutes. Once the gel was fixed it then underwent three water washes at 10 minutes per wash. After the water washes, the gel was stained for 30 minutes using the silver stain solution. Excess stain was removed using three four-minute water washes. The gel was then immersed in the developer solution to visualize the stain. This took place for approximately 5 minutes or until the desired intensity was reached. To immediately stop the developing process the gel was placed in the stop solution for 10 minutes.

3) Transmission Electron Microscopy (TEM)

A modified version of the procedure of Cohen et al. (*Biochemistry* 2006, 45: 4727-35) was followed for TEM analysis. Uranylacetate was used as negative stain (Electron Microscopy Sciences) and was made as a 3% solution and stored at 5° C. in the dark to reduce photodecay. Aspirated samples from ThT (Aβ1-40) and ThS (Tau 441) aggregation assays, or Aβ1-42 incubated (37° C.) for 30 min. in the presence and absence of compounds were used in the TEM analyses. Samples were carefully loaded on Formvar-coated 400 mesh copper grids (Electron Microscopy Sciences) as a 10 µL drop. After sitting for 60 seconds, excess fluid was gently dabbed off with filter paper. Next, the 3% uranylacetate was added as a drop onto the grid and left to stand for another 60 seconds. The excess fluid was again dabbed off by filter paper. Samples were left to dry for at least 30 minutes prior to being viewed on an electron microscope operating at 80 kV.

4) Results

Effects of QR-0292 (0.08-10 microM) on ABeta1-40 aggregation in the ThT fluorescence assay.

Figure 5:
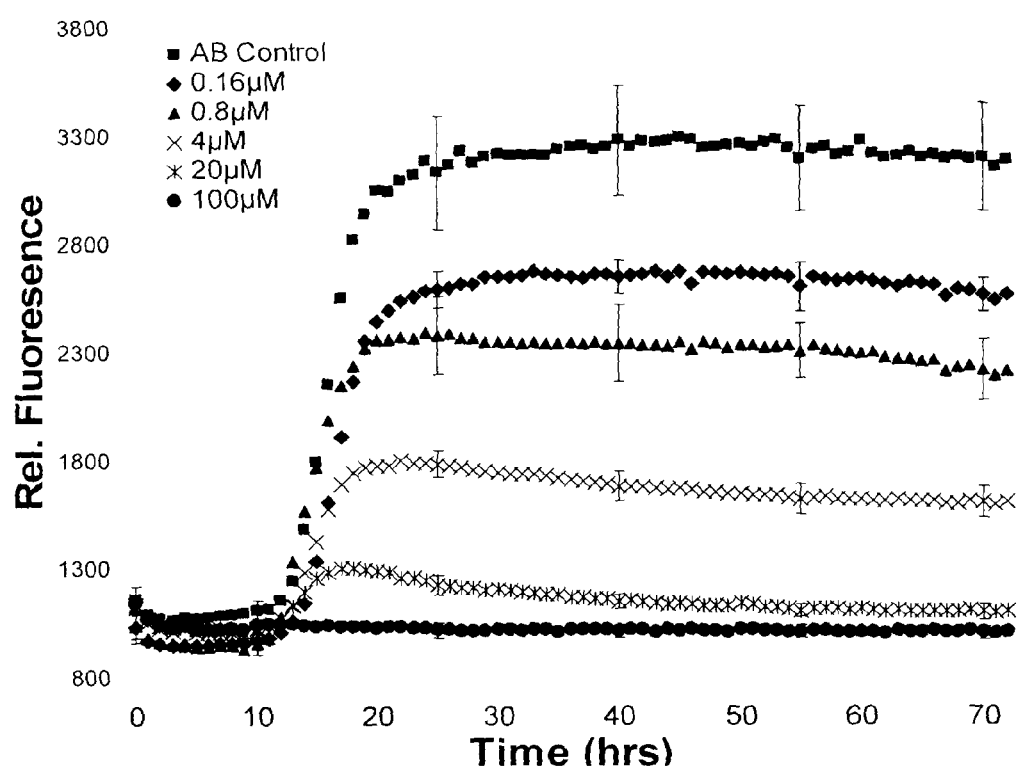
FIG. 5 is a graph (Rel. Fluorescene v. Time) for QR-0319 for assays of EXAMPLE 52.

Effects of QR-0319 (0.16-100 µM) on Aβ1-40 aggregation in the ThT fluorescence assay is graphically depicted in FIG. 5.

Figure 6:
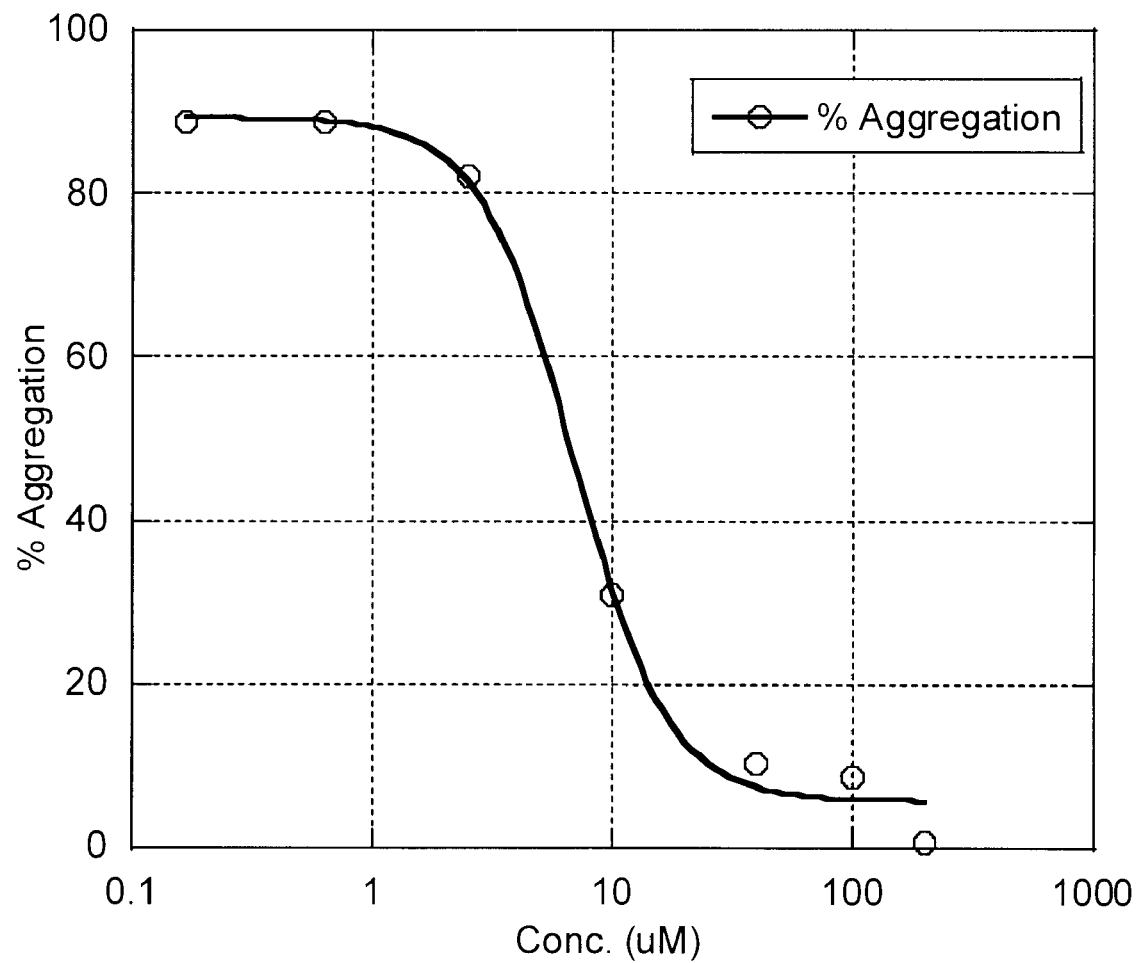
FIG. 6 is a graph (% aggregation v. conc.) for QR-0217 for assays of EXAMPLE 52.

$IC_{50}$ curve for QR-0217 against aggregation of Aβ1-40 in the ThT assay is graphically depicted in FIG. 6. The $IC_{50}$ value for QR-0217 is 7.5 µM. See Table 1.

Figure 7:
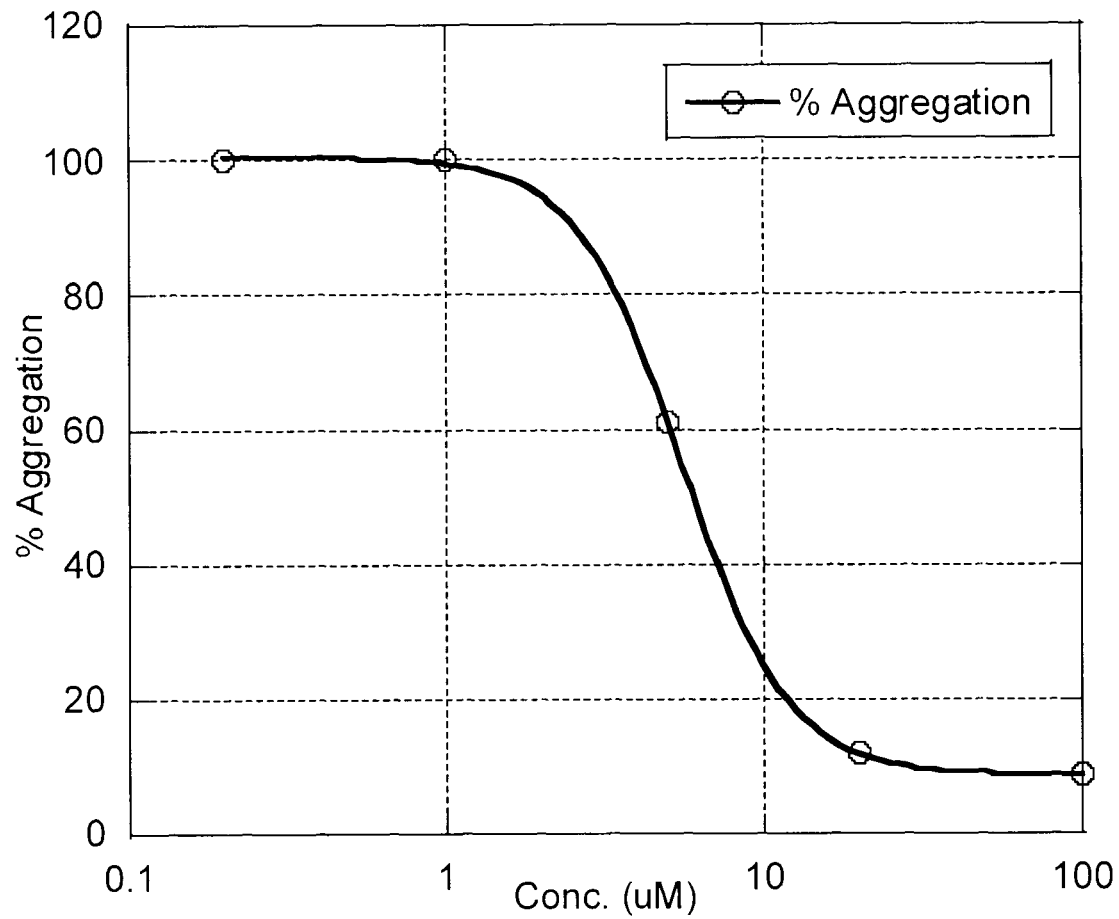
FIG. 7 is a graph (% aggregation v. conc.) for QR-0244 for assays of EXAMPLE 52.

$IC_{50}$ curve for QR-0244 against aggregation of Aβ1-40 in the ThT assay is graphically depicted in FIG. 7. The $IC_{50}$ value for QR-0244 is 5.6 µM. See Table 1.

Figure 8:
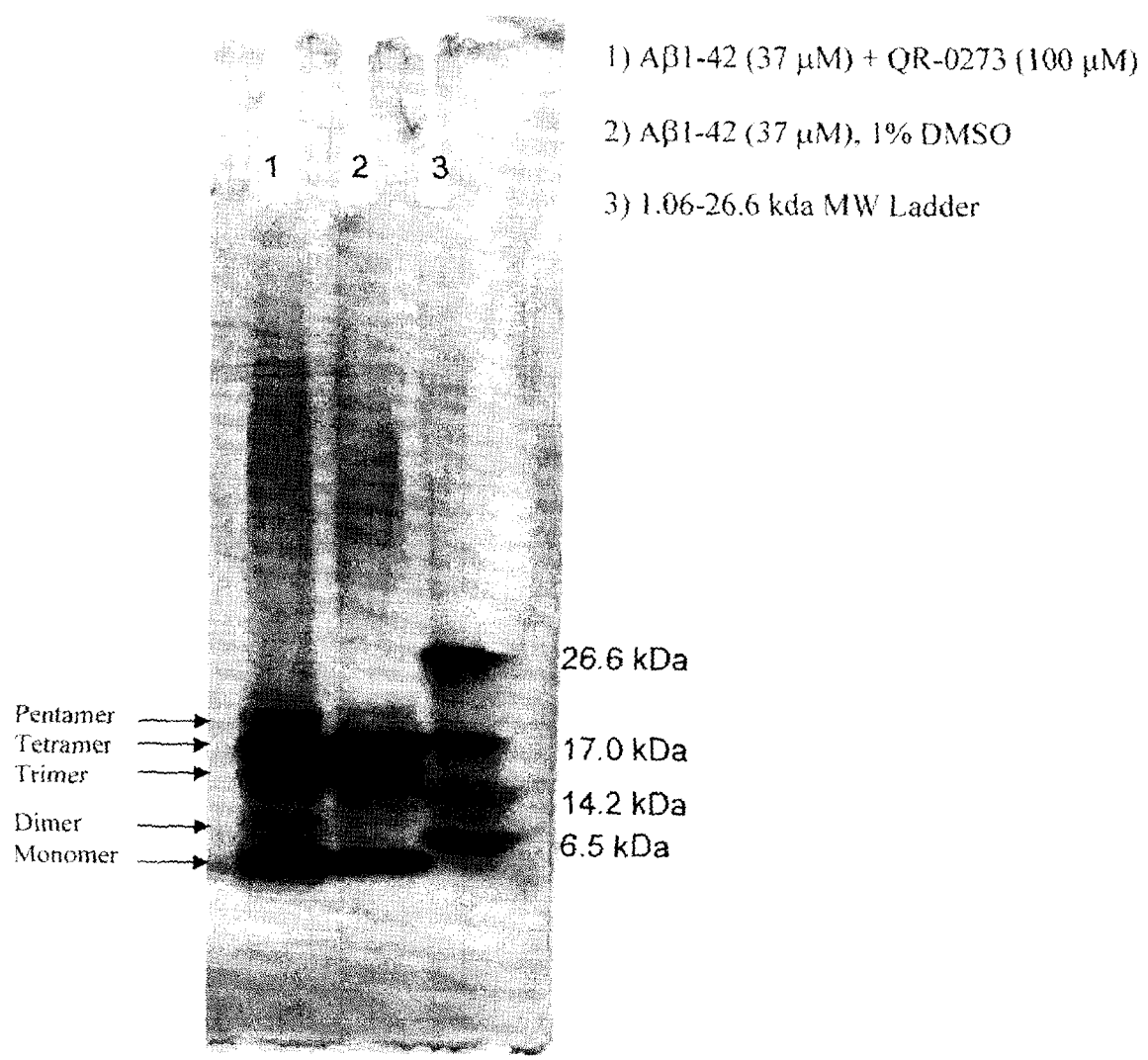
FIG. 8 is a SDS PAGE technique showing the effect of QR-0273 on Aβ1-42 self-assembly.

SDS-PAGE technique showing the effect of QR-0273 on Aβ1-42 self-assembly is shown in FIG. 8. The compound caused an increase in the presence of monomer and pentamer as well as the appearance of a dimer and possibly a darker higher molecular weight smear (lane 1) versus control (lane 2). Lane 3 is a molecular weight marker.

Figure 9:
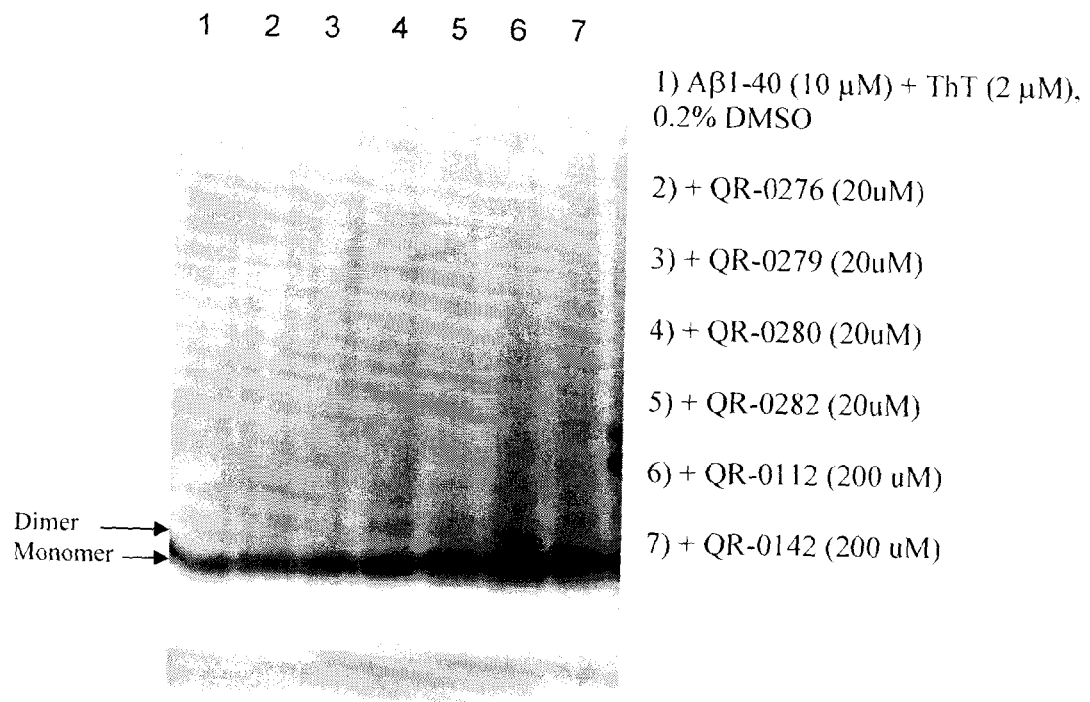
FIG. 9 is a SDS PAGE technique showing the effects of compounds on Aβ1-40 self-assembly following ThT aggregation assay of EXAMPLE 52.

SDS-PAGE technique showing the effect of compounds on Aβ1-40 self-assembly following ThT aggregation assay is depicted in FIG. 9. QR-0276 and QR-0279 (lanes 2 and 3) appeared to have little effect on the distribution of Aβ1-40 among the various states of assembly when compared to control (lane 1). QR-0280, QR-0282, QR-0112, and QR-0142 (lanes 4-7), however, caused an increase in the concentration of Aβ1-40 monomer. QR-0280 and QR-0282 also caused the appearance of a dimer band, further demonstrating their ability to modulate Aβ1-40 aggregation.

Figure 10:
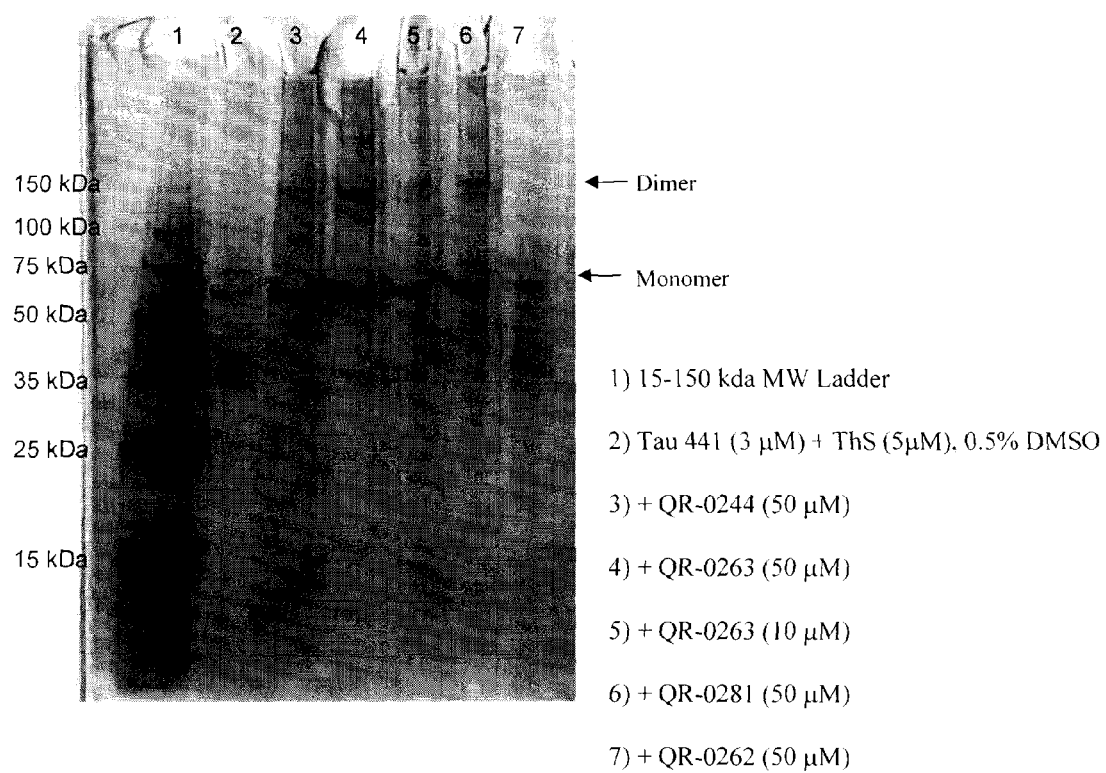
FIG. 10 a SDS PAGE technique showing the effects of compounds on Tau 441 self-assembly following ThS aggregation assay of EXAMPLE 52.

SDS-PAGE technique showing the effect of compounds on Tau 441 self-assembly following ThS aggregation assay is depicted in FIG. 10. Incubations containing QR-0244, QR-0263, and QR-0281 (lanes 3-6) had decreased fragmentation of tau 441 monomer relative to control (lane 2) as well as the appearance of dimer and trimer bands. Conversely, QR-0262 (lane 7) had no clear effect on Tau 441 self-assembly in this assay. Lane 1 is a molecular weight marker. The ability of compounds to inhibit Tau441 fragmentation is of particular interest given the implication of fragmentation in the protein's subsequent aggregation and neurotoxicity (Y P Wang et al., *Proc Nat'l Acad Sci USA* 2007, 104:10252-7).

Figure 11:
FIG. 11 is a TEM micrograph of Aβ1-40 (20 μM) incubated in the absence (a) and presence of compounds (b,c), taken following the ThT aggregation assay of EXAMPLE 52.
Figure 11:
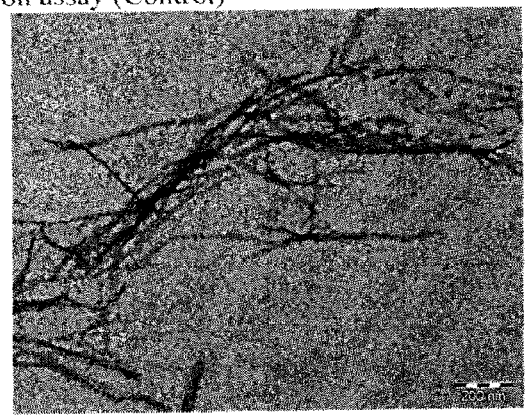
Figure 11:
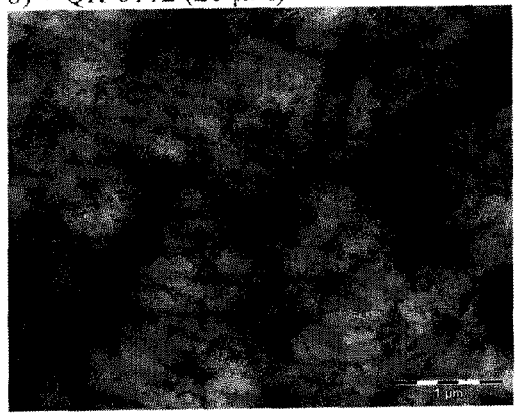
Figure 11:
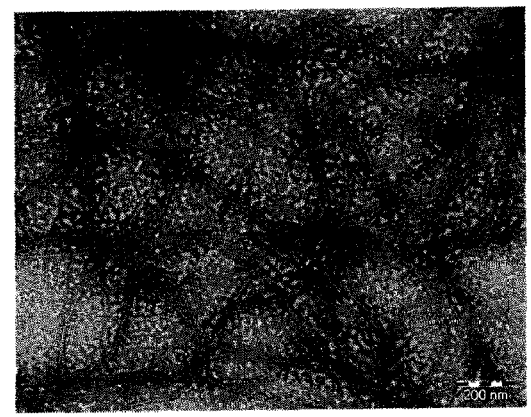
Figure 11:
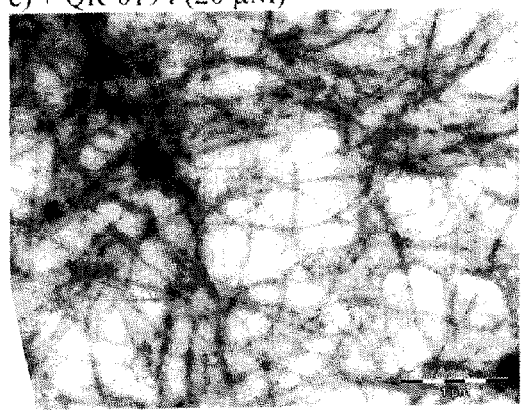
Figure 11:
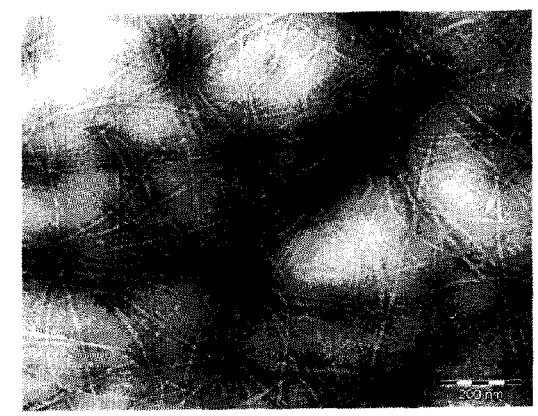
Figure 11:
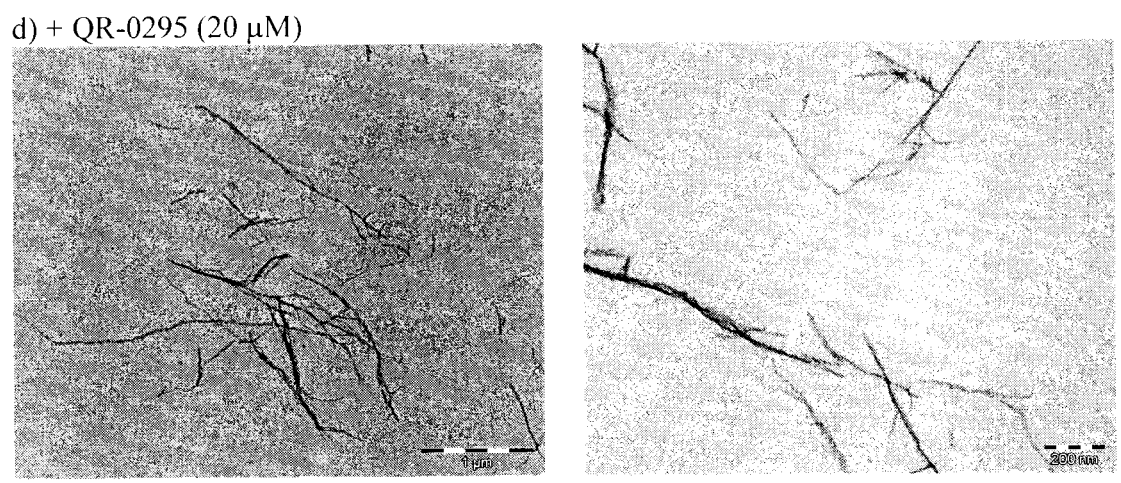

TEM of Aβ1-40 (20 µM) incubated in the absence (a) and presence of compounds (b,c), taken following the ThT aggregation assay is depicted in FIG. 11. Compounds QR-0112 (b) and QR-0194 (c), both at 20 µM, caused an increase in fibril formation but of a different morphology than those present in the control incubation (a). The incubation containing QR-0295 at 20 µM (d) had fibrils of similar morphology to the control, however there appeared to be a reduction in the amount of fibrils. The results collectively suggest that there are different mechanisms through which the compounds disrupt Aβ1-40 aggregation, with possibly more than one of the mechanisms being of therapeutic benefit. Micrographs on left have scale bars of 1 µm, those on the right have scale bars of 200 nm.

Figure 12:
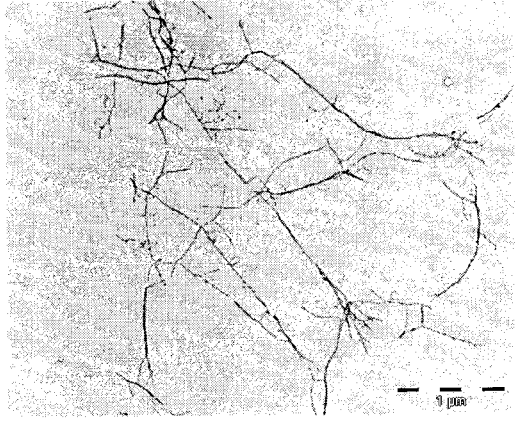
FIG. 12 is a TEM micrograph of Aβ1-40 (20 μM) incubated in the absence of ThT and in the absence (a) or presence (b,c) of compounds.
Figure 12:
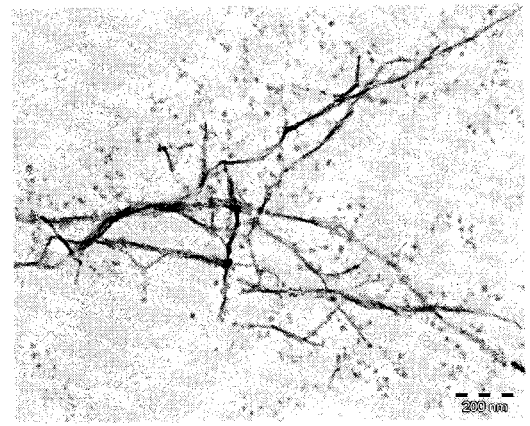
Figure 12:
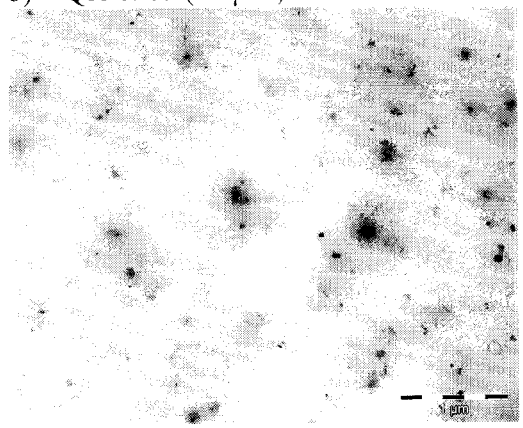
Figure 12:
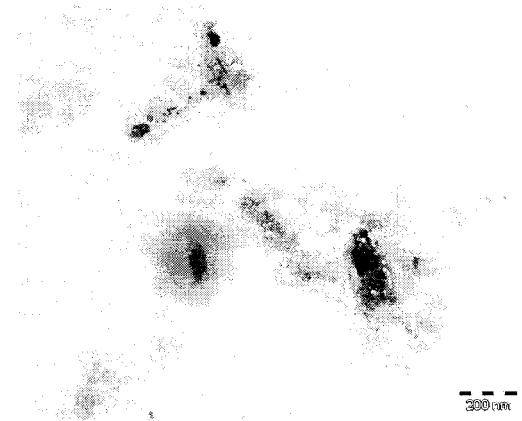
Figure 12:
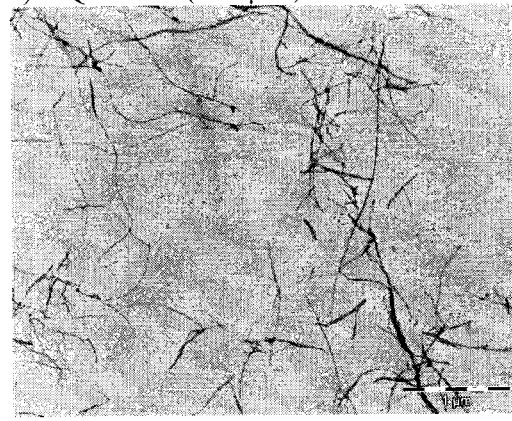
Figure 12:
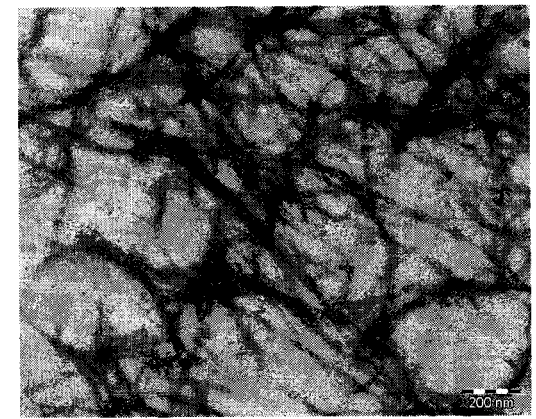

TEM of Aβ1-40 (20 µM) incubated in the absence of ThT and in the absence (a) or presence (b,c) of compounds is depicted in FIG. 12. QR-0263 at 20 (b) appeared to cause a reduction in fibrils relative to control (a), while QR-0273 (c) at 100 µM showed an increase in the number of fibrils. The fibrils in the QR-0273 incubation, however, appeared to be of a different morphology when compared to control, suggesting the compound has a modulating effect on fibril formation. Disrupting the normal aggregation of Aβ1-40 by accelerating the formation of non-native, non-toxic aggregates may be of therapeutic benefit. Micrographs on left have scale bars of 1 µm, those on the right have scale bars of 200 nm.

Figure 13:
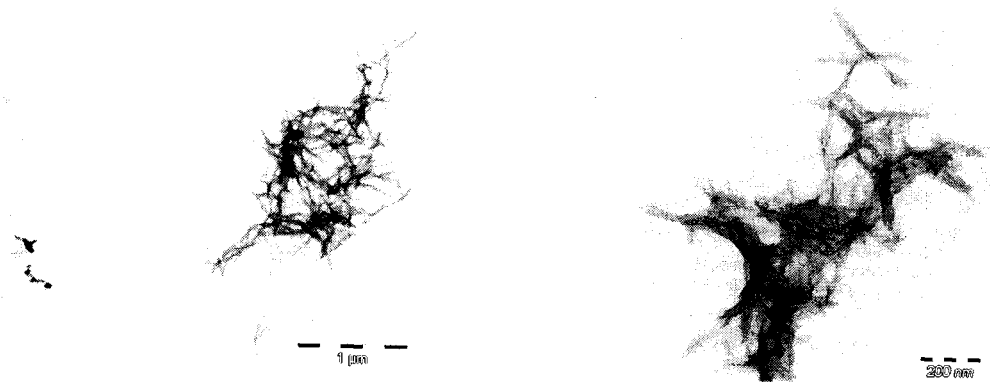
FIG. 13 is a TEM micrograph of Aβ1-40 (20 μM) incubated in the absence of ThT and in the absence (a) or presence (b,c) of compounds.
Figure 13:
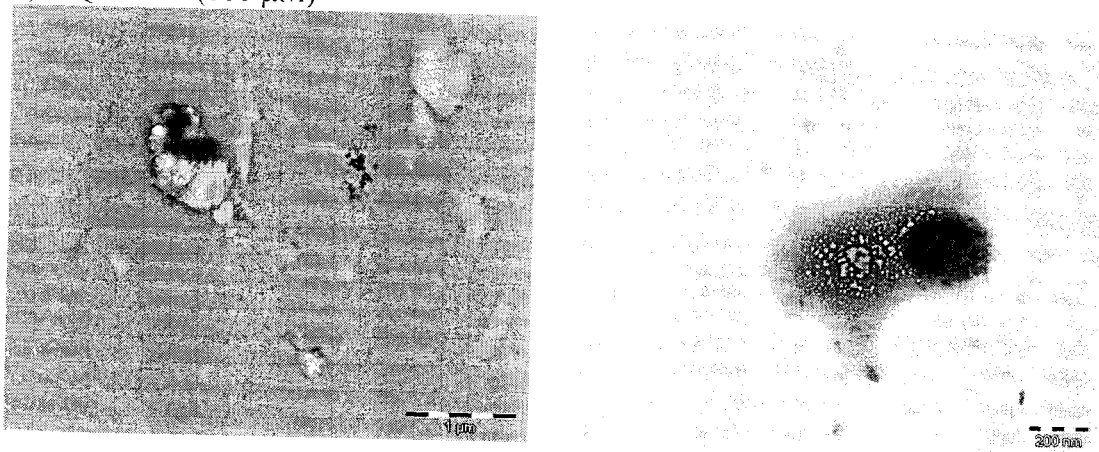
Figure 13:
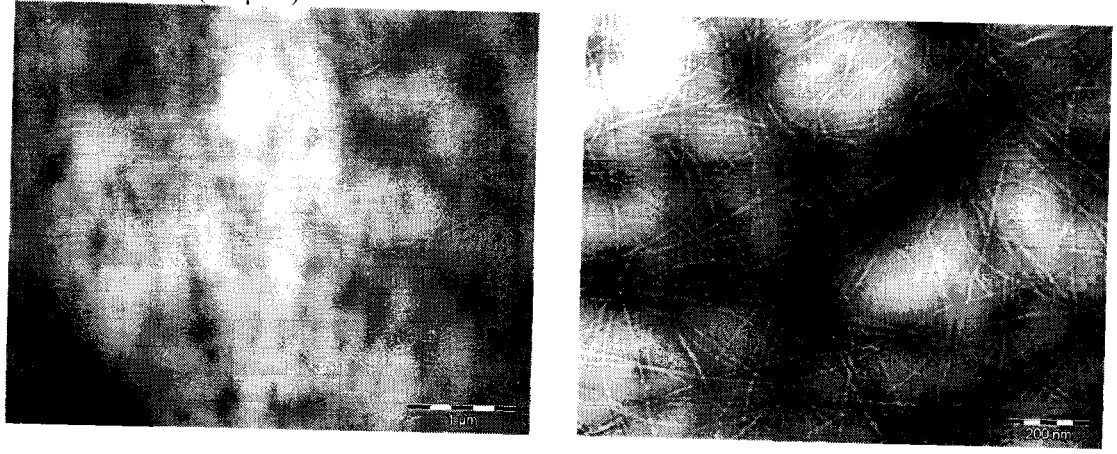

TEM of Aβ1-42 (20 µM) incubated in the absence of ThT and in the absence (a) or presence (b,c) of compounds is depicted in FIG. 13. QR-0185 at 100 µM (b) appeared to cause a decrease in fibrils relative to control (a), suggesting it may inhibit Aβ1-42 aggregation. QR-0194 (c) at 20 µM caused an apparent increase in the number of fibrils present relative to control (a). These fibrils. however, appeared to be of a different morphology when compared control suggesting the compound may disrupt the normal aggregation of Aβ1-42 into toxic aggregates. Micrographs on left have scale bars of 1 µm, those on the right have scale bars of 200 nm.

Figure 14:
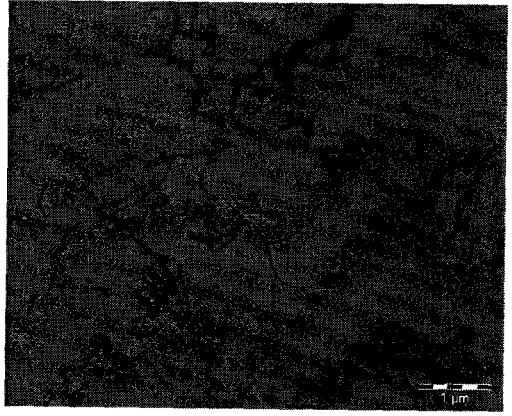
FIG. 14 is a TEM micrograph of Tau 441 (6 μM) incubated in the absence (a) and presence of compounds (b,c), taken following the ThS aggregation assay of EXAMPLE 52.
Figure 14:
Figure 14:
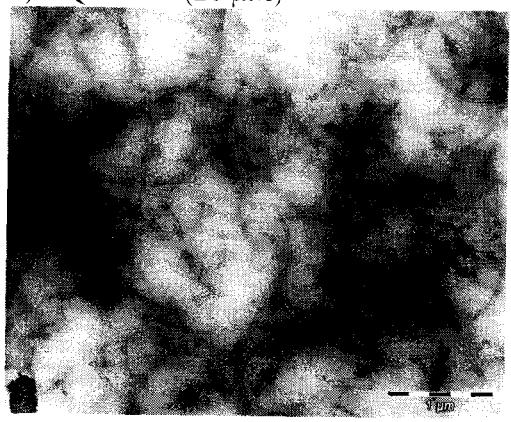
Figure 14:
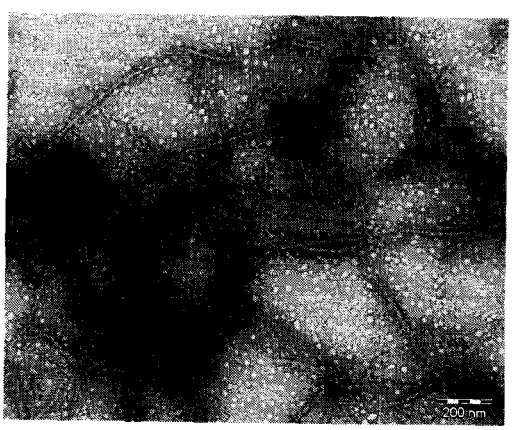
Figure 14:
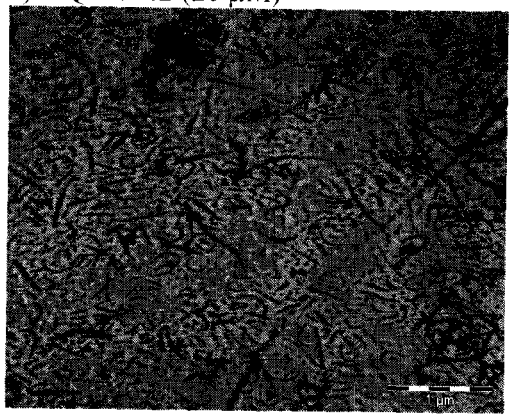
Figure 14:
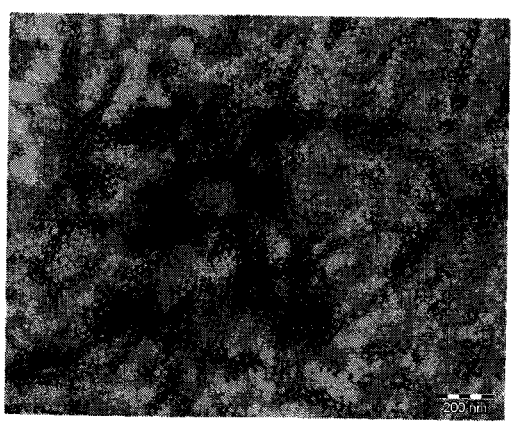

TEM of Tau 441 (6 µM) incubated in the absence (a) and presence of compounds (b.c), taken following the ThS aggregation assay is depicted in FIG. 14. QR-0281 (b) and QR-0262 (c), both at 20 µM, caused an increase in fibril formation relative to the control (a) but gave fibrils of different morphology. Incubations containing QR-0281 and QR-0262 also had spherical assemblies that were not present in the control. The results suggest that the compounds modulate Tau441 fibril formation and may therefore disrupt pathological aggregation of the protein. Micrographs on left have scale bars of 1 µm, those on the right have scale bars of 200 nm.

Figure 15:
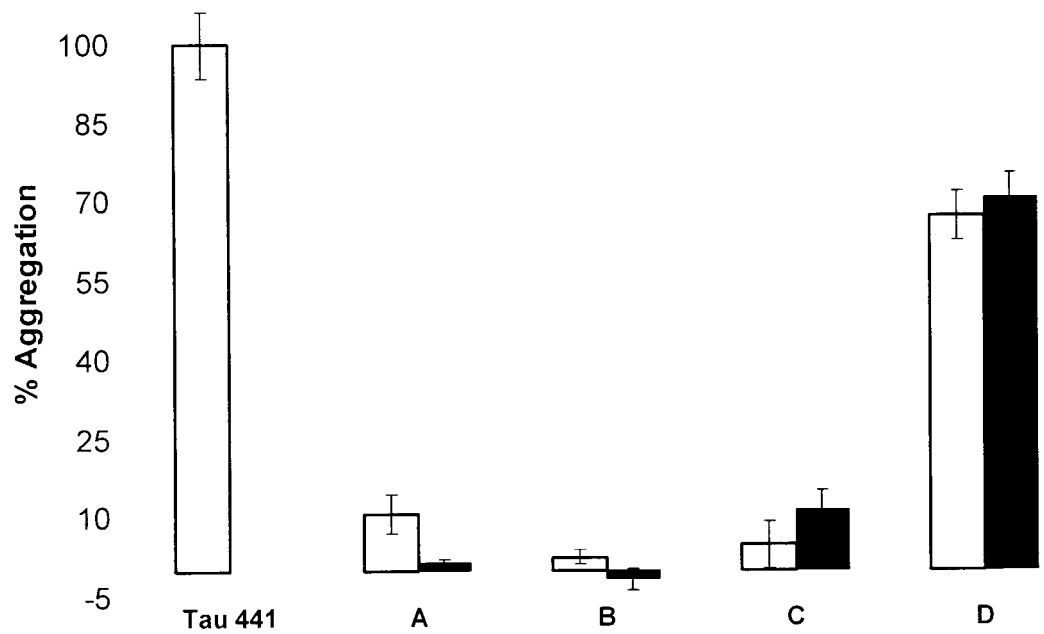
FIG. 15 is a graph of effects of compounds (QR-0244, QR-0263, QR-0281, and QR-0262, A-D, respectively) on Tau 441 aggregation after 24 hours incubation (37° C.) of EXAMPLE 52.

Referring to FIG. 15, ThS fluorescence assay showing the effect of compounds on Tau 441 aggregation after 24 hours incubation (37° C.). QR-0244. QR-0263, and QR-0281 (A-C respectively) greatly inhibited aggregation of Tau 441 (6 µM) at 50 µM (white bars) and 10 µM (black bars) is depicted. QR-0262 (D) only moderately inhibited Tau441 aggregation at these concentrations. Error bars represent standard deviation of n=3 replicates.

Figure 16:
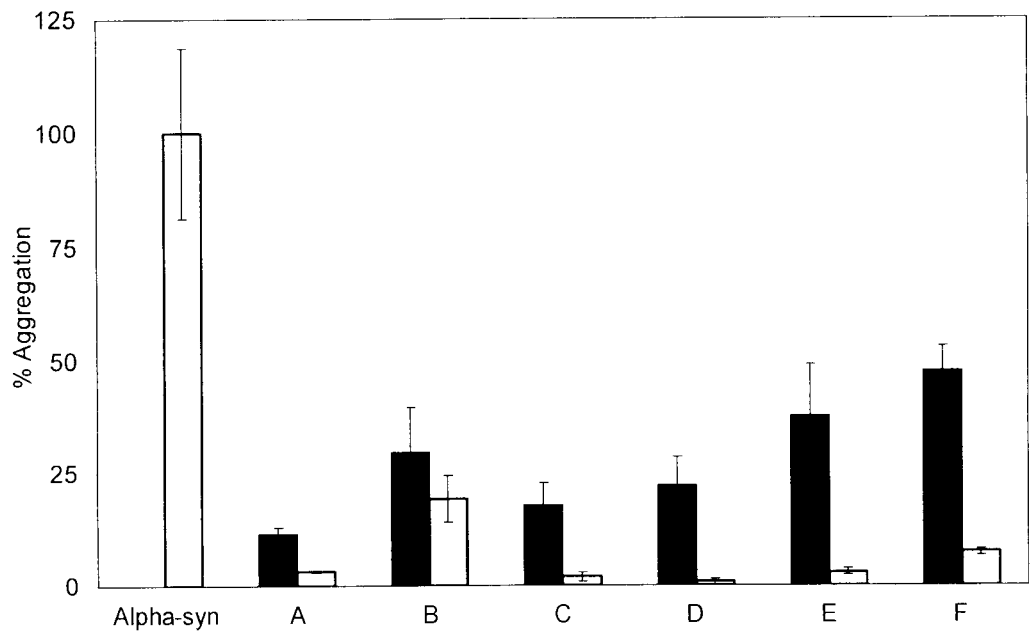
FIG. 16 is a graph of effects of compounds (QR-0189, QR-0194 QR-0212, QR-0217, QR-0176, A-E, respectively and resveratrol, F) on α-synuclein (4 μM) aggregation at 100 μM (white bars) and 20 μM (black bars) after 96 hours incubation (37° C.) of EXAMPLE 52.

Referring to FIG. 16, ThT fluorescence assay showing the effect of compounds on α-synuclein aggregation. QR-0189, QR-0194, QR-0212, QR-0217, QR-0176, and resveratrol (A-F, respectively) all showed inhibition of α-synuclein (4 µM) aggregation at 100 µM (white bars) and 20 µM (black bars) after 96 hours incubation (37° C.) is depicted. Error bars represent standard deviation of n=3 replicates. As α-synuclein aggregates have been implicated in the pathogenesis of a number of neurodegenerative diseases, e.g. Parkinson's disease (A L Fink, *Acc Chem Res* 2006, 39: 628-634) and Alzheimer's disease (J E Duda et al., *J Neurosci Res* 2000. 61:127-127), compounds that inhibit the protein's aggregation may be of therapeutic benefit.

Figure 17:
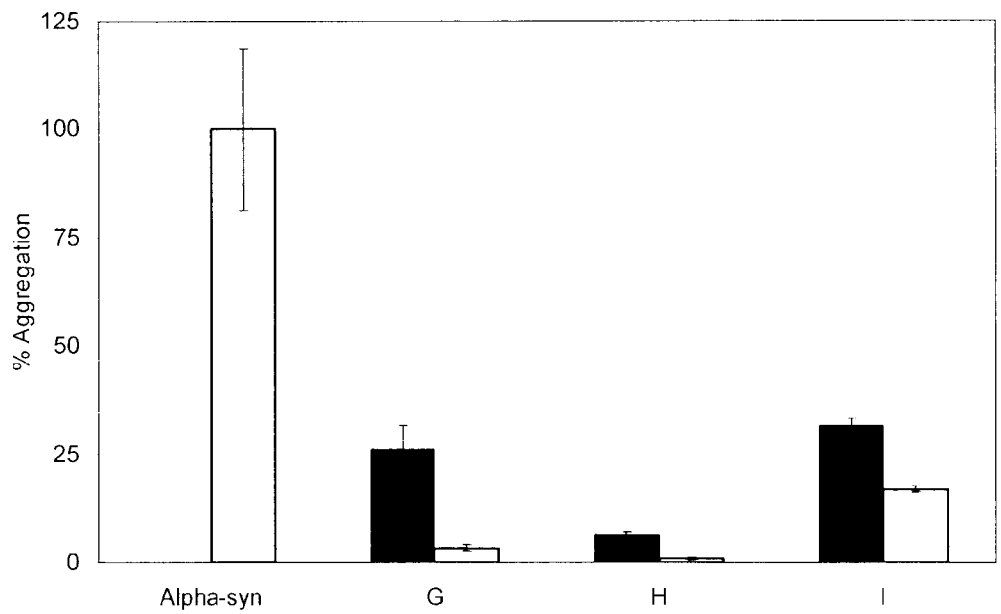
FIG. 17 is a graph of compounds (QR-0164, QR-0147, and QR-0162, G-I, resepectively) on α-synuclein aggregation (4 μM) at 50 μM (white bars) and 10 μM (black bars) after 96 hours incubation (37° C.) of EXAMPLE 52.

ThT fluorescence assay showing the effect of compounds on α-synuclein aggregation. QR-0164, QR-0147, and QR-0162 (G-I) all showed inhibition of α-synuclein (4 µM) aggregation at 50 µM (white bars) and 10 µM (black bars) after 96 hours incubation (37° C.) is depicted in FIG. 17. Error bars represent standard deviation of n=3 replicates.

Synaptic connections among neurons in cell cultures might undergo long-lasting enhancement of synaptic strength that resembles long-term potentiation (LTP) in slice preparations and in vivo in several critical ways (Malgaroli, A., et al., *Nature* (1992) 357: 134-9; Arancio, O., et al., *Nature* (1995) 376: 74-80; Arancio, O., et al. *Cell* (1996) 87: 1025-35; Arancio, O., et al. *J. Physiol.* (1994) 481(Pt 2): 395-405; Arancio, O. et al., J. Neurophysiol. (1991) 65: 899-913) including: a) NMDA receptor activation is necessary for LTP induction, b) $Ca^{2+}$ influx through postsynaptic NMDA receptor channels is required for LTP induction, c) high frequency stimulation of the presynaptic neuron reliably induces LTP, d) potentiation can also be induced through pairing of low frequency stimulation of the presynaptic neuron with depolarization of the postsynaptic neuron. Thus, cell culture preparation is an excellent system to examine whether synaptic transmission is altered in transgenic models of AD, and to attempt rescuing changes of synaptic transmission through application of potential therapeutic agents. Towards this end, a model of dissociated cell cultures derived from the hippocampus of APP/PS1 mice has been developed (Trinchese, F., et al., *J. Mol. Neurosci.* (2004) 24: 15-21) in order to look at changes of synaptic transmission caused by Aβ elevation. These studies have demonstrated that cultured hippocampal neurons from APP/PS1 mice which release into their medium two major types of Aβ peptides, Aβ40 and Aβ42, recapitulate the in vivo localization and accumulation of Aβ42 and show an increase in number of functional presynaptic release sites associated with lack of glutamate-induced long-lasting increase in active release site number.

Electrophysiological analysis was performed on males (see detailed description in Gong, B., el al., *Cell* (2006) 126: 775-88). Hippocampal slices (400 µm) were cut with a tissue chopper and maintained in an interface chamber at 29° C. for 90 min prior to recording. Briefly. CA1 fEPSPs were recorded by placing both the stimulating and the recording electrodes in CA1 stratum radiatum. Basal synaptic transmission was assayed by plotting the stimulus voltages against slopes of fEPSP. For LTP experiments, a 15 min baseline was recorded every min at an intensity that evokes a response ~35% of the maximum evoked response. LTP was induced using θ-burst stimulation (4 pulses at 100 Hz, with the bursts repeated at 5 Hz and each tetanus including 3 ten-burst trains separated by 15 sec).

Figure 18:
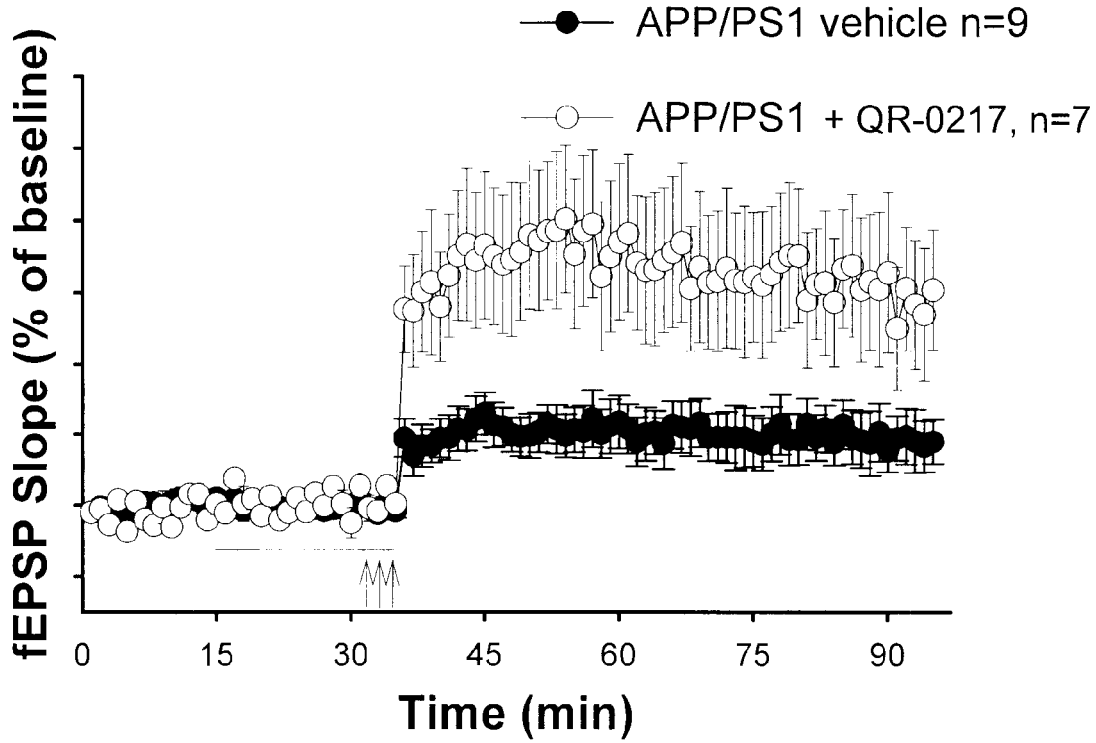
FIG. 18 is a graph showing compound QR-0217 (50 μM) significantly (P=0.022) rescuing impairment of LTP in APP/PS1 transgenic mice hippocampal slices (capability of QR-0217 to reduce memory impairments caused by Aβ neurotoxicity).

As seen in FIG. 18. compound QR-0217 (50 µM) significantly rescued impairment of LTP in the APP/PS1 transgenic mice hippocampal slices. This suggests the compound is able to reduce memory impairments caused by Aβ neurotoxicity.

In the preceding specification, the invention has been described with reference to specific exemplary embodiments. Those skilled in the art will recognize, or be able to ascertain using no more than routine experimentation, many equivalents to the specific embodiments to the methods described herein. Such equivalents are intended to be encompassed by the following claims.

What is claimed is:

1. A compound selected from the group consisting of 3-(2-methoxynaphthalen-6-yl)-1H-indole-5-carboxylic acid (QR-0216) and 3-(2-hydroxynaphthalen-6-yl)-1H-indole-5-carboxylic acid QR-0217; or a pharmaceutically acceptable salt thereof.

2. A pharmaceutical composition comprising pharmaceutically acceptable excipients and an effective amount of a compound of claim 1 to treat tauopathies, cerebral amyloid angiopathy, Lewy body diseases, Alzheimer's disease, Parkinson's disease, dementia, Huntington's disease, prion-based spongiform encephalopathy or a combination thereof.

3. The pharmaceutical composition of claim 2, wherein the neurodegenerative disease is Alzheimer's disease.

4. A pharmaceutical composition comprising pharmaceutically acceptable excipients and an effective amount of a compound of claim 1 to treat tauopathies, cerebral amyloid angiopathy, Lewy body diseases, Alzheimer's disease, Parkinson's disease, dementia, Huntington's disease, prion-based spongiform encephalopathy or a combination thereof, to provide a dose of up to 300 mg of the compound to a subject.

5. The pharmaceutical composition of claim 4, wherein the composition provides a dose of from 100-300 mg of the compound to a subject.

6. The pharmaceutical composition of claim 4, wherein the composition provides a dose of from 150-250 mg of the compound to a subject.

* * * * *